US007667068B2

(12) United States Patent
Miller et al.

(10) Patent No.: US 7,667,068 B2
(45) Date of Patent: *Feb. 23, 2010

(54) PROCESS FOR REACTIVE ESTERIFICATION DISTILLATION

(75) Inventors: Dennis J. Miller, Okemos, MI (US); Navinchandra Asthana, East Lansing, MI (US); Aspi Kolah, East Lansing, MI (US); Dung T. Vu, Grand Rapids, MI (US); Carl T. Lira, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/414,672

(22) Filed: Apr. 28, 2006

(65) Prior Publication Data

US 2006/0252956 A1    Nov. 9, 2006

Related U.S. Application Data

(63) Continuation-in-part of application No. 10/894,307, filed on Jul. 19, 2004.

(51) Int. Cl.
*C07C 67/08* (2006.01)
(52) U.S. Cl. .................................... 560/204
(58) Field of Classification Search ............... 560/204
See application file for complete search history.

(56) References Cited

U.S. PATENT DOCUMENTS

| 1,400,849 | A | | 12/1921 | Backhaus |
| 2,551,625 | A | * | 5/1951 | Morrell et al. ............... 203/53 |
| 2,575,243 | A | * | 11/1951 | Carlson et al. ............... 203/60 |
| 2,587,753 | A | * | 3/1952 | O'Connor et al. ........... 568/923 |
| 4,435,595 | A | * | 3/1984 | Agreda et al. ............... 560/234 |
| 5,008,046 | A | | 4/1991 | Bremus et al. |
| 5,536,856 | A | * | 7/1996 | Harrison et al. ............. 554/164 |
| 5,719,311 | A | * | 2/1998 | Wu et al. ...................... 560/98 |
| 6,045,703 | A | * | 4/2000 | Miller ......................... 210/659 |
| 6,586,609 | B2 | * | 7/2003 | Ruggieri et al. ............. 554/174 |
| 6,815,525 | B2 | * | 11/2004 | DeBruin ...................... 528/272 |
| 7,045,100 | B2 | * | 5/2006 | Ergun et al. ................. 422/129 |
| 2006/0014977 | A1 | * | 1/2006 | Miller et al. ................. 560/179 |
| 2007/0129565 | A1 | | 6/2007 | Sutton et al. |

FOREIGN PATENT DOCUMENTS

GB          1294371      10/1972
WO       WO9851657     11/1998

OTHER PUBLICATIONS

Nong, L., et al., Synthesis of Tributyl Citrate with Aluminum PHosphotungstate Supported on activated Carbon, Jingxi Huagong Zhongjianti (2004), 34(3), 50-52, 54. (Abstract).

Shi, et al., Synthesis of tributyl citrate catalyzed by solid superacid S2082-/Ti02-Si02, Yingyong Huagong (2004), 33(3), 41-43. (Abstract).
Zheng et al., Synthesis of tributyl citrate catalyzed by tetrabutyl titanate, Jingxi Huagong Zhongjianti (2004), 34(1), 28-30. (Abstract).
Asthana et al., Org. Process Res. & Dev., 9, 599-607 (2005).
Deng et al., The synthesis of tributyl citrate catalyzed by sodium hydrogen sulfate, Jingxi Huagong Zhongjianti (2003), 33(6), 49-50. (Abstract).
Gangadwala et al., Ind. Eng. Chem. Res. 42 2146-2155 (2003).
Liu et al., Catalytic synthesis of tri-butyl citrate with dealuminated USY zeolite, Hecheng Huaxue (2003), 11(2), 175-177. (Abstract).
Van Baten et al Catalysis Today, 69, 371-377 (2001).
Gotze et al., Catalysis Today., 69, 201-208 (2001).
Smejkal et al., Chem. Eng. Sci., 56, 365-370 (2001).
Ratheesh and Kannan., Chem. Eng. J., 104, 45-54 (2004).
Kolodziej et al., Chem. Eng. Proc., 43, 457-464 (2004).
Schmitt et al., Chem. Eng. Proc., 43, 397-409 (2004).
Schmitt et al., Chem. Eng. Proc., 44, 677-685 (2005).
Bock et al., Chem. Eng. Prog. 36, 101-109 (1997).
Omota et al., Chem. Eng. Sci., 58, 3159-3174 (2003).
Tao, X., Huazue Shijie, 39(6), 302-304 (1998). (Abstract).
Asthana, Navinchandra et al., Reactive Distillation for the BioRefinery:Production of Organic Acid Esters, Prepr. Pap.-Am. Chem. Soc., Div. Fuel Chem. 2005, 50(2), (XP008089894)p. 683-684.
Choi, Jong et al., Reaction Kinetics of Lactic Acid with Methanol Catalyzed by Acid Resins, International Journal of Chemical Kinetics, (XP-001057571)vol. 28, 37-41 (1996).
EP 05760216 (PCT/US2005021742)Supplementary European Search Report.
Sharma, M. M., Mahajani, S.M. Industrial Application of Reactive Distillation in Reactive Distillation Edited by Sundmacher K. and Kienle A., Wiley VCH, Germany, 1 (2003).
Taylor, R., et al., Modelling Reactive Distillation. Chem. Eng. Sci., 55, 5183 (2000).
Modeling of Homogeneous and heterogeneous Reactive Distillation Processes, Chapter 9 in "Reactive Distillation" Editors: K. Sundmacher, A. Kienle, pp. 217-240, Wiley-VCH, Mannheim (2003).
Hiwale, R.S., et al., Industrial Applications of Reactive Distillation: Recent Trends. Int. J. of Chem. React. Eng., 2, Review R1 (2004).
Spes, H., Catalytic reactions in ion-exchange columns under conditions of the chemical equilibrium shift. WackerChem.Werk, Burghausen, Ger., Germany. Chemiker-Zeitung (1966), 90(13), 443-446. (Abstract).
Stankiewicz and Moulijn, 2000.
Moritz and Hasse, (Chem. Eng. Sci. 54, 1367-1374 (1999).
Hanika et al., (Chem. Eng. Sci. 54, 5205-5209 (1999).

* cited by examiner

*Primary Examiner*—Elvis O Price
(74) *Attorney, Agent, or Firm*—Ian C. McLeod

(57) ABSTRACT

A process for producing organic acid di- or tri-esters, particularly citric acid tri-esters, with the available acid groups esterified using countercurrent reactive distillation using acid catalysts in a structured packing is described. In the reactive distillation an organic acid di- or tri-ester is formed by chemical reaction and purified to its final state within the single column. Organic acid di- or tri-esters are produced at relatively low cost, with less waste production in by-products of the reaction, and in a less complicated manner than prior processes. Organic acid di- and tri-esters have uses as solvents, as plasticizers and in conversion products.

21 Claims, 68 Drawing Sheets

Esterification Citric Acid Solution
Reaction Conditions: Mole Ratio of Ethanol to Citric acid, 15:1; Catalyst Loading, 5 wt%, Reaction Temperature, 78°C. (■, CA; ●, MEC; ▲, DEC; ×, TEC)

Esterification Citric Acid Solution
Reaction Conditions: Mole Ratio of Ethanol to Citric acid, 15:1; Catalyst Loading, 5 wt%, Reaction Temperature, 78°C. (□, EtOH; ○, Water)

Esterification Citric Acid Solution
Reaction Conditions: Mole Ratio of Ethanol to Citric acid, 15:1; Catalyst Loading, 5 wt%, Reaction Temperature, 90°C. (■, CA; ●, MEC; ▲, DEC; ×, TEC)

Esterification Citric Acid Solution
Reaction Conditions: Mole Ratio of Ethanol to Citric acid, 15:1; Catalyst Loading, 5 wt%, Reaction Temperature, 90°C. (□, EtOH; O, Water)

Esterification Citric Acid Solution
Reaction Conditions: Mole Ratio of Ethanol to Citric acid, 15:1; Catalyst Loading, 5 wt%, Reaction Temperature, 100°C. (■, CA; ●, MEC; ▲, DEC; ×, TEC)

Esterification Citric Acid Solution
Reaction Conditions: Mole Ratio of Ethanol to Citric acid, 15:1; Catalyst Loading, 5 wt%, Reaction Temperature, 100°C. (□, EtOH; O, Water)

Esterification Citric Acid Solution
Reaction Conditions: Mole Ratio of Ethanol to Citric acid, 15:1; Catalyst Loading, 5 wt%, Reaction Temperature, 110°C. (■, CA; ●, MEC; ▲, DEC; ×, TEC)

Esterification Citric Acid Solution
Reaction Conditions: Mole Ratio of Ethanol to Citric acid, 15:1; Catalyst Loading, 5 wt%, Reaction Temperature, 110°C. (□, EtOH; O, Water)

Esterification Citric Acid Solution
Reaction Conditions: Mole Ratio of Ethanol to Citric acid, 15:1; Catalyst Loading, 5 wt%, Reaction Temperature, 120°C. (■, CA; ●, MEC; ▲, DEC; ×, TEC)

Esterification Citric Acid Solution
Reaction Conditions: Mole Ratio of Ethanol to Citric acid, 15:1; Catalyst Loading, 5 wt%, Reaction Temperature, 120°C. (□, EtOH; ○, Water)

Esterification Citric Acid Solution
Reaction Conditions: Mole Ratio of Ethanol to Citric acid, 15:1; Catalyst Loading, 3 wt%, Reaction Temperature, 120°C. (■, CA; ●, MEC; ▲, DEC; ×, TEC)

Esterification Citric Acid Solution
Reaction Conditions: Mole Ratio of Ethanol to Citric acid, 15:1; Catalyst Loading, 3 wt%, Reaction Temperature, 120°C. (□, EtOH; ○, Water)

Esterification Citric Acid Solution
Reaction Conditions: Mole Ratio of Ethanol to Citric acid, 15:1; Catalyst Loading, 2 wt%, Reaction Temperature, 120°C. (■, CA; ●, MEC; ▲, DEC; ×, TEC)

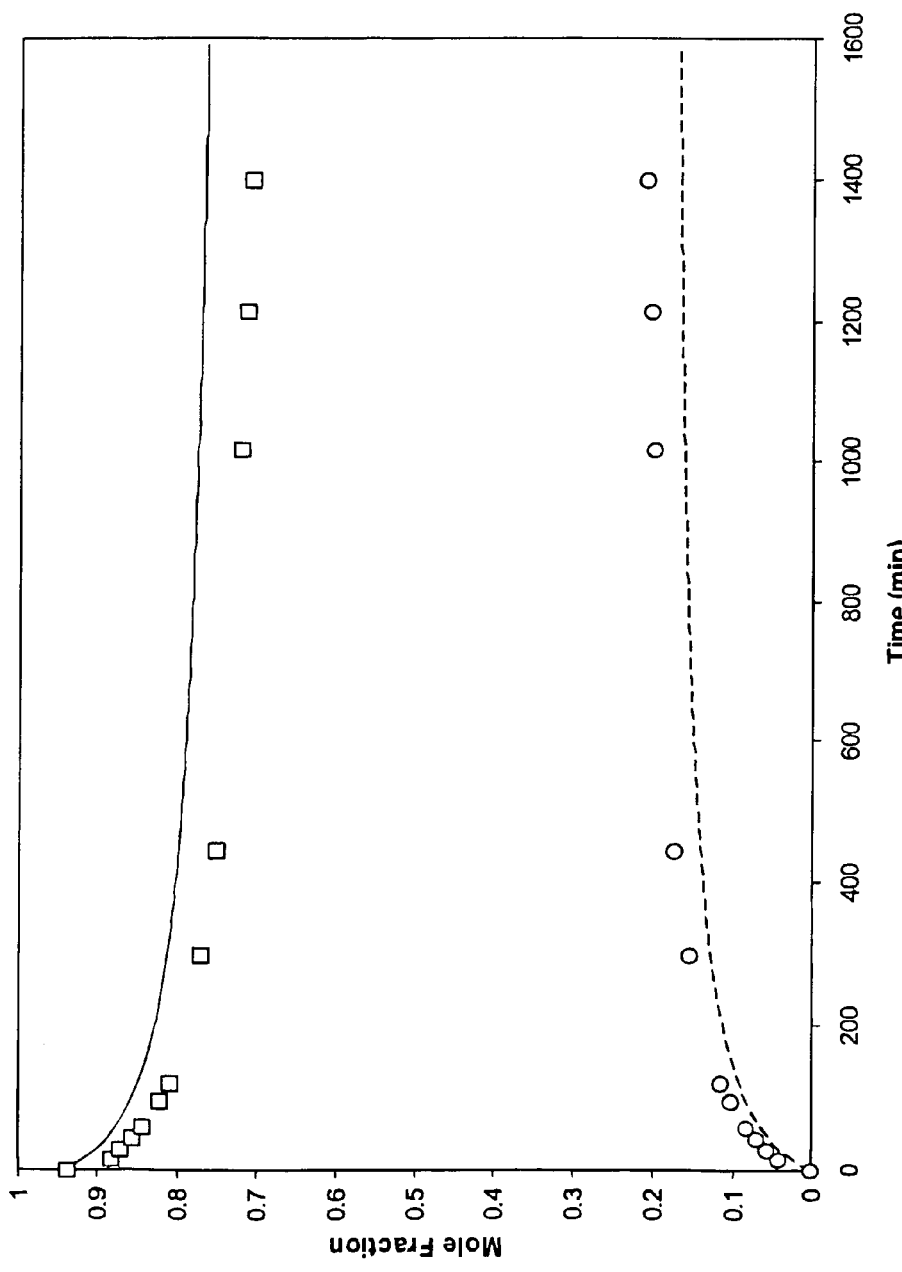

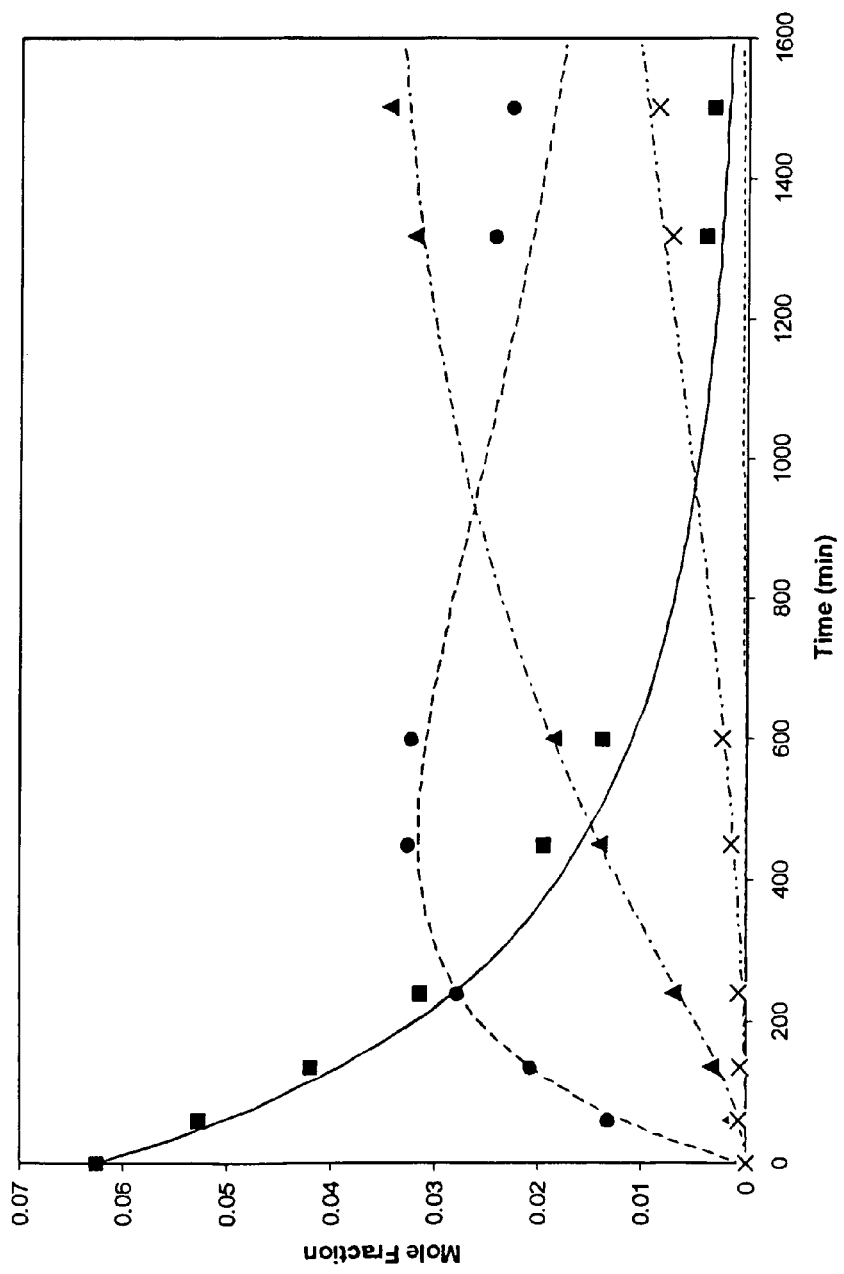

Esterification Citric Acid Solution
Reaction Conditions: Mole Ratio of Ethanol to Citric acid, 15:1; Catalyst Loading, 3 wt%, Reaction Temperature, 78°C. (□, EtOH; ○, Water)

Esterification Citric Acid Solution
Reaction Conditions: Mole Ratio of Ethanol to Citric acid, 15:1; Catalyst Loading, 2 wt%, Reaction Temperature, 78°C. (■, CA; ●, MEC; ▲, DEC; ×, TEC)

Esterification Citric Acid Solution
Reaction Conditions: Mole Ratio of Ethanol to Citric acid, 15:1; Catalyst Loading, 2 wt%, Reaction Temperature, 78°C. (□, EtOH; ○, Water)

Esterification Citric Acid Solution

Reaction Conditions: Mole Ratio of Ethanol to Citric acid, 15:1; Catalyst Loading, 1 wt%, Reaction Temperature, 78°C. (■, CA; ●, MEC; ▲, DEC; ×, TEC)

Esterification Citric Acid Solution
Reaction Conditions: Mole Ratio of Ethanol to Citric acid, 15:1; Catalyst Loading, 1 wt%, Reaction Temperature, 78°C. (□, EtOH; O, Water)

Esterification Citric Acid Solution
Reaction Conditions: Mole Ratio of Ethanol to Citric acid, 20:1; Catalyst Loading, 5 wt%, Reaction Temperature, 120°C. (■, CA; ●, MEC; ▲, DEC; ×, TEC)

Esterification Citric Acid Solution
Reaction Conditions: Mole Ratio of Ethanol to Citric acid, 20:1; Catalyst Loading, 5 wt%, Reaction Temperature, 120°C. (□, EtOH; O, Water)

Esterification Citric Acid Solution
Reaction Conditions: Mole Ratio of Ethanol to Citric acid, 10:1; Catalyst Loading, 5 wt%, Reaction Temperature, 120°C. (□, EtOH; ○, Water)

Esterification Citric Acid Solution
Reaction Conditions: Mole Ratio of Ethanol to Citric acid, 5:1; Catalyst Loading, 5 wt%, Reaction Temperature, 120°C. (■, CA; ●, MEC; ▲, DEC; ×, TEC)

Esterification Citric Acid Solution
Reaction Conditions: Mole Ratio of Ethanol to Citric acid, 5:1; Catalyst Loading, 5 wt%, Reaction Temperature, 120°C. (□, EtOH; O, Water)

Self-catalyzed Esterification Citric Acid Solution
Reaction Conditions: Mole Ratio of Ethanol to Citric acid, 20:1; Reaction Temperature, 120°C.
(■, CA; ●, MEC; ▲, DEC; ×, TEC)

Self-catalyzed Esterification Citric Acid Solution
Reaction Conditions: Mole Ratio of Ethanol to Citric acid, 20:1; Reaction Temperature, 120°C.
(□, EtOH; O, Water)

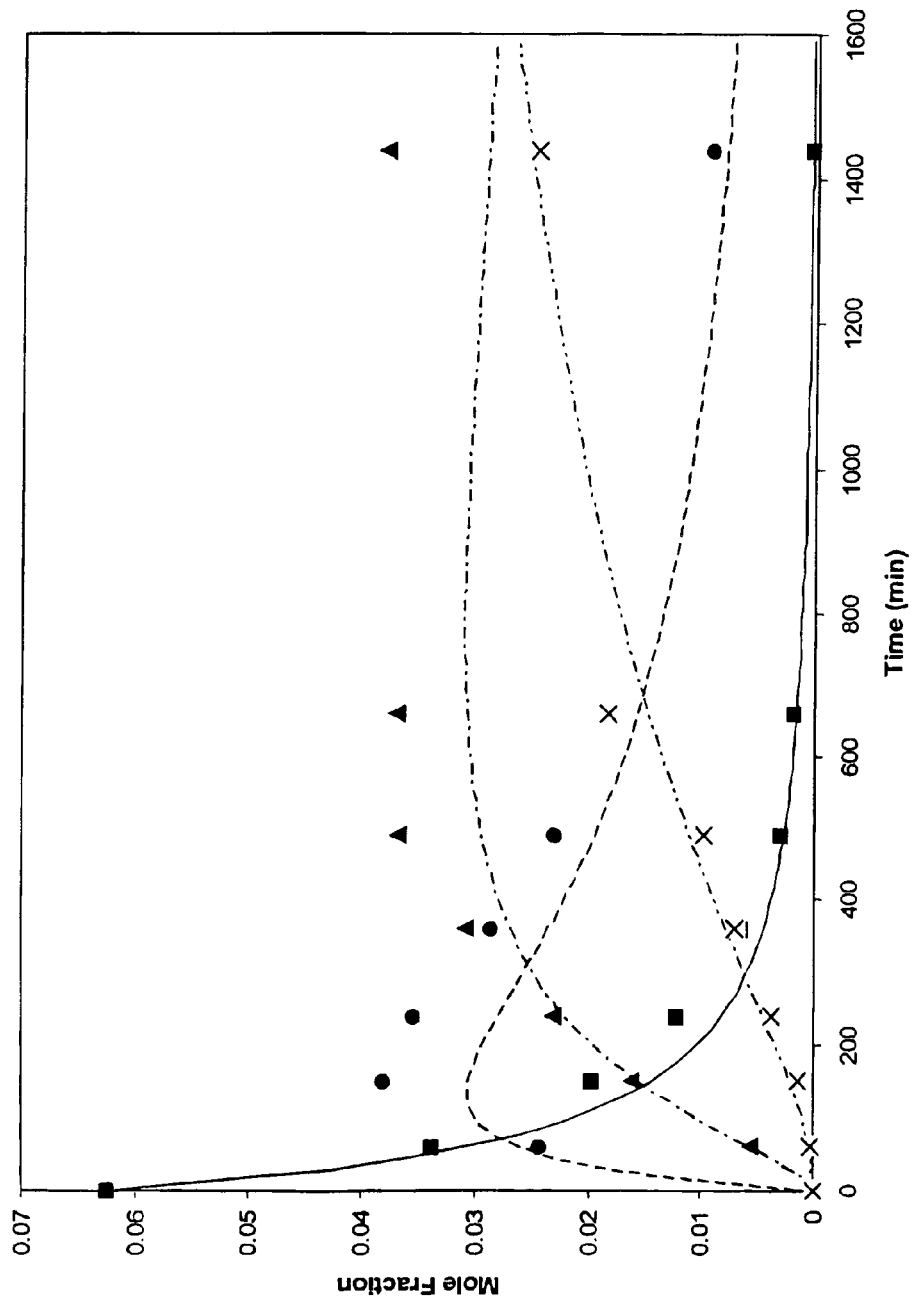

Self-catalyzed Esterification Citric Acid Solution
Reaction Conditions: Mole Ratio of Ethanol to Citric acid, 15:1; Reaction Temperature, 120°C.
(□, EtOH; O, Water)

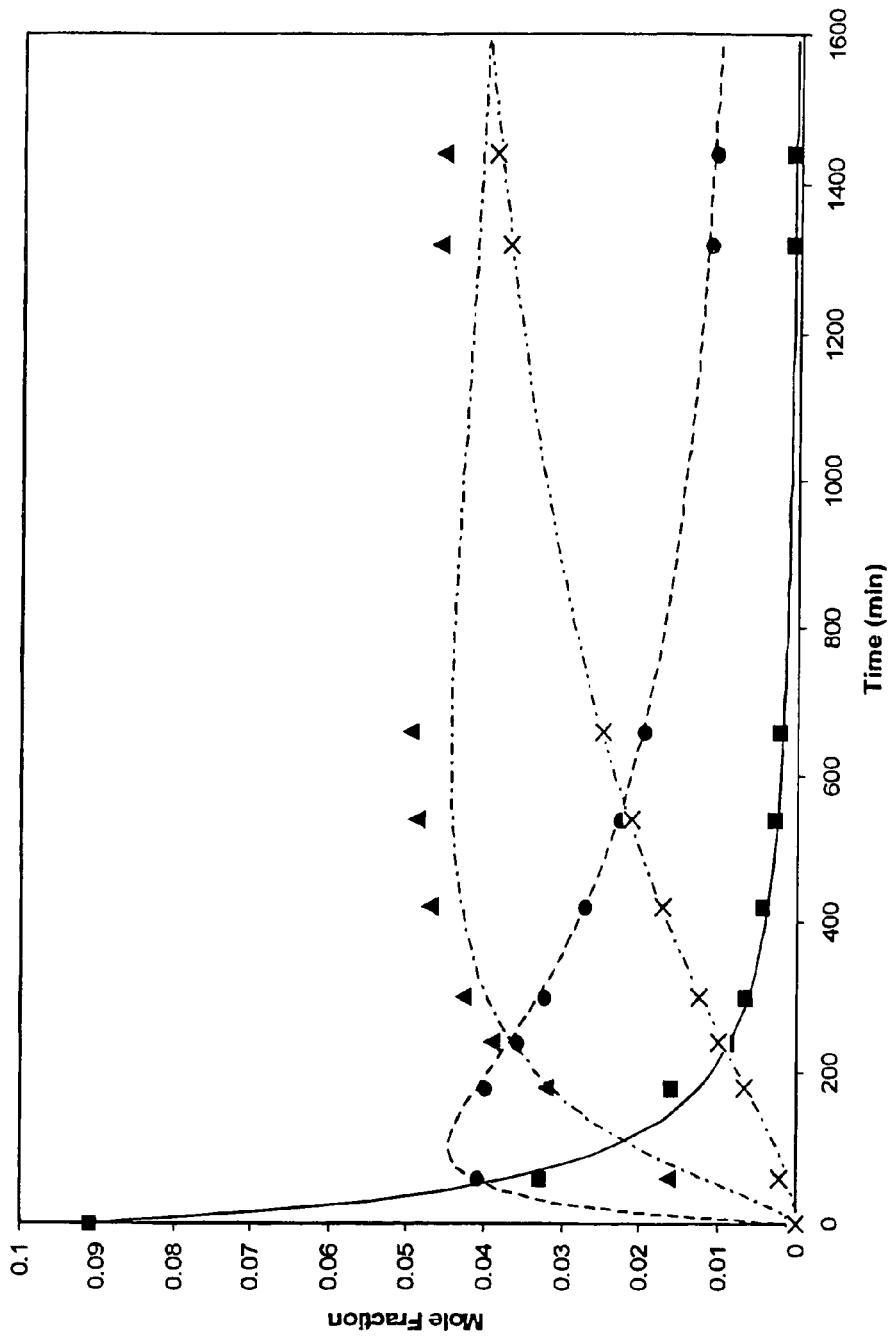

Self-catalyzed Esterification Citric Acid Solution
Reaction Conditions: Mole Ratio of Ethanol to Citric acid, 10:1; Reaction Temperature, 120°C.
(□, EtOH; O, Water)

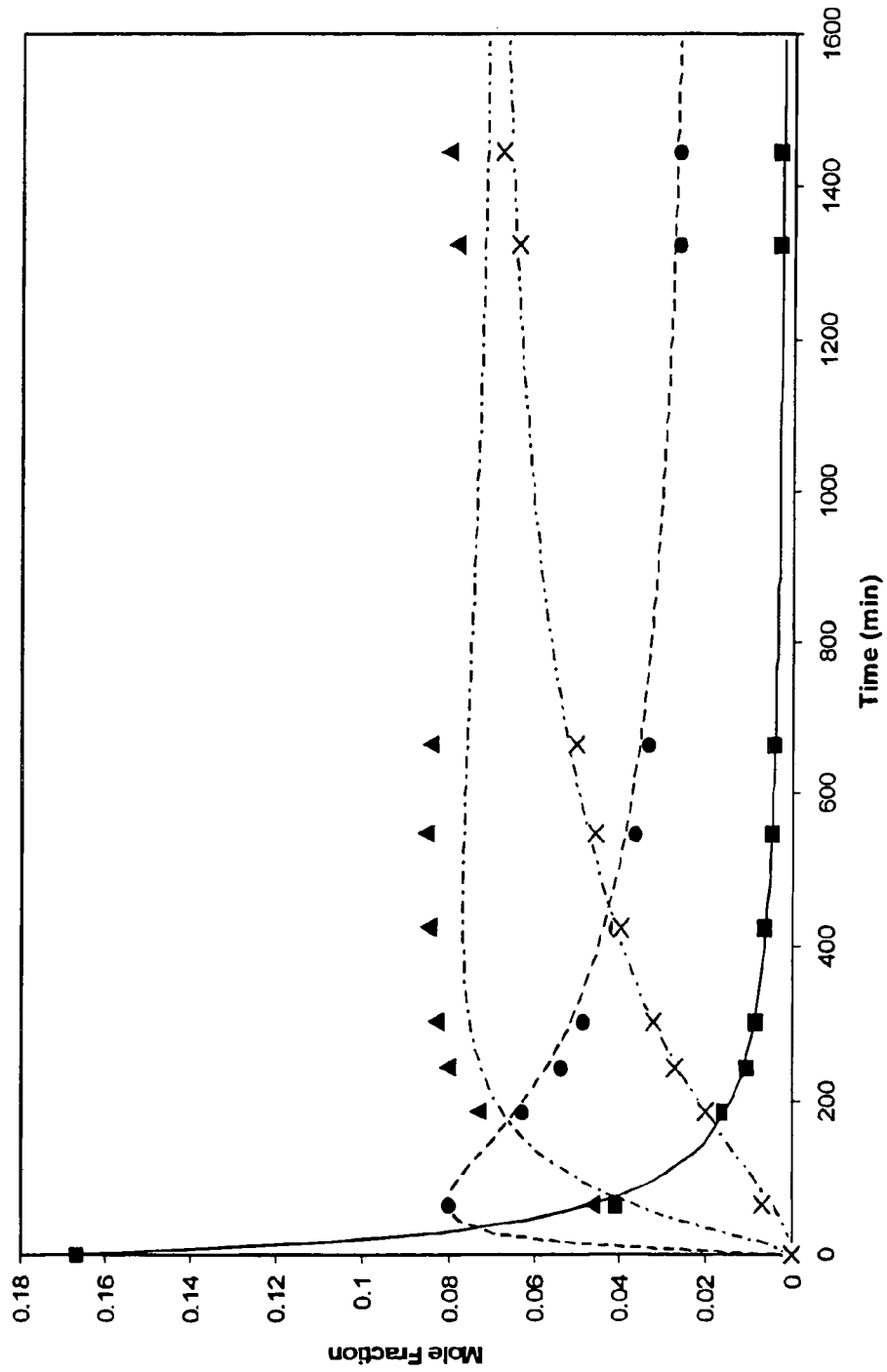

Self-catalyzed Esterification Citric Acid Solution
Reaction Conditions: Mole Ratio of Ethanol to Citric acid, 15:1; Reaction Temperature, 78°C.
(■, CA; ●, MEC; ▲, DEC; ×, TEC)

Self-catalyzed Esterification Citric Acid Solution
Reaction Conditions: Mole Ratio of Ethanol to Citric acid, 15:1; Reaction Temperature, 78°C.
(□, EtOH; O, Water)

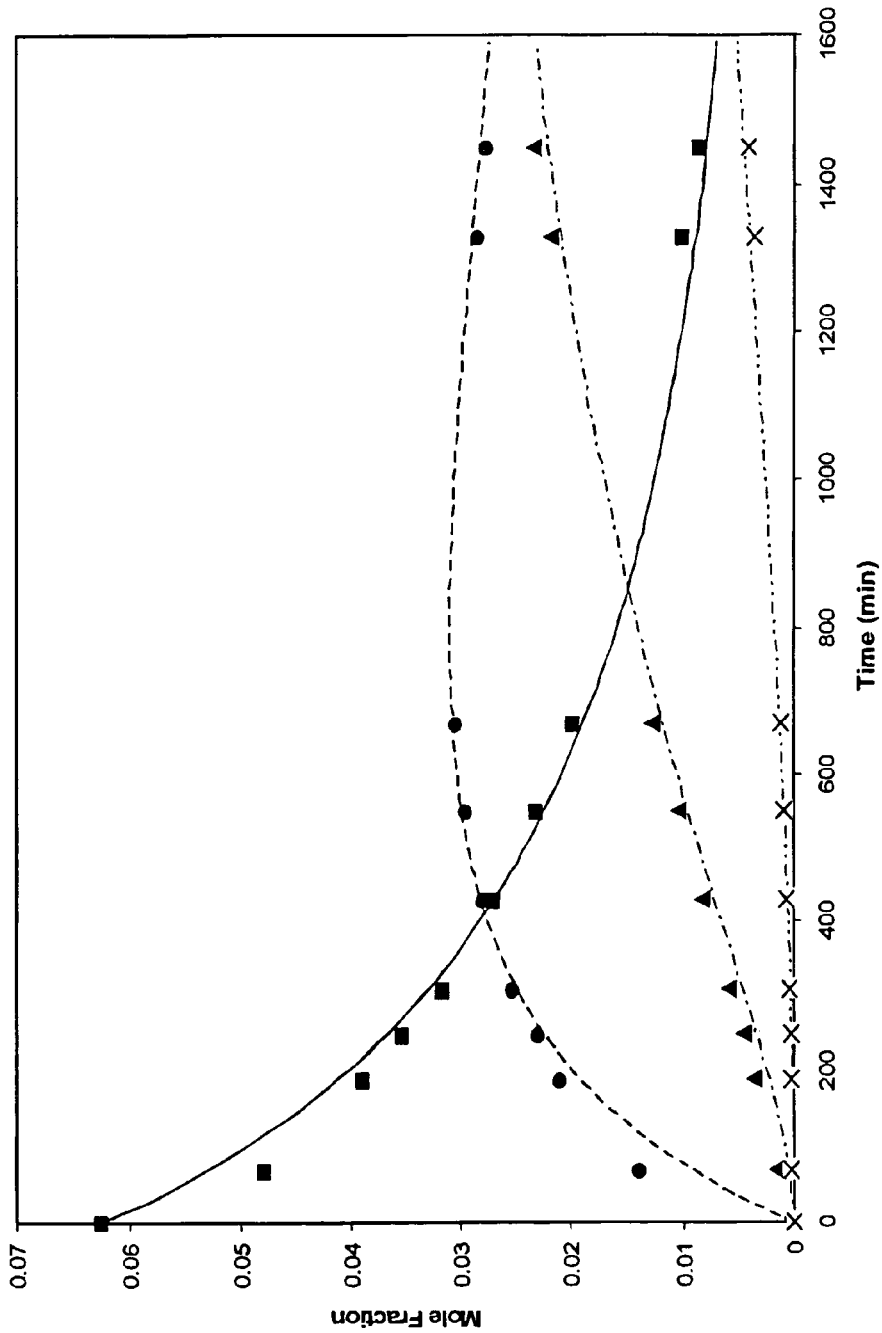

Self-catalyzed Esterification Citric Acid Solution
Reaction Conditions: Mole Ratio of Ethanol to Citric acid, 15:1; Reaction Temperature, 90°C.
(□, EtOH; O, Water)

Self-catalyzed Esterification Citric Acid Solution
Reaction Conditions: Mole Ratio of Ethanol to Citric acid, 15:1; Reaction Temperature, 100°C.
(■, CA; ●, MEC; ▲, DEC; ×, TEC)

Self-catalyzed Esterification Citric Acid Solution
Reaction Conditions: Mole Ratio of Ethanol to Citric acid, 15:1; Reaction Temperature, 100°C.
(□, EtOH; ○, Water)

Self-catalyzed Esterification Citric Acid Solution
Reaction Conditions: Mole Ratio of Ethanol to Citric acid, 15:1; Reaction Temperature, 110°C.
(■, CA; ●, MEC; ▲, DEC; ×, TEC)

Self-catalyzed Esterification Citric Acid Solution
Reaction Conditions: Mole Ratio of Ethanol to Citric acid, 15:1; Reaction Temperature, 110°C. (□, EtOH; O, Water)

HPLC analysis of reboiler composition from Run 1

HPLC analysis of reboiler composition from Run 2

HPLC analysis of reboiler composition from Run 3

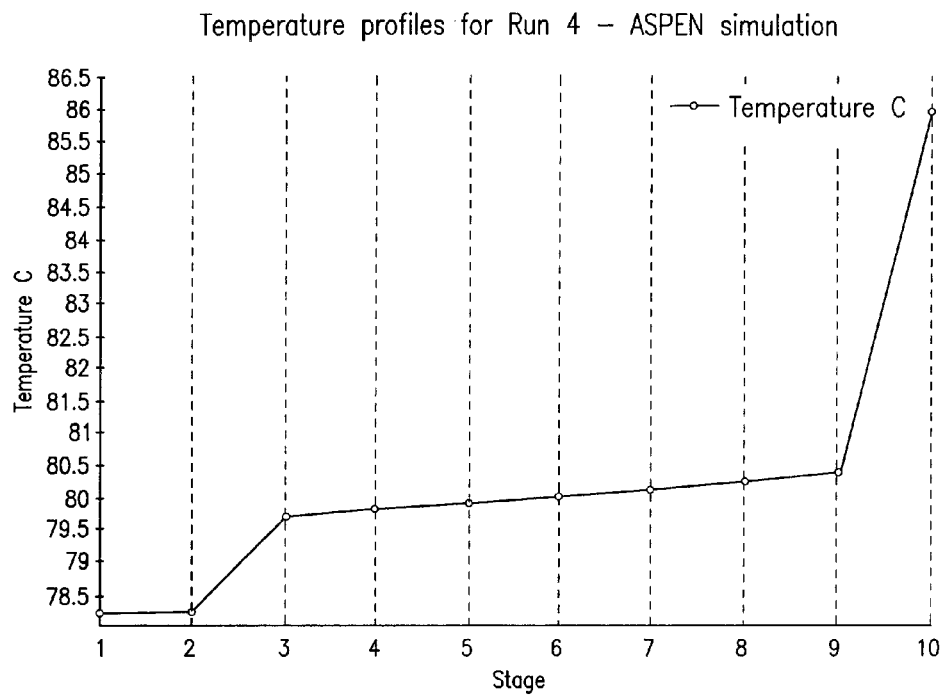

FIG. 33

Different reactive distillation configurations for ASPEN simulations: 1) reactive distillation column with non-reactive rectifying, non-reactive stripping and reactive middle section 2) plug flow pre-reactor, followed by a simple distillation column and reactive distillation column, 3) plug flow pre-reactor followed by reactive distillation column. The reactive section is distinguished by the shaded areas.

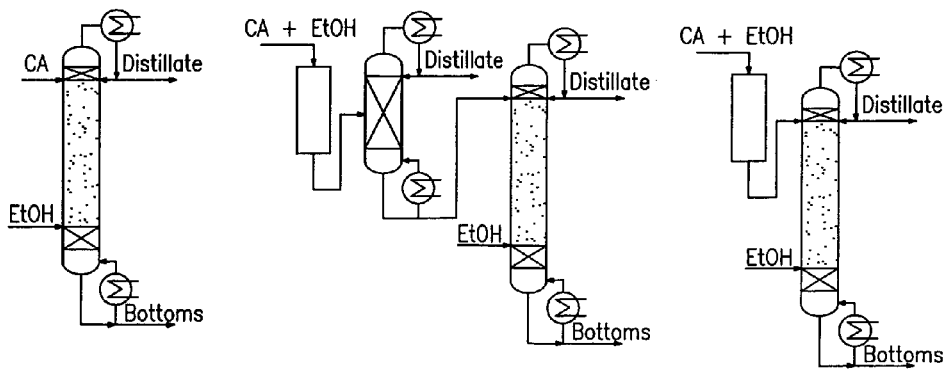

FIG. 34

PROCESS FOR REACTIVE ESTERIFICATION DISTILLATION

CROSS-REFERENCE TO RELATED APPLICATIONS

This application is a continuation-in-part of U.S. application Ser. No. 10/894,307, filed Jul. 19, 2004.

STATEMENT REGARDING FEDERALLY SPONSORED RESEARCH OR DEVELOPMENT

None

BACKGROUND OF THE INVENTION (1) Field of the Invention

The present invention relates generally to a process for the countercurrent, reactive distillation, esterification of organic di- and tri-acids with lower alcohols (C1 to C8) with the available acid groups esterified. Specifically, the present invention relates to citric acid tri-esterification using reactive distillation with the alcohols, particularly ethanol.

(2) Description of the Related Art

There has been considerable interest in the development and use of biorenewable-based chemicals. This interest is fueled by ever-rising global crude oil prices, the increasing desirability to reduce dependence on petroleum-based industries, and potential environmental benefits. Bio-based chemicals are environmentally friendly because they often degrade into benign products, making them prime candidates for replacement of petroleum-based products. The esters of bio-based organic acids fall into the category of benign or "green" solvents and are promising replacements for halogenated petroleum-based solvents in a wide variety of uses.

Citric acid can be esterified with alcohols such as ethanol and n-butanol to yield triethyl citrate and tri-n-butyl citrate, respectively. Both tri-ethyl citrate and tri-n-butyl citrate are used as non-toxic plasticizers in toys, medical products (e.g. as enteric coatings for controlled release drug delivery systems), printing ink coatings, cosmetics, etc. These plasticizers are suitable as food additives such as whipping agents for dried egg whites, food flavorings, or food packaging materials. Citrate esters rapidly metabolize in the body via liver and blood serum enzymes to liberate the citrate ion which is disposed of through the usual biochemical pathways.

Tri-ethyl citrate is a water soluble plasticizer while tri-butyl citrate is a water insoluble plasticizer. The global market for citrate plasticizers has been estimated at around 11 billion pounds per year and according to 2003 statistical data, the U.S. share of this market is 2.4 billion pounds.

Citric acid is a tri-basic acid. Upon esterification with an alcohol such as ethanol or n-butanol, it forms, through a series of reactions, a mixture of mono-alkyl, di-alkyl and tri-alkyl citrates as shown in FIG. 1.

The esterification of citric acid is an equilibrium-limited process. Such processes, when carried out in conventional reactors, suffer from limited conversion. To overcome this equilibrium limitation, continuous removal of one of the products of the reaction mixture is essential in order to drive the reaction to completion. One technique available for doing so is through the use of continuous reactive distillation.

There are other di- and tri-organic acids. These include succinic acid, maleic acid, glutaric acid, adipic acid, malonic acid and pimelic acid which are diacids. It also applies to other tri-acids which need to be esterified.

Reactive Distillation

Reactive distillation (RD) is a multifunctional process where chemical reaction and distillation occur simultaneously in a single vessel. The numerous advantages arising from the synergistic interaction of unit operations in a single unit over the conventional, sequential operation of a reactor followed by a distillation column include overcoming limitations of some equilibrium-limited chemical reactions (as in methyl acetate and MTBE production), improved selectivity by removal of the products from the reaction zone, thereby limiting by-product formation, "reacting away" some of the azeotropes present in conventional distillation processes, and utilizing the exothermic heat of reaction for vaporization and avoidance of hot spot formation. These potential advantages of reactive distillation lead to lower capital and operating costs as well as reduced environmental impact. The major shortcomings of reactive distillation are requirements for much greater complexity in design and process control, often involving multiple steady states, and high process non-linearity due to the strong interaction between process variables. The operating window of reactive distillation processes has to be compatible with the thermal stability of the catalyst in order to ensure a long catalyst life since frequent catalyst change over is an expensive proposition. Reactive distillation requires a significantly greater research effort, in both experimental and in mathematical modeling, in order to develop a feasible process.

Reactive distillation was first reported by Backhaus (Backhaus A. A. Continuous Process for the manufacture of Esters. U.S. Pat. No. 1,400,849 (1921)). The subject has witnessed an explosion of interest in the last ten years since its commercial application to MTBE and methyl acetate production. Reviews on reactive distillation are available from Sharma and Mahajani (Sharma, M. M., Mahajani, S. M. Industrial Application of Reactive Distillation in *Reactive Distillation* Edited by Sundmacher K. and Kienle A., Wiley VCH, Germany, 1 (2003)); Mahajani and Chopade (Mahajani, S. M.; Chopade, S. P. Reactive Distillation: Process of Commercial Importance. *Encyclopedia of Separation Science* Edited by Wilson I. D., Edlard T. R., Poole C. A. and M. Cooke, Academic Press, London UK, 4075 (2001)), Taylor and Krishna (Taylor, R., et al., Modelling Reactive Distillation. *Chem. Eng. Sci.*, 55, 5183 (2000); and Modelling of Homogeneous and heterogeneous Reactive Distillation Processes, Chapter 9 in "Reactive Distillation" Editors: K. Sundmacher, A. Kienle, pp. 217-240, Wiley-VCH, Mannheim (2003) and Hiwale et al (Hiwale, R. S., et al., Industrial Application of Reactive Distillation: Recent Trends. *Int. J. of Chem. React. Eng.*, 2, Review R1 (2004)). Reactive distillation in the presence of solid acid catalyst, also commonly referred to as catalytic distillation, has come a long way since its inception by Spes (Spes, H., Katalytische Reaktionen in Ionenaustaucherkolonnen unter Verschiebung des chemische Geleichgewichts. *Chemiker Atg/Chemische Apparatur*, 90, 443-446 (1966)). Industrially applied reactive distillation processes are rather limited in number currently, especially in comparison to potential applications (Stankiewicz and Moulijn, 2000).

The degree of complexity in reactive distillation processes increases with use of solid catalysts, but the development of modern structured column packings makes the use of such catalysts viable. Katapak-S structured packing (Sulzer), used in this invention, is a well-known and highly versatile packing consisting of vertically-oriented enclosures filled with catalyst particles. Fluid dynamic properties and use of Katapak-S in reactive distillation systems have been described in the open literature by Moritz and Hasse (*Chem. Eng. Sci.* 54, 1367-1374 (1999), Hanika et al (*Chem. Eng. Sci.* 54, 5205-

5209 (1999), Van Baten et al (*Catalysis Today*, 69, 371-377 (2001), Gotze et al (*Catalysis Today*, 69, 201-208 (2001), Van Baten and Krishna (*Catalysis Today*, 69, 371-377 (2001), Smejkal et al (*Chem. Eng. Sci.*, 56, 365-370 (2001), Ratheesh and Kannan (*Chem. Eng. Ji.*, 104, 45-54 (2004), Kolodziej et al (*Chem. Eng. Proc.*, 43, 457-464 (2004), Schmitt et al (*Chem. Eng. Proc.*, 43, 397-409 (2004) and Schmitt et al (*Chem. Eng. Proc.* 44, 677-685 (2005).

Citric Acid Esterification Via Reactive Distillation

Synthesis of organic acid esters by reactive distillation is well established, but in most applications the ester has either the highest volatility of the reagents present (e.g., methyl acetate) or the lowest volatility, with water as the most volatile component (Schmitt et al., *Chem. Eng. Proc.* 43, 397-409 (2004)). In these cases, recovery of 100% pure ester is straightforward via optimization of column operating conditions. Tri-ethyl citrate production via reactive distillation does not fit into either of these categories. Formation of tri-ethyl citrate proceeds through a series of reactions yielding mono- and di-ethyl citrate as intermediate products. Since tri-ethyl citrate has a volatility that is lower than ethanol and water but higher than citric acid, mono- and di-ethyl citrates (those are essentially non-volatile). Therefore, it is only possible to isolate the pure product if complete conversion of citric acid and the intermediate products mono-ethyl citrate and di-ethyl citrate are achieved within the reactive distillation column. The primary challenge is therefore to achieve sufficiently rapid esterification kinetics so as to ensure complete conversion to the desired product triethyl citrate. Example of previous experimental work on similar esterification systems has been described by Bock et al (*Chem. Eng. Prog.* 36, 101-109 (1997)) for the synthesis of isopropyl myristate, and in Applicants' parent application Ser. No. 10/894,307, filed Jul. 19, 2004 for synthesis of ethyl lactate which is incorporated herein in its entirety. In both of these systems excess ethanol is used, which distills along with water as the top product. Omota et al (*Chem. Eng. Sci.*, 58, 3159-3174 (2003)) have described a reactive distillation system for synthesis of fatty esters where an immiscible two-phase water-alcohol mixture distills as the top product.

Prior information on the kinetics of citric acid esterification with ethanol or n-butanol is confined to mainly the Chinese and German patent literature. Joerg et al. (Application WO 2003008369 A1 (2003)) describes a process for synthesis of tri-ethyl citrate by a three stage batch process. Tao (Tao, X., Huazue Shijie, 39(6), 302-304 (1998)) discusses the synthesis of tri-ethyl citrate in the presence of p-toluenesulfonic acid as catalyst and removal of the formed water. Frappier et al (WO 9851657 (1998)) discusses a process for synthesis of tri-ethyl citrate from citric acid containing fermentation broths. Some of the recent references on synthesis of tri-butyl citrate have been described by Nong (Nong, L., Synthesis of Tributyl Citrate with Aluminum Phosphotungstate Supported on activated Carbon. Jingxi Huagong Zhongjianti, 34, 50-52 (2004)) using an aluminum phosphotungstate supported catalyst, Shi et al (Synthesis of tributyl citrate catalyzed by solid superacid $S_2O_8^{2-}/TiO_2/SiO_2$. Yingyong Huagong Keji, 33, 41-43 (2004)) using a solid super acid catalyst, Zheng et al (Synthesis of tributyl citrate catalyzed by tetrabutyl titanate. 34, 28-30 (2004)) using tetrabutyl titanate, Deng et al. (The synthesis of tributyl citrate catalyzed by sodium hydrogen sulfate. Jingxi Huagong Zhongjianti, 33, 49-50 (2003)) using sodium hydrogen sulfate, Song et al. (Catalytic synthesis of tri-n-butyl citrate with aluminophosphate solid acid catalyst. 11, 6-8 (2003)) using an aluminophosphate solid acid catalyst, Liu et al (Catalytic synthesis of tri-butyl citrate with dealuminated USY zeolite. 11, 175-177 (2003)) using a dealuminated USY Zeolite, Meng et al. (Synthesis of tributyl citrate catalyzed by the nanosolid superacid $SO_4^{2-}/Fe_2O_3$. Hebei Shifan Daxue Xuebao, Ziran Kexueban. 27, 64-66 (2003)) using a nanosolid superacid $SO_4^{2-}/Fe_2O_3$, Zhao et al. (Synthesis of tributyl citrate catalyzed by complex solid superacid $WO_3/TiO_2/SO_4^{2-}$. Huagong Keji. 10(5), 11-13 (2002)) using $WO_3/TiO_2/SO_4^{2-}$ super acid catalyst, Meng et al. (Synthesis of tributyl citrate with p-toluene sulfonic acid catalyst. Hecheng Huaxue Ji Suliao, 19(2), 16-18 (2002)) using p-toluenesulfonic acid catalyst and Fu et al. (Synthesis of tributyl citrate catalyzed by $SO_4^{2-}$ modified zirconium cross-linked solid clay. Jingzi Huagong. 19(1), 28-31 (2002)) using $SO_4^{2-}$ modified zirconium crosslinked clay catalyst.

U.S. Pat. No. 5,008,046 to Bremus et al. describes a reactive distillation process using a column with plate type column with an acid catalyst under pressure. U.S. Pat. No. 5,536,856 to Harrison et al. describes a similar column wherein resin acid catalyst particles were supported by a tray on the column. The use of columns with trays is quite expensive.

While the related art teaches organic acid esterification processes, there still exists a need for improved continuous processes for di- and tri-organic acid, particularly citric acid esterification.

OBJECTS

Therefore, it is an object of the present invention to provide an improved process for the continuous production of di- and tri-substituted organic acid esters in a single column using reactive distillation. It is particularly an object of the present invention to provide a process for producing triethyl citrate.

These and other objects will become increasingly apparent by reference to the following description.

SUMMARY OF THE INVENTION

The present invention relates to a process for the continuous esterification of an organic acid with two or three acid groups to produce an organic acid di- or tri-ester with the available acid groups esterified in a vertical column by reactive distillation comprising: (a) feeding a mixture comprising the organic acid with the two or three acid groups and containing between 3 to 8 carbon atoms as an aqueous or alcoholic solution into an upper port of the column and an alcohol containing 1 to 8 carbon atoms into a lower port of the column; (b) contacting in a reactive distillation the organic acid and the alcohol in countercurrent flow in a reaction zone between the ports at a temperature which reacts the organic acid and the alcohol over an insoluble acid catalyst mounted in structured packing elements and supported as a single unit of the elements in the column within the reaction zone to form the organic acid ester; (c) removing vaporized unreacted alcohol and water from the top of the column; and (d) collecting a product comprising the organic acid ester from the bottom of the column, wherein the organic acid ester formed is reboiled by a heat exchanger at the bottom of the column. Preferably the alcohol in step (c) is recovered and recycled into the lower port of the column.

The present invention also relates to a process for the continuous esterification of citric acid to produce a citric acid tri-ester in a vertical column by reactive distillation comprising: (a) feeding a mixture comprising the citric acid as an aqueous or alcoholic solution into an upper port of the column and an alcohol containing 1 to 8 carbon atoms into a lower port of the column; (b) contacting in a reactive distillation the citric acid and the alcohol in countercurrent flow in a reaction zone between the ports at a temperature which reacts the citric acid and the alcohol over an insoluble acid catalyst mounted in structured packing elements and supported in the column within the reaction zone to form the citric acid ester; (c) removing vaporized unreated alcohol and water from the top of the column; and (d) collecting a product comprising the citric acid ester from the bottom of the column, wherein the citric acid ester is reboiled by a heat exchanger at the bottom of the column. Preferably the alcohol is recovered and recycled into the lower port of the column. Preferably the insoluble acid catalyst is an acidic ion exchange resin. Preferably the feeding of the alcohol relative to the citric acid is such that a molar ratio of alcohol to citric acid is maintained between about 3 to about 40. Preferably the feeding of the alcohol relative to the feeding of the citric acid is such that the percentage of citric acid conversion to a tri-ester is greater than 50 percent.

The present invention also relates to a process for the continuous esterification of an organic acid with two or three acid groups to produce an organic acid di- or tri-ester with the available acid groups esterified in a single vertical column by reactive distillation comprising:

(a) feeding a mixture of the organic acid containing about 20 to 90% alcohol containing 1 to 8 carbon atoms into an upper port of the column and the same alcohol into a lower port of the column; (b) contacting in a reactive distillation the organic acid and the alcohol in countercurrent flow in a reaction zone between the ports at a temperature which reacts the organic acid and the alcohol over an insoluble acid catalyst mounted in structured packing elements and supported as a single unit of the elements in the column within the reaction zone to form the organic acid ester; (c) removing vaporized unreacted alcohol and water from the top of the column; and (d) collecting a product comprising the organic acid ester from the bottom of the column, wherein the organic acid ester formed is partially reboiled by a heat exchanger at the bottom of the column. Preferably the alcohol is recovered and recycled into the lower port of the column.

The present invention also relates to a process for the continuous esterification of citric acid to produce a citric acid ester in a single vertical column by reactive distillation comprising: (a) feeding a mixture of citric acid containing about 50 to 90% alcohol containing 1 to 8 carbon atoms into an upper port of the column; (b) contacting in a reactive distillation the organic acid and the alcohol in countercurrent flow in a reaction zone between the ports at a temperature which reacts the organic acid and the alcohol over an insoluble acid catalyst mounted in structured packing elements and supported as a single unit of the elements in the column within the reaction zone to form the organic acid ester; (c) removing vaporized unreacted alcohol and water from the top of the column; and (d) collecting a product comprising the organic acid ester from the bottom of the column, wherein the organic acid ester formed is partially reboiled by a heat exchanger at the bottom of the column. Preferably the alcohol is recovered and recycled into the lower port of the column.

The present invention also relates to a process for the continuous esterification of an organic acid with two or three acid groups to produce an organic acid di- or tri-ester with the available acid groups esterified in a single vertical column by reactive distillation comprising:

(a) feeding a mixture of the organic acid containing about 20 to 90% alcohol containing 1 to 8 carbon atoms into an upper port of the column and the same alcohol into a lower port of the column;

(b) contacting in a reactive distillation the organic acid and the alcohol in countercurrent flow in a reaction zone between the ports at a temperature which reacts the organic acid and the alcohol over an insoluble acid catalyst mounted in structured packing elements and supported as a single unit of the elements in the column within the reaction zone to form the organic acid ester;

(c) removing vaporized unreacted alcohol and water from the top of the column; and (d) collecting a product comprising the organic acid ester from the bottom of the column, wherein the organic acid ester formed is partially reboiled by a heat exchanger at the bottom of the column. Preferably the alcohol is recovered and recycled into the lower port of the column. Preferably the insoluble acid catalyst is an acidic ion exchange resin. Most preferably, the feeding of the alcohol relative to the citric acid is such that a molar ratio of alcohol to citric acid is maintained between about 3 to about 35. Preferably the feeding of the alcohol relative to the feeding of the citric acid is such that the percentage of citric acid conversion to the citric acid tri-ester is greater than 50 percent.

BRIEF DESCRIPTION OF THE DRAWINGS

FIGS. 11A and 11B are graphs showing Reaction Conditions: Mole Ratio of Ethanol to Citric acid, 15:1, Catalyst Loading, 1 wt %, Reaction Temperature, 120° C.

FIGS. 12A and 12B are graphs showing Reaction Conditions: Mole Ratio of Ethanol to Citric acid, 15:1, Catalyst Loading, 3 wt %, Reaction Temperature, 78° C.

FIGS. 19A and 19B are graphs showing Reaction Conditions: Mole Ratio of Ethanol to Citric acid, 15:1, Reaction Temperature, 120° C.

FIGS. 20A and 20B are graphs showing Reaction Conditions: Mole Ratio of Ethanol to Citric acid, 10:1, Reaction Temperature, 120° C.

FIGS. 21A and 21B are graphs showing Reaction Conditions: Mole Ratio of Ethanol to Citric acid, 5:1, Reaction Temperature, 120° C.

FIGS. 23A and 23B are graphs showing Reaction Conditions: Mole Ratio of Ethanol to Citric acid, 15:1, Reaction Temperature, 90° C.

FIG. 33 is a graph showing temperature profiles for Run 2—ASPEN simulation.

FIG. 34 shows different reactive distillation configurations for ASPEN simulations: (1) reactive distillation column with non-reactive rectifying, non-reactive stripping and reactive middle section, 2) plug flow pre-reactor, followed by a simple distillation column and reactive distillation column, 3) plug flow pre-reactor followed by reactive distillation column. The reactive sections are distinguished by the shaded areas.

DETAILED DESCRIPTION OF THE INVENTION

Figure 1:
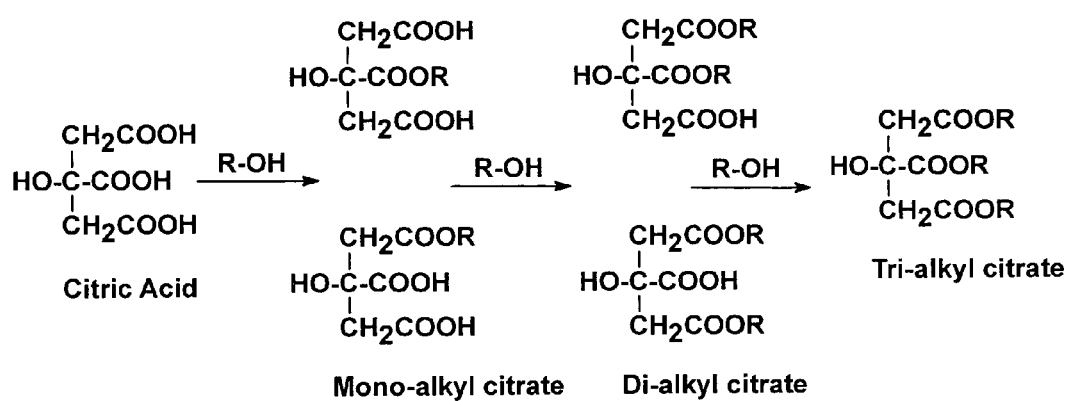
FIG. 1 is a schematic showing esterification of citric acid.

All patents, patent applications, government publications, government regulations, and literature references cited in this specification are hereby incorporated herein by reference in their entirety. In case of conflict the present description, including definitions, will control.

The improved process to make di- and tri-alkyl organic acid esters via reactive distillation is simple, inexpensive, and does not create large quantities of waste. The process is unique and has several advantages that distinguish it from prior methods for making esters. First, the use of a reactive distillation column is less expensive than the conventional batch process because it is a continuous process and because an insoluble acidic ion exchange resin in structured packing elements is used as a catalyst instead of a soluble mineral acid. The ester formation and purification of the product can take place in a single piece of equipment, whereas a conventional process may require up to ten separate pieces of equipment. This reactive distillation process avoids the inherent difficulties associated with membrane processes.

TRIETHYL CITRATE EXAMPLES

Experimental

Materials

Anhydrous citric acid crystals were obtained from Aldrich Chemicals. Absolute ethanol (99% purity) and HPLC grade water were obtained from J. T. Baker. The strong acid cation exchange resin catalyst Amberlyst-15 (Rohm and Hass, Philadelphia, Pa.) was obtained in $H^+$ form and was used without modification. Purity of all chemicals was checked by gas chromatography or HPLC.

Analysis

The presence of citric acid, monoethyl citrate, diethyl citrate and triethyl citrate was first confirmed by GC-MS analysis of their trimethylsilyl (TMS) derivatives. Ethanol and water from reaction samples were analyzed by gas chromatography (Varian 3700 w/TCD detection; 20 ml/min He as a carrier gas) using a packed stainless steel column (3.25 mm×4 m) containing Porapak-Q as the stationary phase. The column temperature program involved initially holding at 140° C. for 2 min, heating to 220° C. at 20° C./min, and holding at 220° C. for 6 min.

Citric acid and its ethyl esters (mono, di and tri) were quantitatively analyzed on a Hewlett-Packard 1090 HPLC using a reversed phase C18 column (Novapak, 3.9 mm×150 mm) held at 40° C. Water/acetonitrile (ACN) mixtures, buffered at pH=1.3, were used as mobile phase (1.0 ml/min) in a gradient mode (0% ACN (t=0) to 60% ACN (t=20 min) to 90% ACN (t=25 min) to 0% ACN (t=28 min)), and species were quantified by UV detection (Hitachi L400H) at a wavelength of 210 nm. Citric acid (CA) and triethyl citrate (TEC) were identified and quantified by comparing HPLC retention time and peak area with their respective calibration standard. Standards for monoethyl citrate (MEC) and diethyl citrate (DEC) could not be obtained commercially. On a mass basis, the response factor values for CA and MEC were found to be the same; therefore MEC and DEC were each assigned the same response factor value as corresponding to TEC. Using these response factor values, the carbon balance for each reaction sample, based on citric acid and its esters, was in the range of ±10%.

Batch Kinetic Experiments

Esterification reactions at 80° C. (the normal boiling point of ethanol) were performed in a $1\times10^{-4}$ $m^3$ jacketed glass reactor equipped with a re-circulating constant temperature oil bath. A spiral coil condenser, open to the atmosphere, was placed on top of the reactor. The glass reactor was equipped with temperature and stirrer speed monitoring devices and a sampling port. In operation, measured quantities of ethanol and citric acid were added to the reactor and heating and stirring were started simultaneously. Once the desired temperature was achieved, usually in about 15 minutes, catalyst (Amberlyst 15 ion exchange resin) was added and stirring speed was increased to 800 rpm. This point in time was considered as the zero reaction time. Samples were withdrawn at specific time intervals and immediately transferred to an ice bath (prior to analysis) in order to ensure that no further reaction took place.

For reaction temperatures of 90° C. and above, esterification was performed in a $1\times10^{-4}$ $m^3$ stainless steel autoclave (5000 Multireactor System, Parr Instrument Co.) equipped with temperature and stirrer speed monitors and a sampling port. In operation, measured quantities of ethanol, citric acid and catalyst were added to the reactor and heating was started with slow stirring. The desired temperature was achieved in about 15 minutes, at which time the stirring rate was increased to 740 rpm. This time was considered as the zero reaction time. Samples were withdrawn at specific time intervals through a cooled metal tube and immediately transferred to an ice bath in order to ensure no further reaction took place before analysis. All samples were analyzed using the method described above.

Reactive Distillation Column

Figure 2:
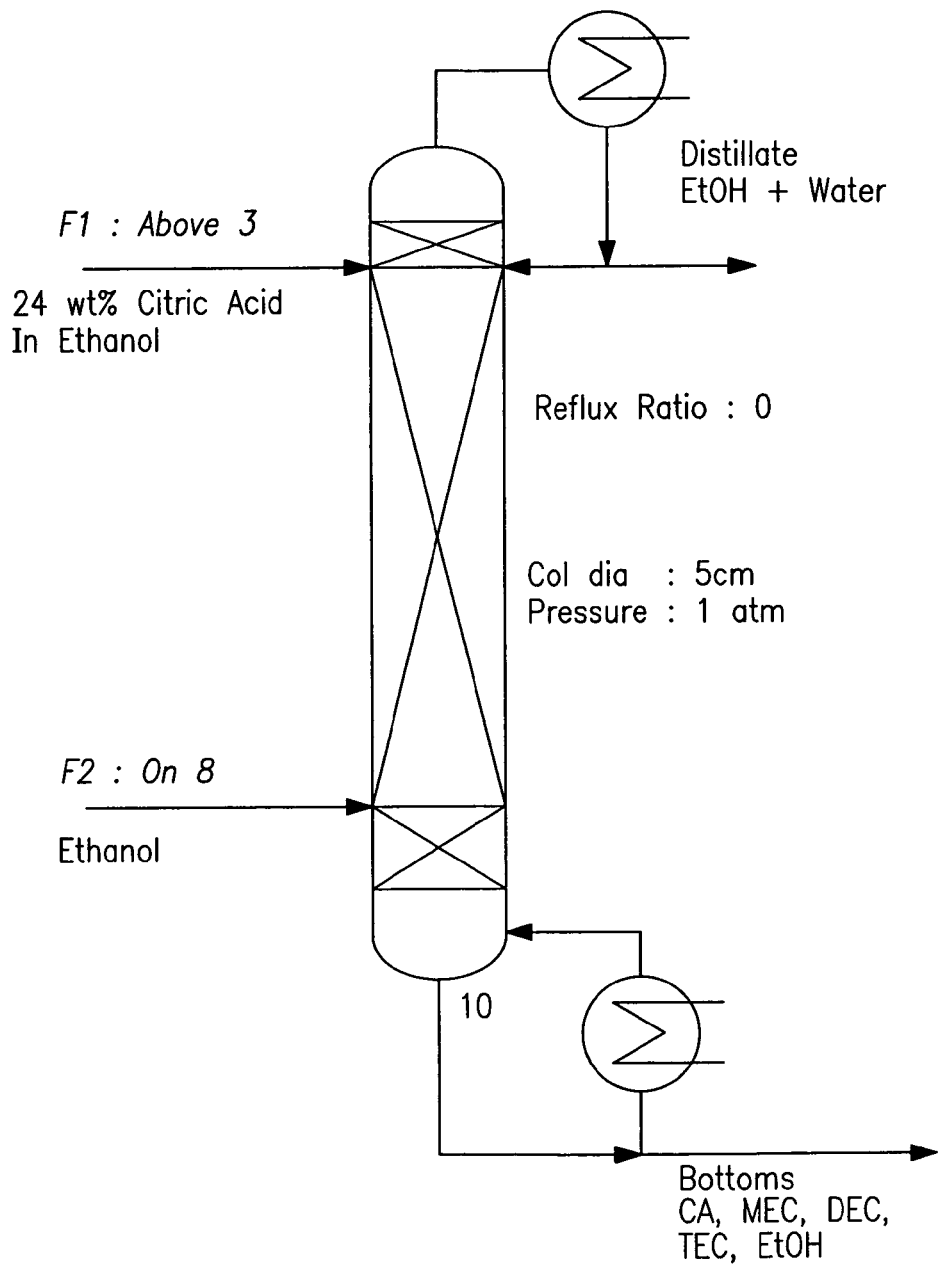
FIG. 2 is a schematic view of a pilot scale reactive distillation column for ethyl citrate synthesis.
Figure 3A:
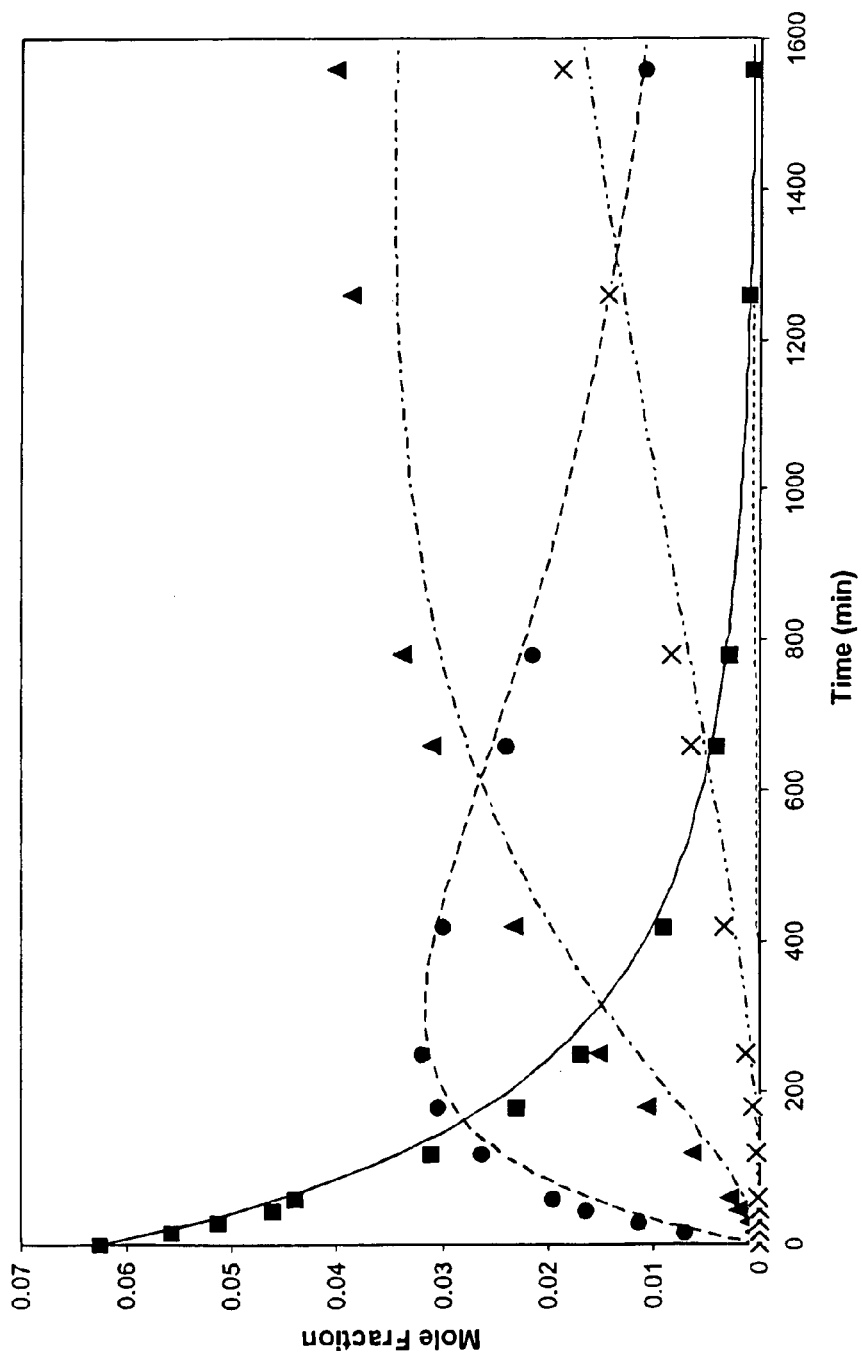
FIGS. 3A and 3B are graphs showing Reaction Conditions: Mole Ratio of Ethanol to Citric acid, 15:1, Catalyst Loading, 5 wt %, Reaction Temperature, 78° C.
Figure 3B:
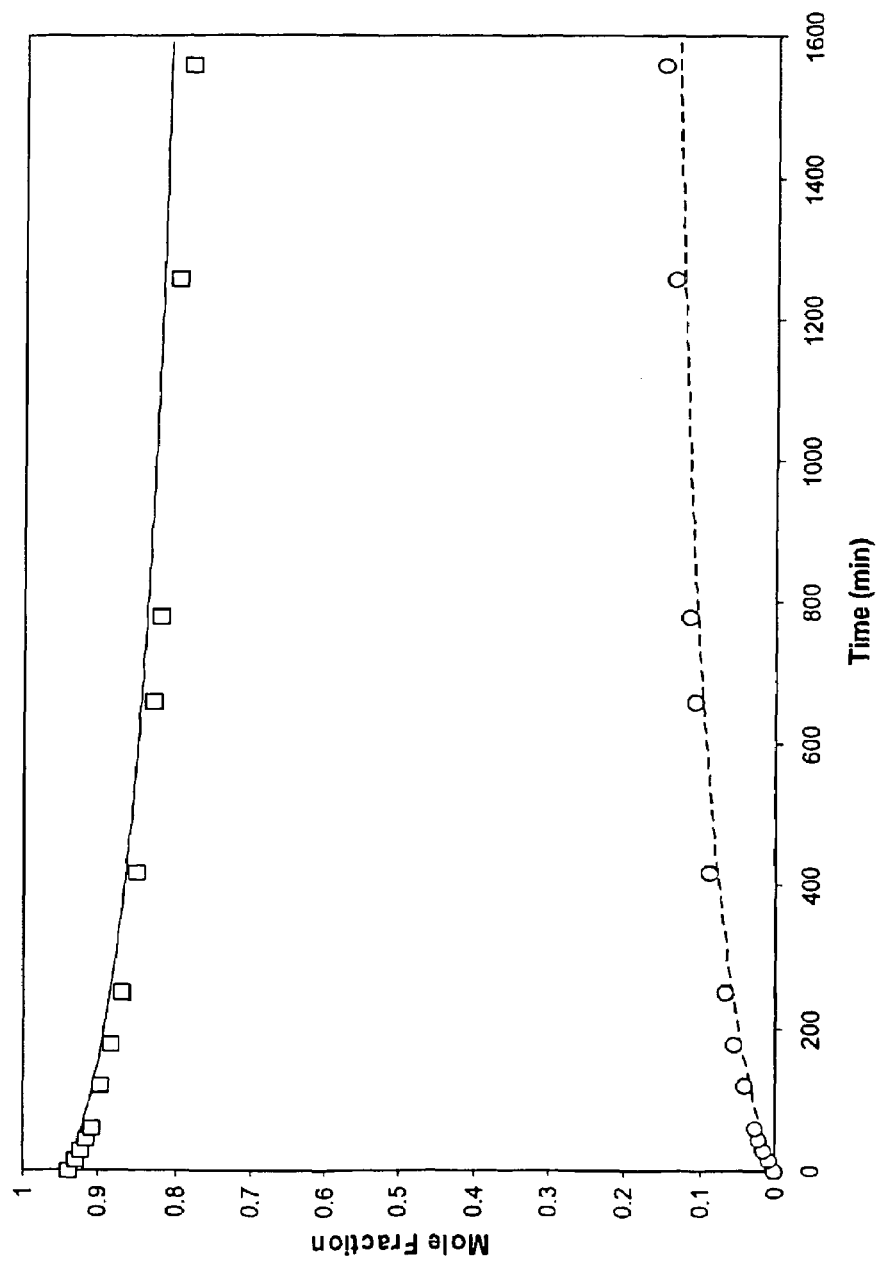
Figure 4A:
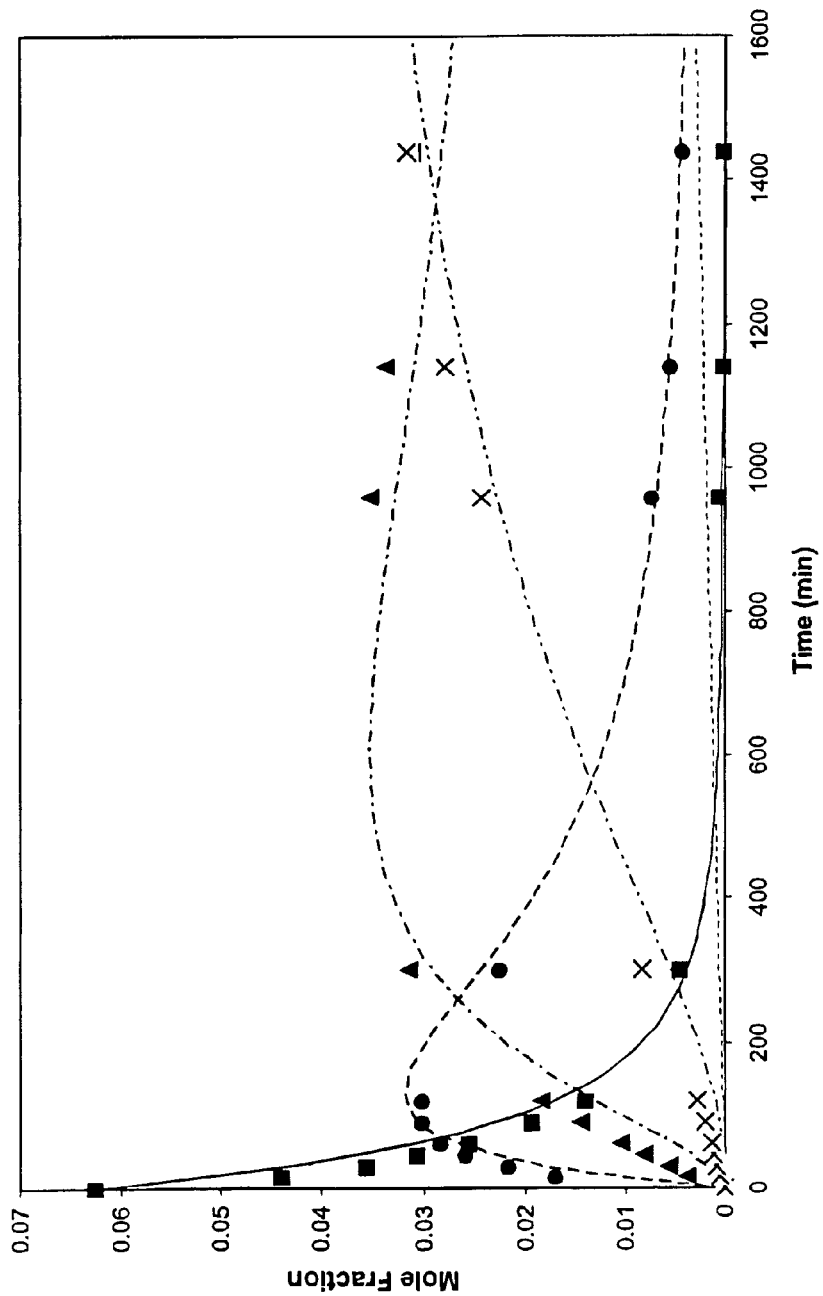
FIGS. 4A and 4B are graphs showing Reaction Conditions: Mole Ratio of Ethanol to Citric acid, 15:1, Catalyst Loading, 5 wt %, Reaction Temperature, 90° C.
Figure 4B:
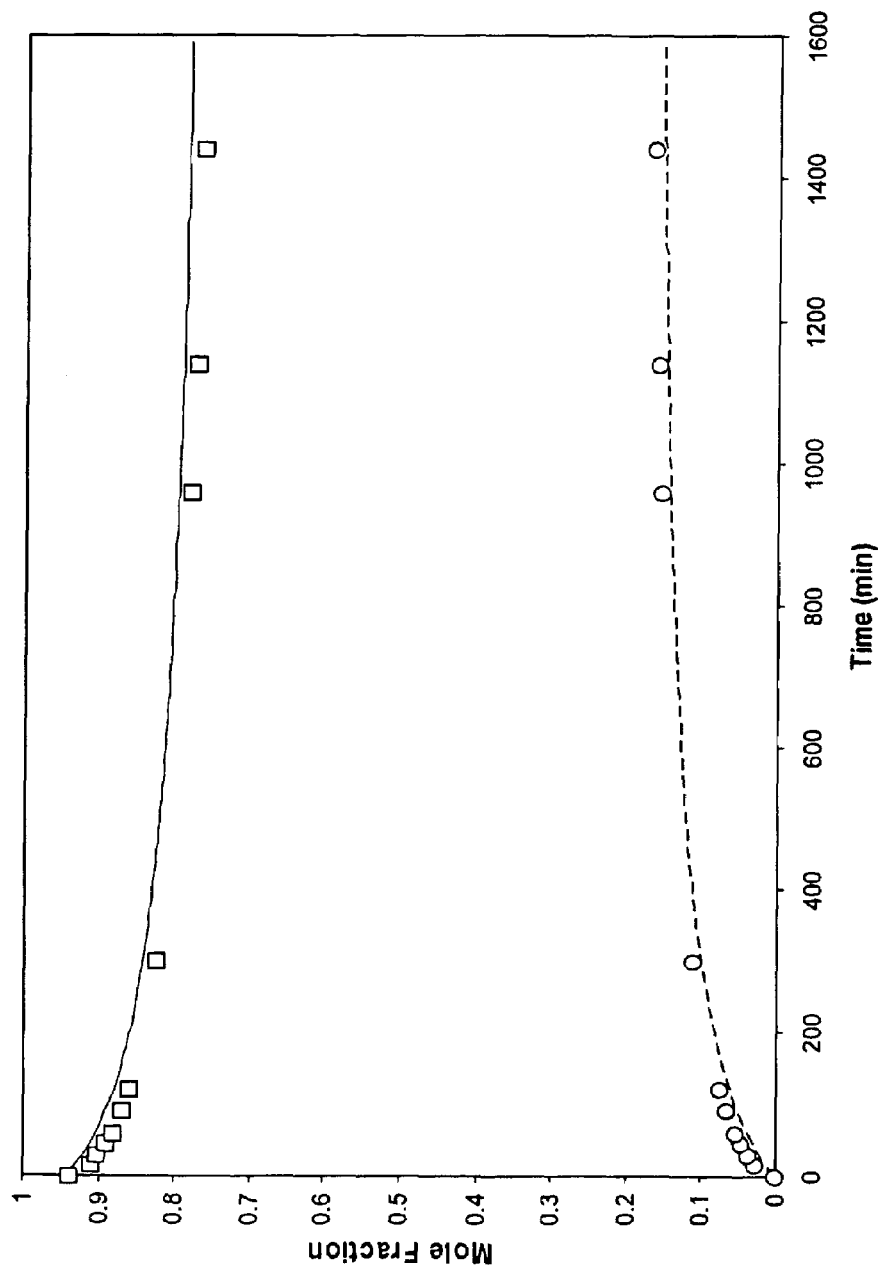
Figure 5A:
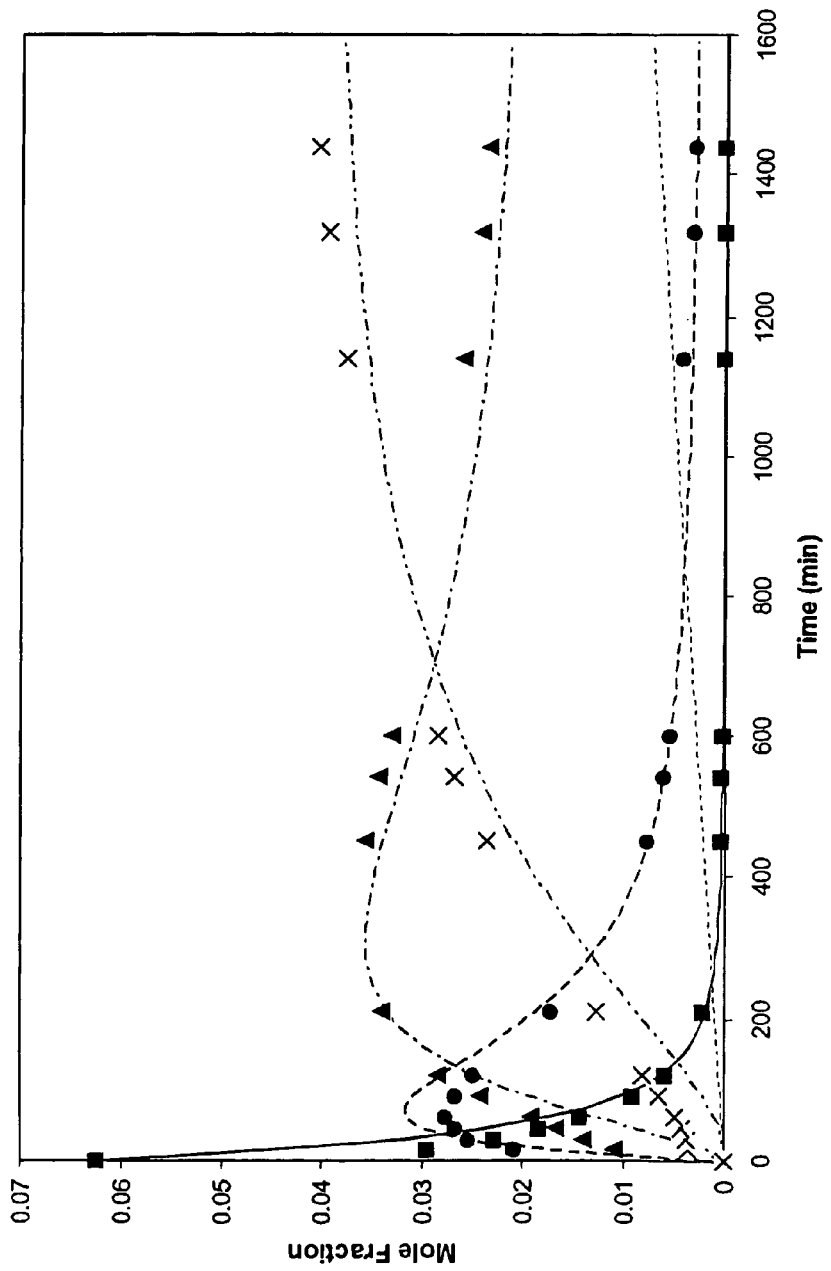
FIGS. 5A and 5B are graphs showing Reaction Conditions: Mole Ratio of Ethanol to Citric acid, 15:1, Catalyst Loading, 5 wt %, Reaction Temperature, 100° C.
Figure 5B:
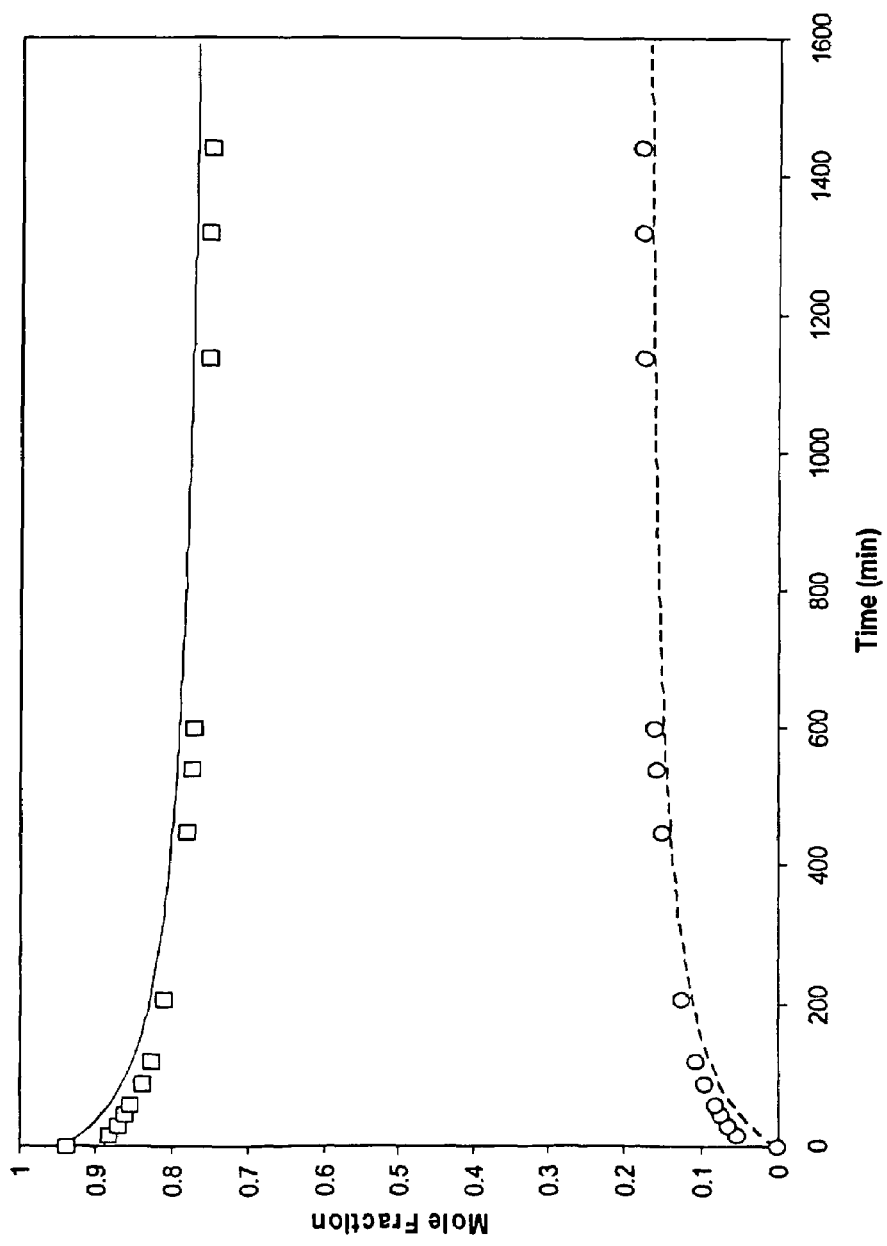
Figure 6A:
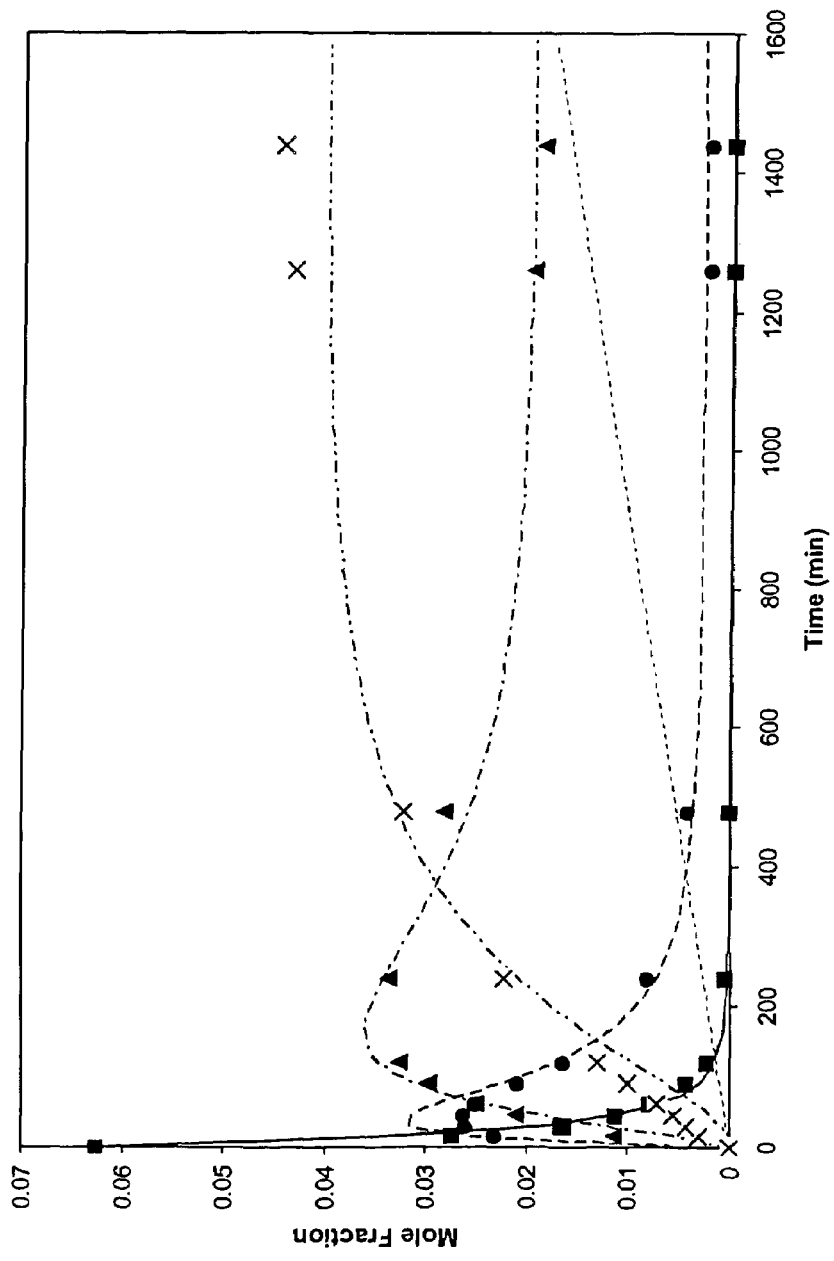
FIGS. 6A and 6B are graphs showing Reaction Conditions: Mole Ratio of Ethanol to Citric acid, 15:1, Catalyst Loading, 5 wt %, Reaction Temperature, 110° C.
Figure 6B:
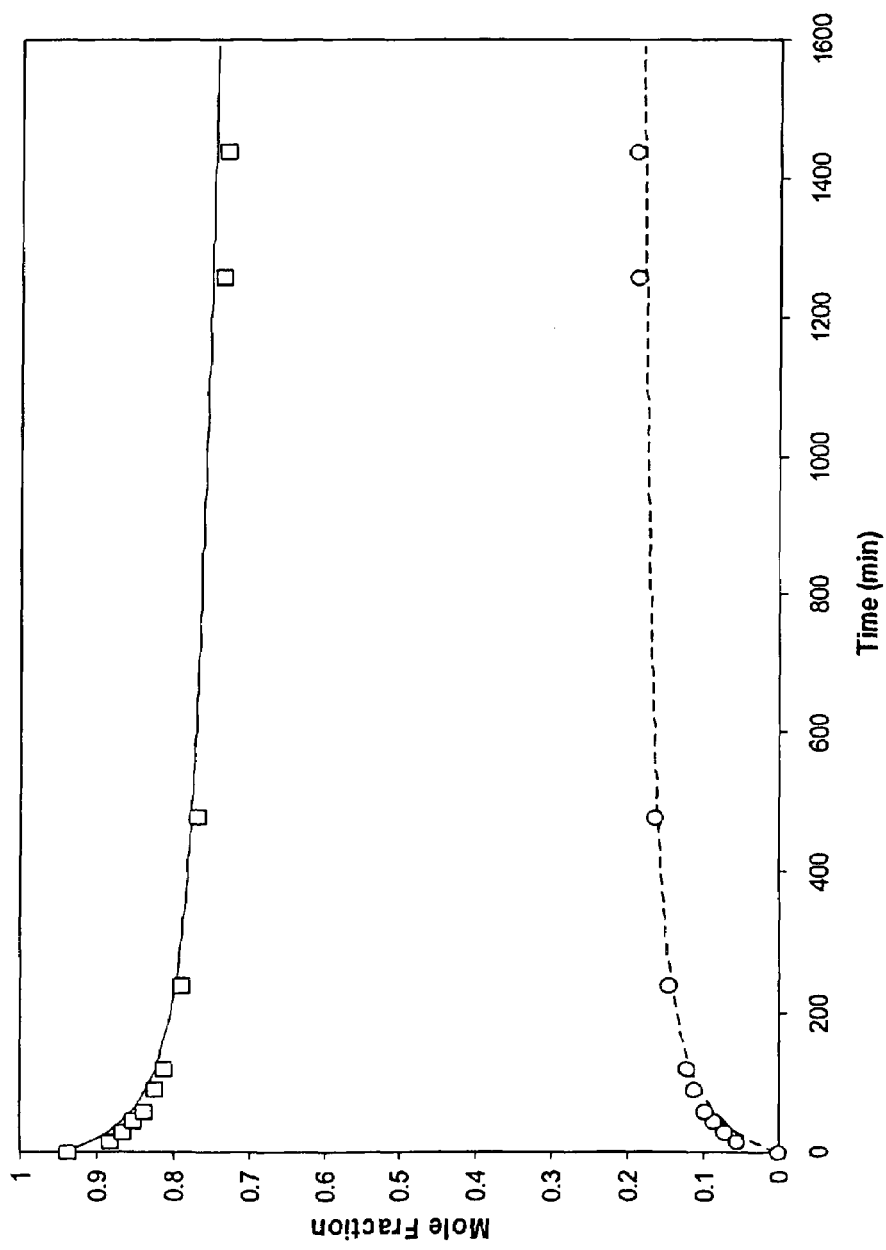
Figure 7A:
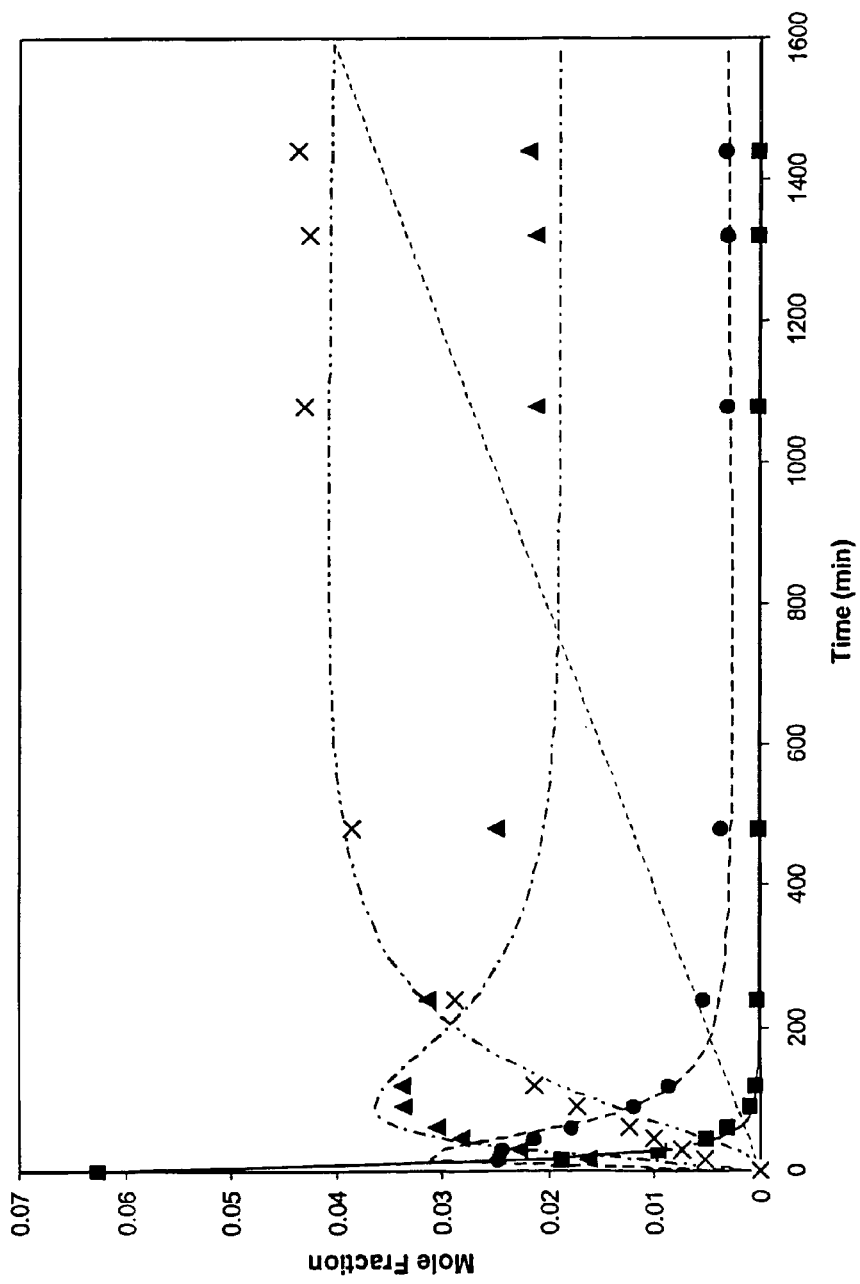
FIGS. 7A and 7B are graphs showing Reaction Conditions: Mole Ratio of Ethanol to Citric acid, 15:1, Catalyst Loading, 5 wt %, Reaction Temperature, 120° C.
Figure 7B:
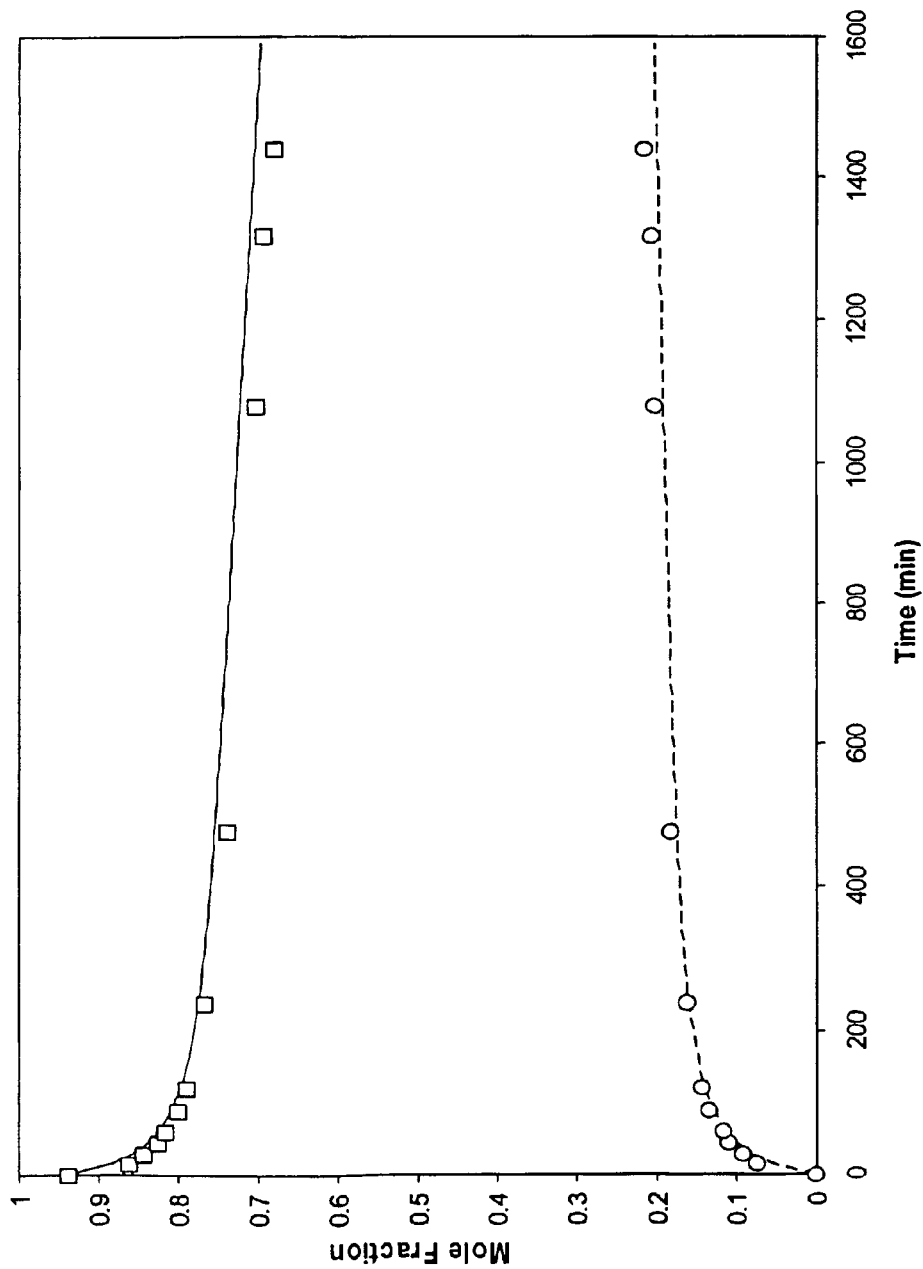
Figure 8A:
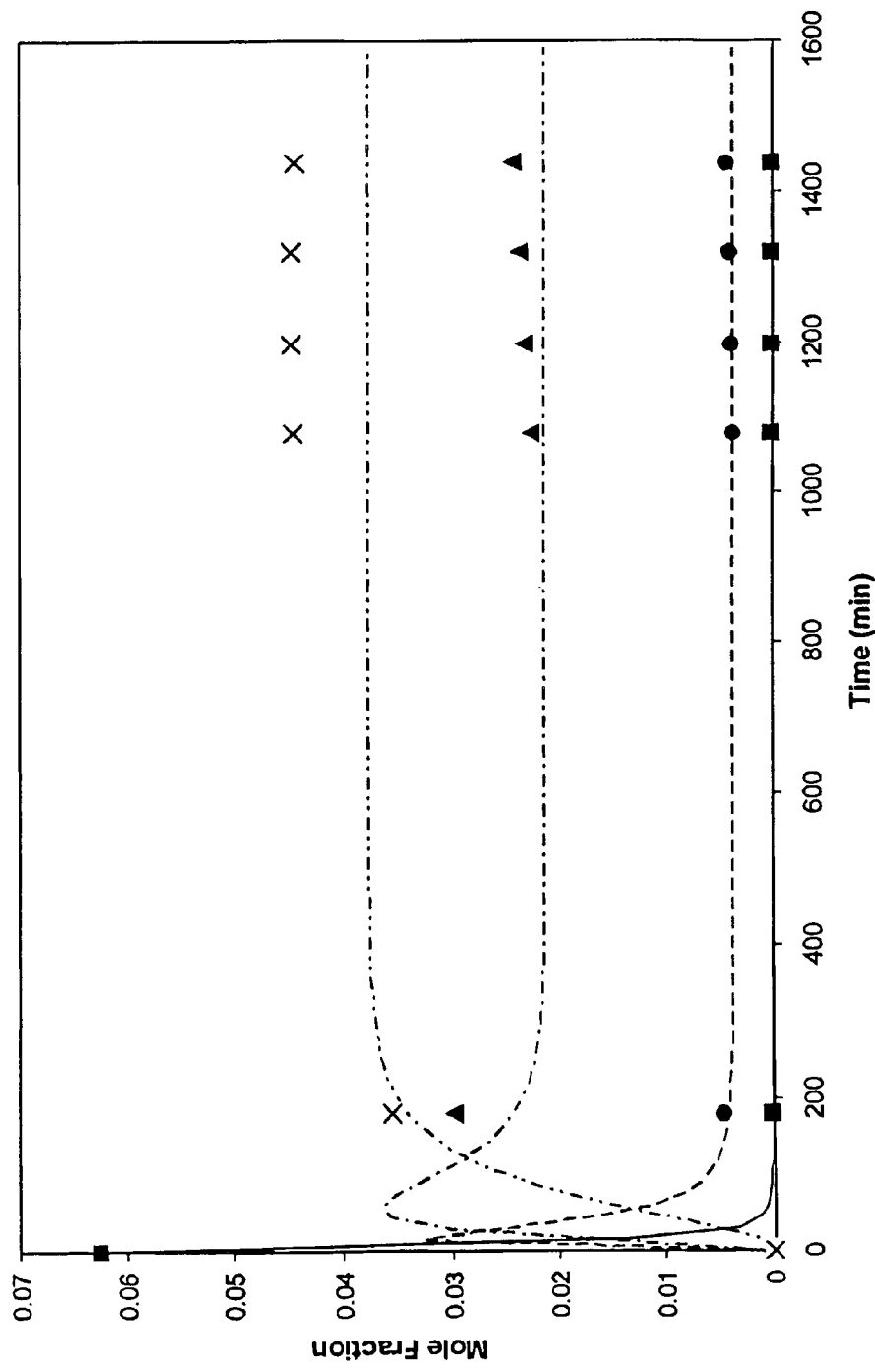
FIGS. 8A and 8B are graphs showing Reaction Conditions: Mole Ratio of Ethanol to Citric acid, 15:1, Catalyst Loading, 10 wt %, Reaction Temperature, 120° C.
Figure 8B:
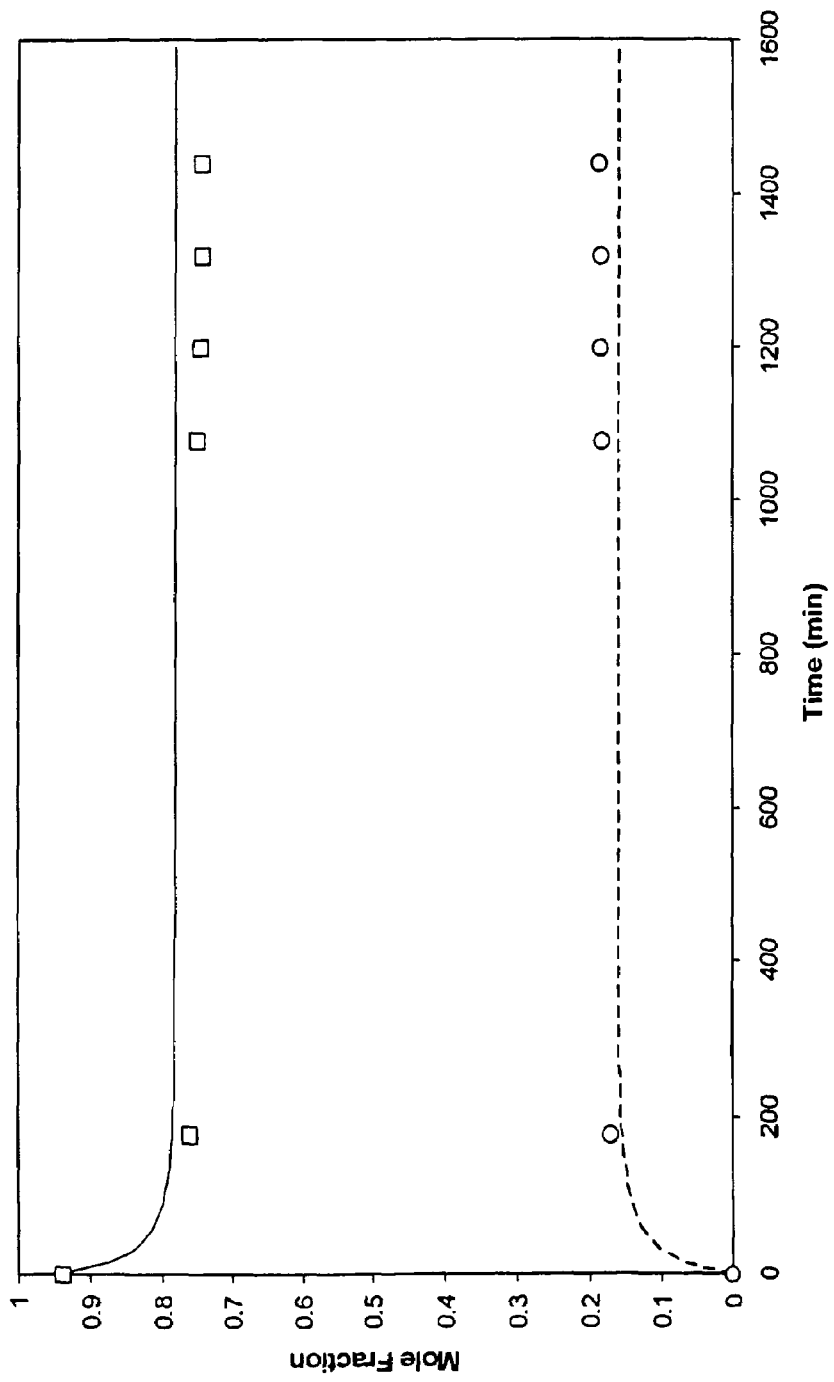
Figure 9A:
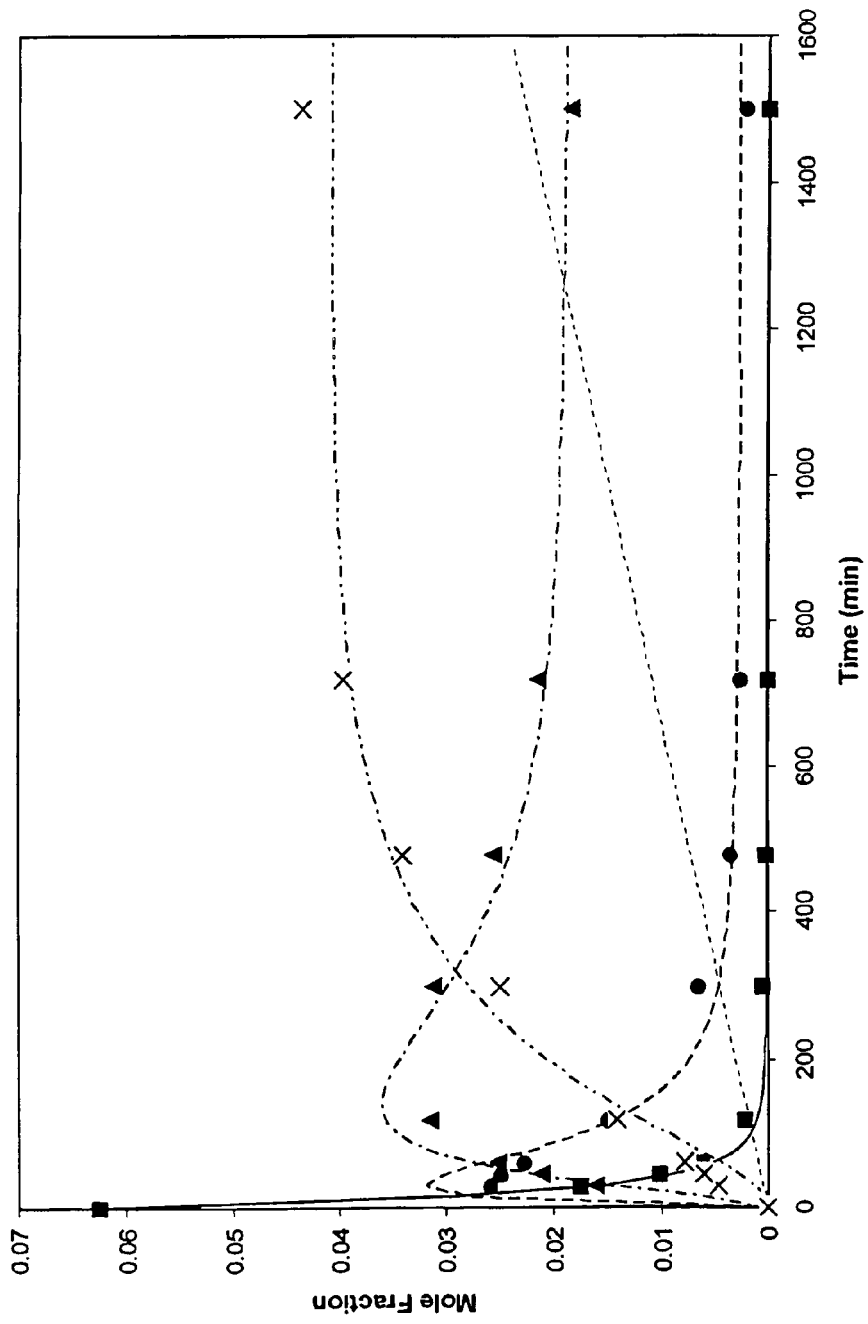
FIGS. 9A and 9B are graphs showing Reaction Conditions: Mole Ratio of Ethanol to Citric acid, 15:1, Catalyst Loading, 3 wt %, Reaction Temperature, 120° C.
Figure 9B:
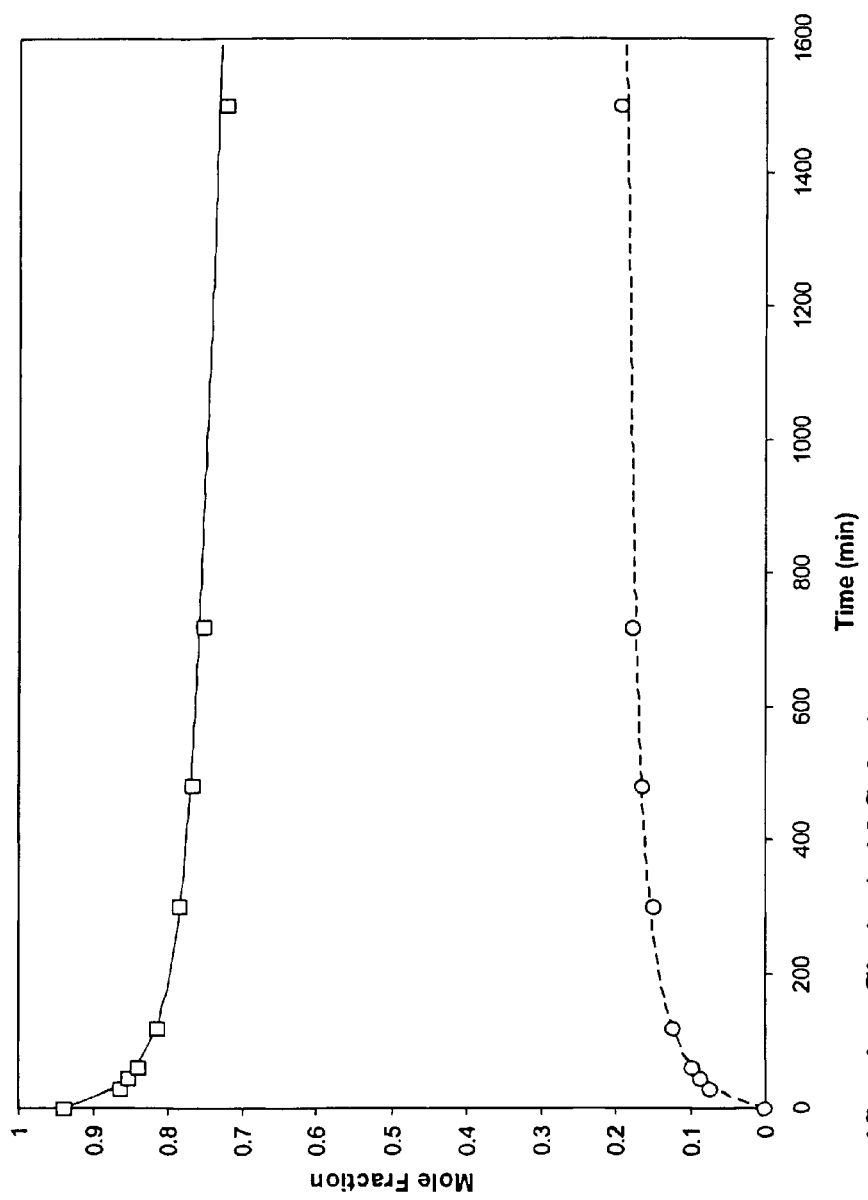
Figure 10A:
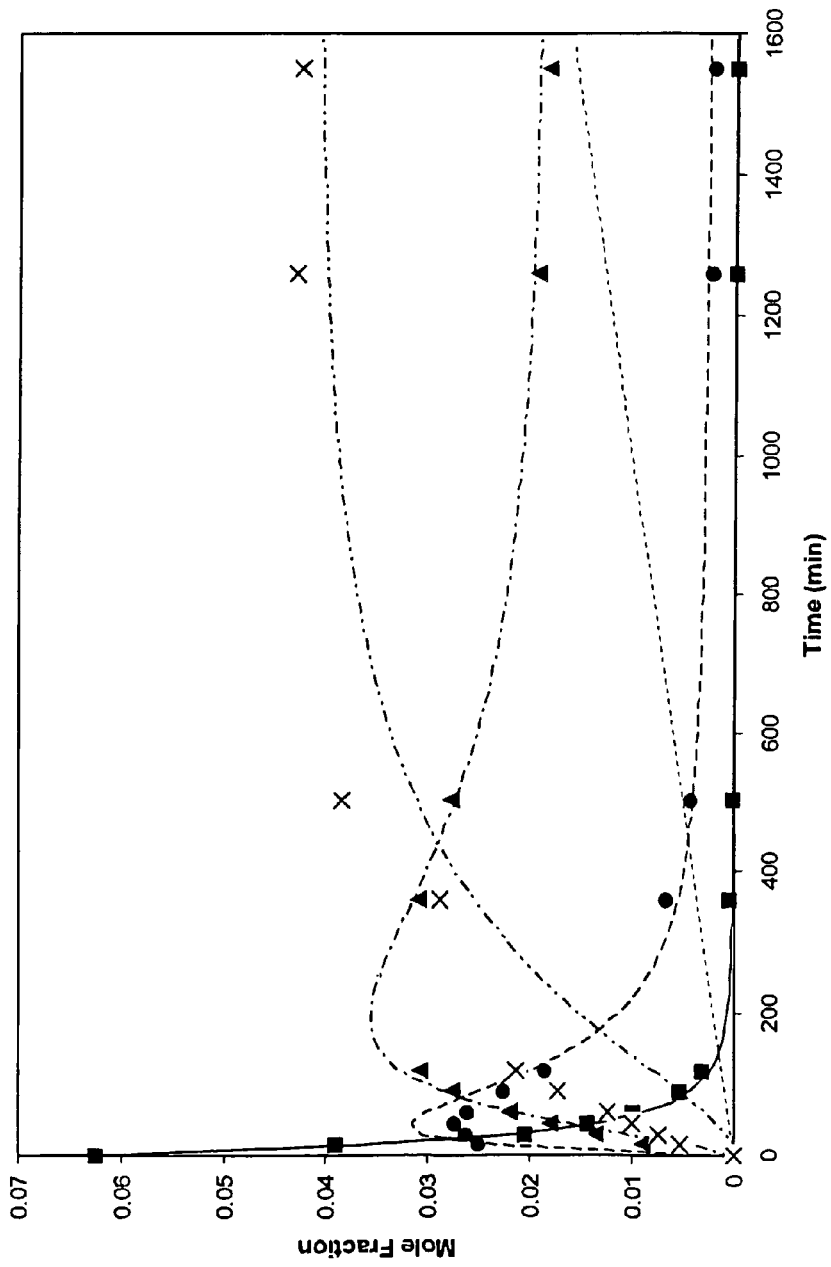
FIGS. 10A and 10B are graphs showing Reaction Conditions: Mole Ratio of Ethanol to Citric acid, 15:1, Catalyst Loading, 2 wt %, Reaction Temperature, 120° C.
Figure 10B:
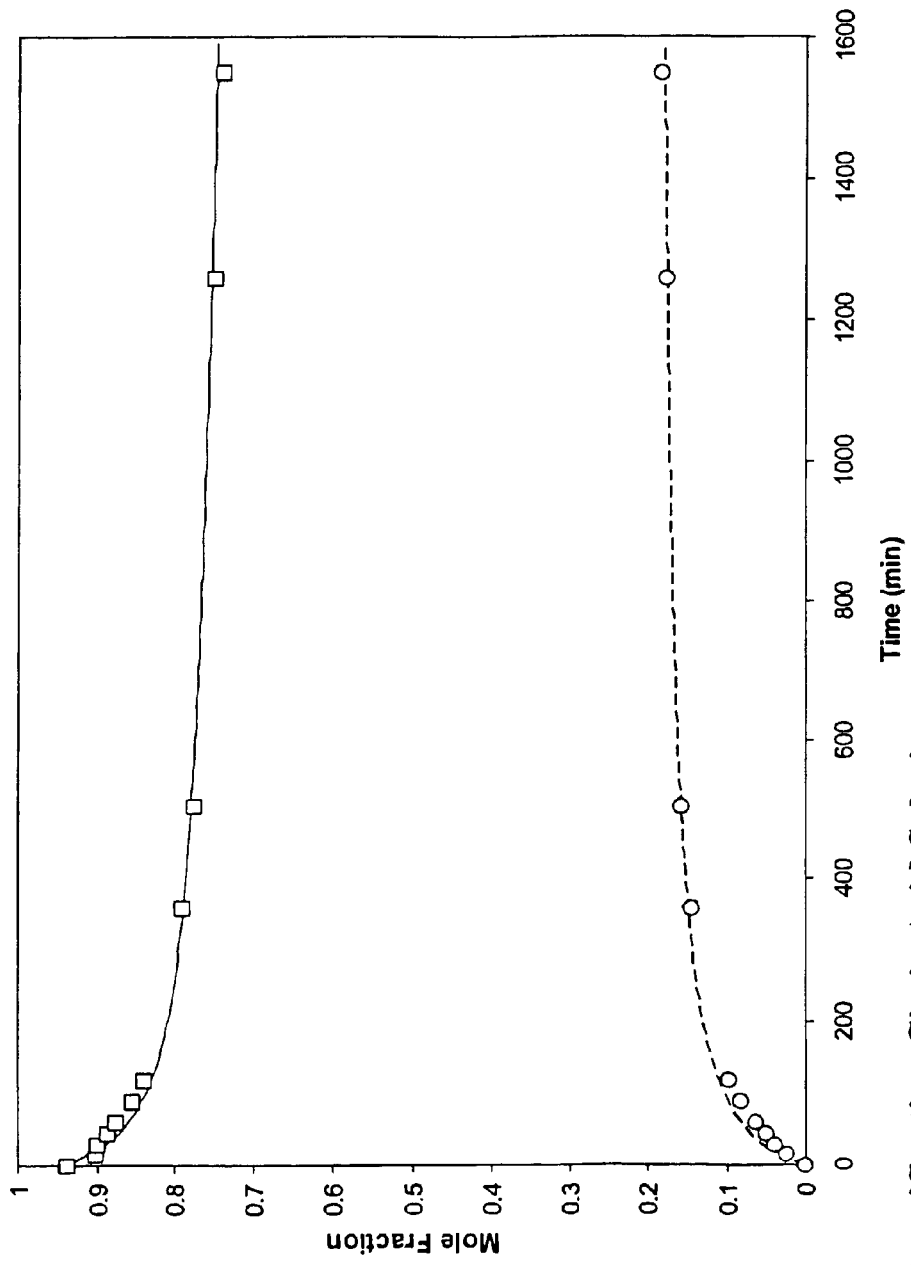
Figure 11A:
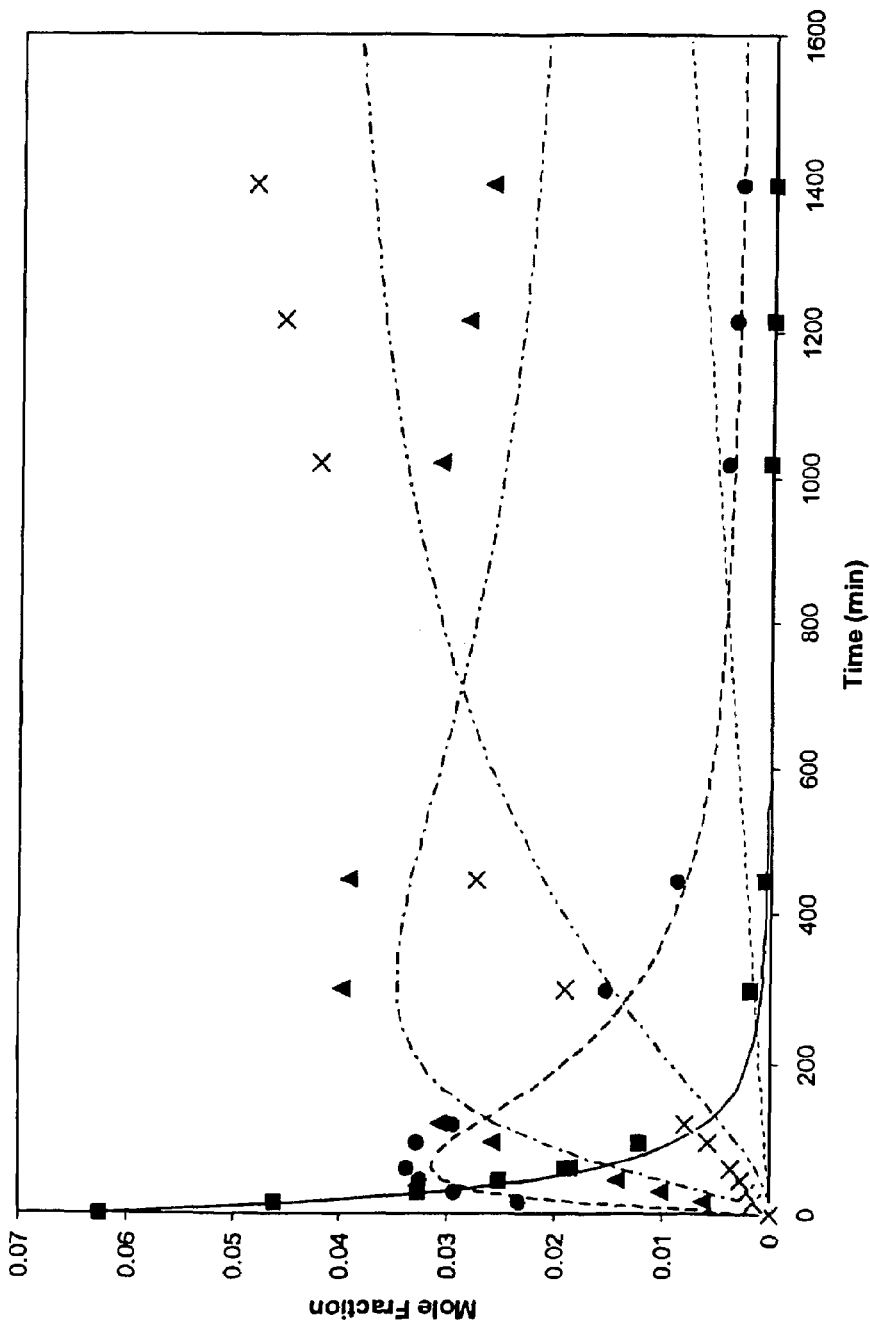
Figure 12B:
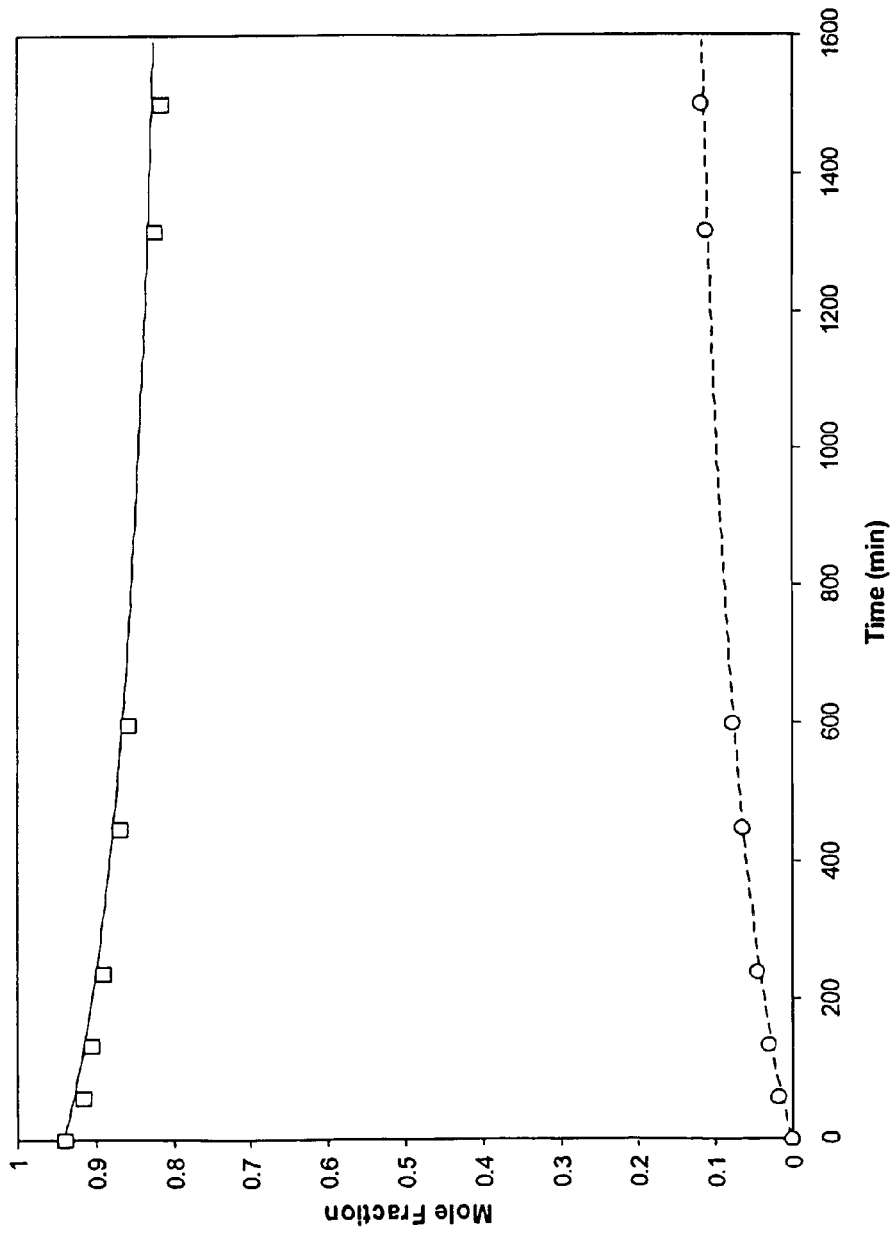
Figure 13A:
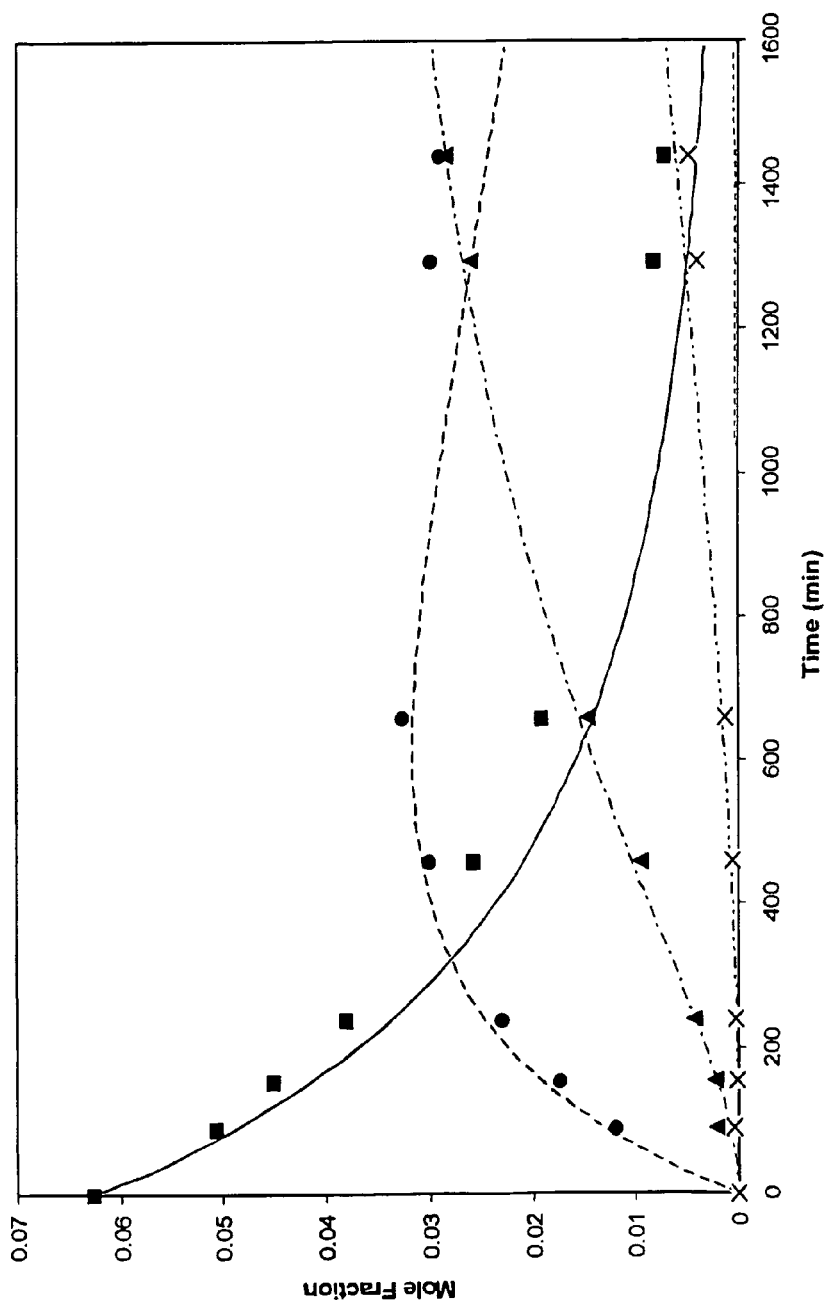
FIGS. 13A and 13B are graphs showing Reaction Conditions: Mole Ratio of Ethanol to Citric acid, 15:1, Catalyst Loading, 2 wt %, Reaction Temperature, 78° C.
Figure 13B:
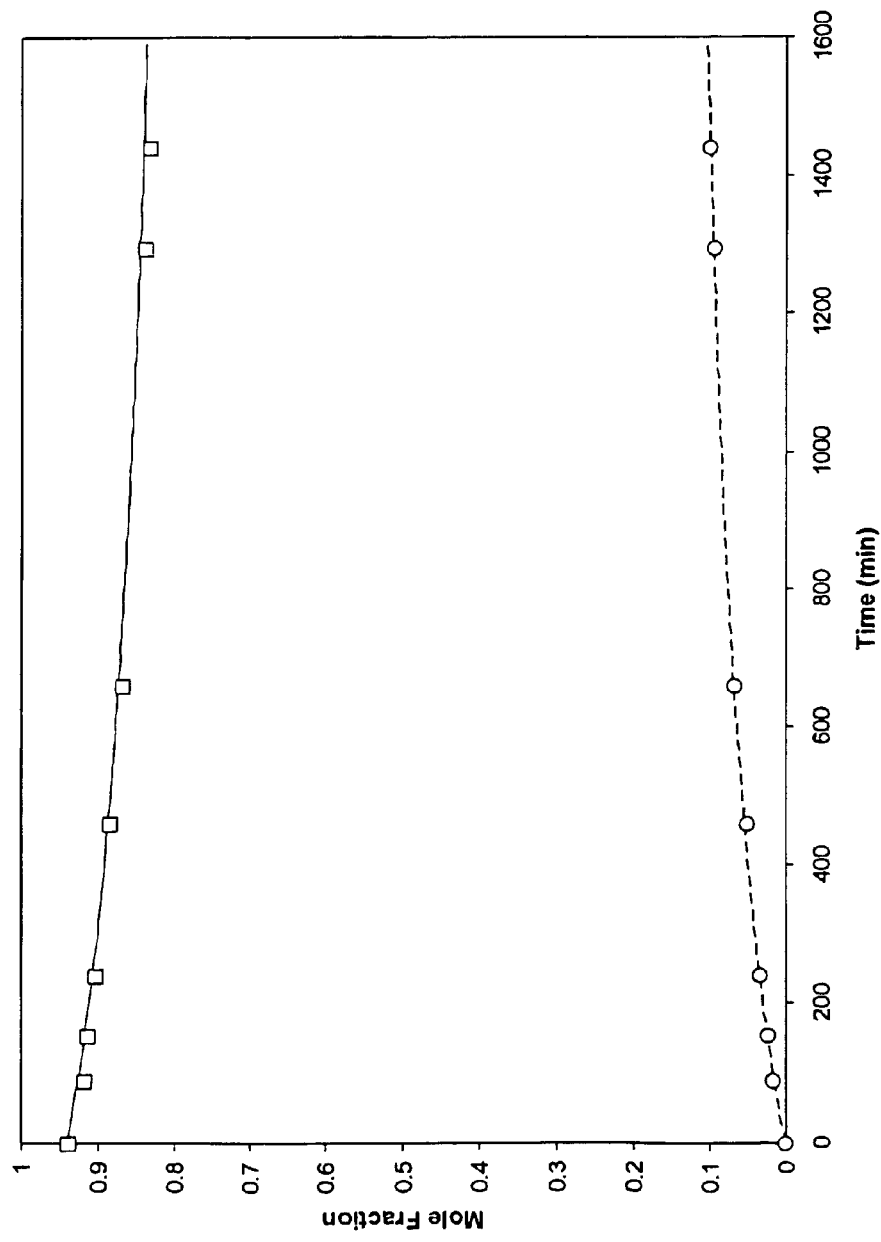
Figure 14A:
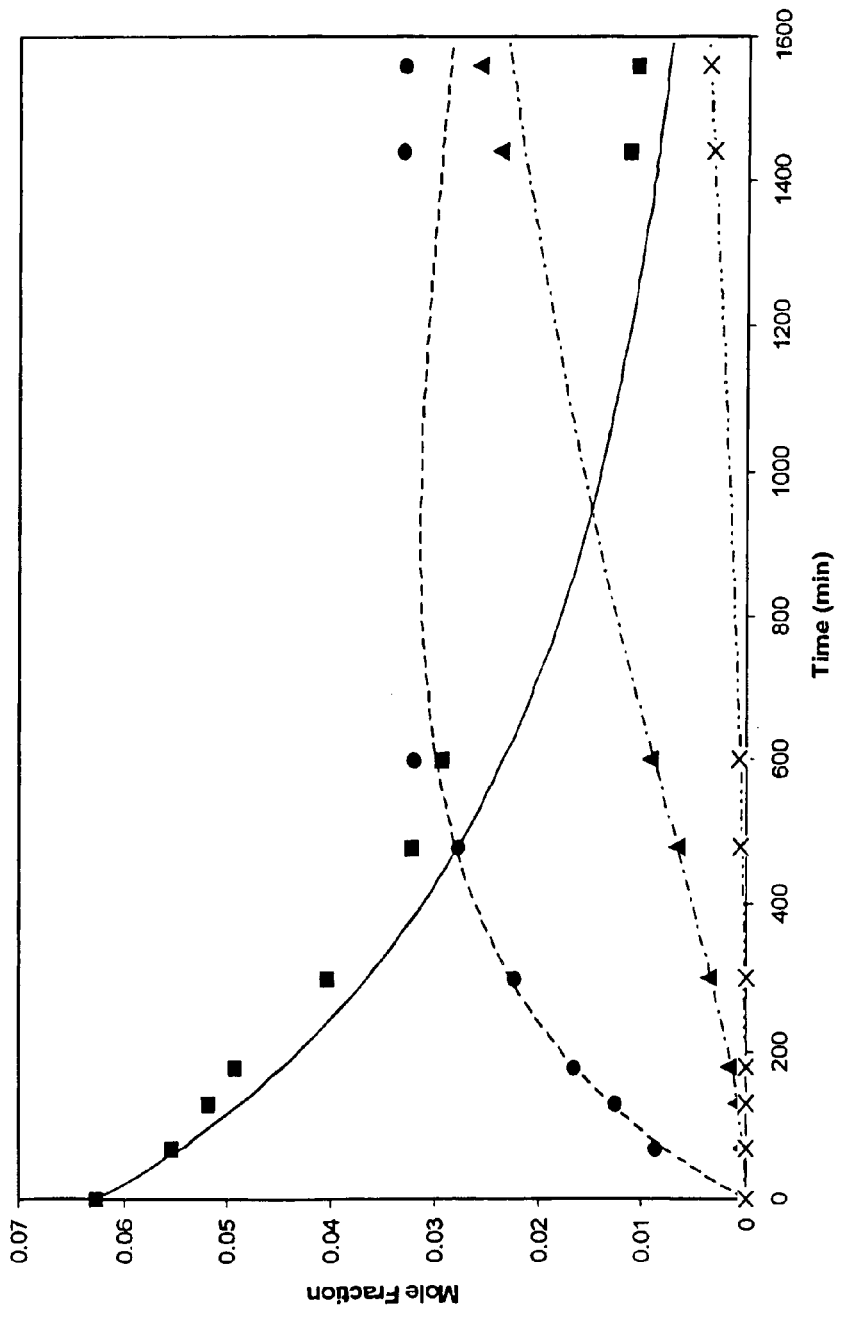
FIGS. 14A and 14B are graphs showing Reaction Conditions: Mole Ratio of Ethanol to Citric acid, 15:1, Catalyst Loading, 1 wt %, Reaction Temperature, 78° C.
Figure 14B:
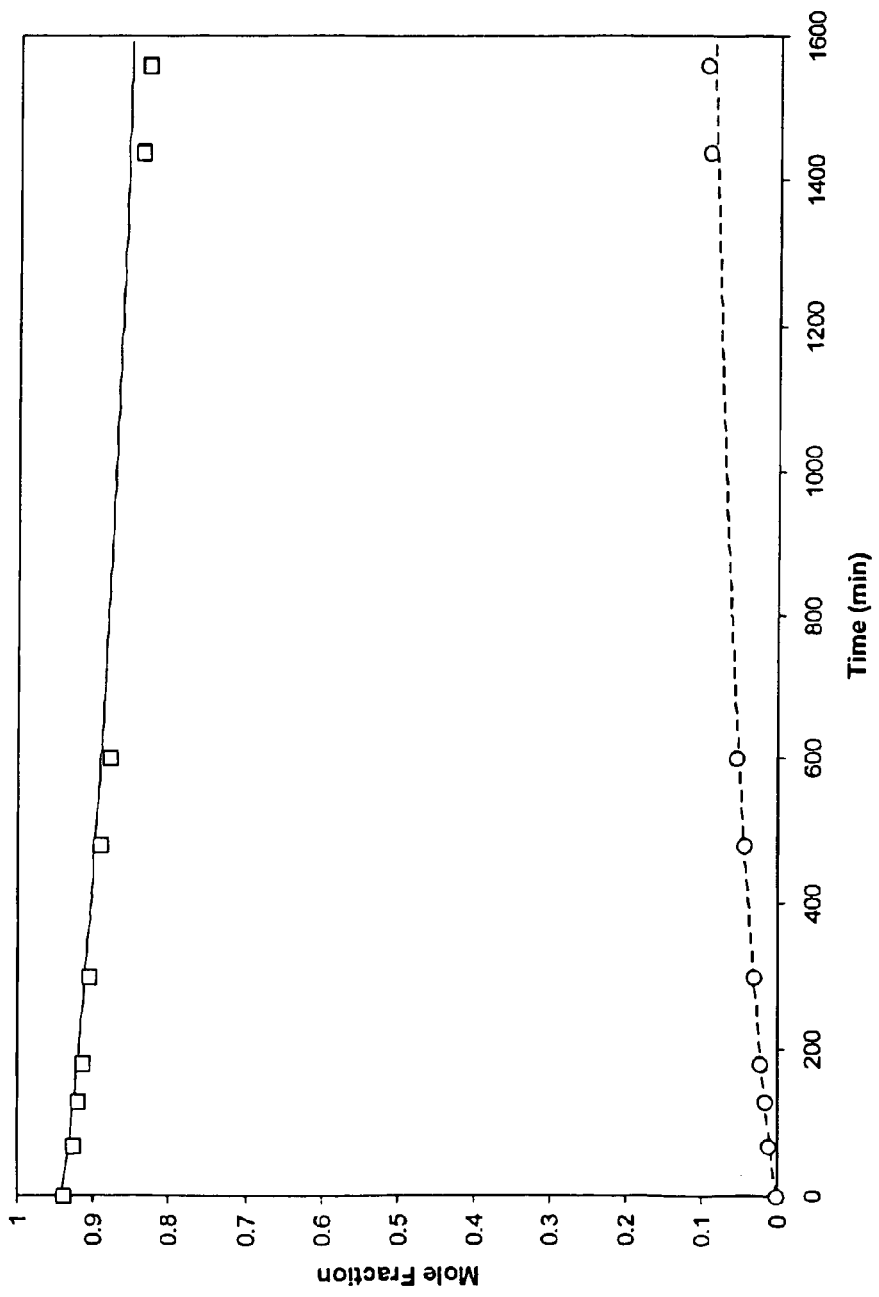
Figure 15A:
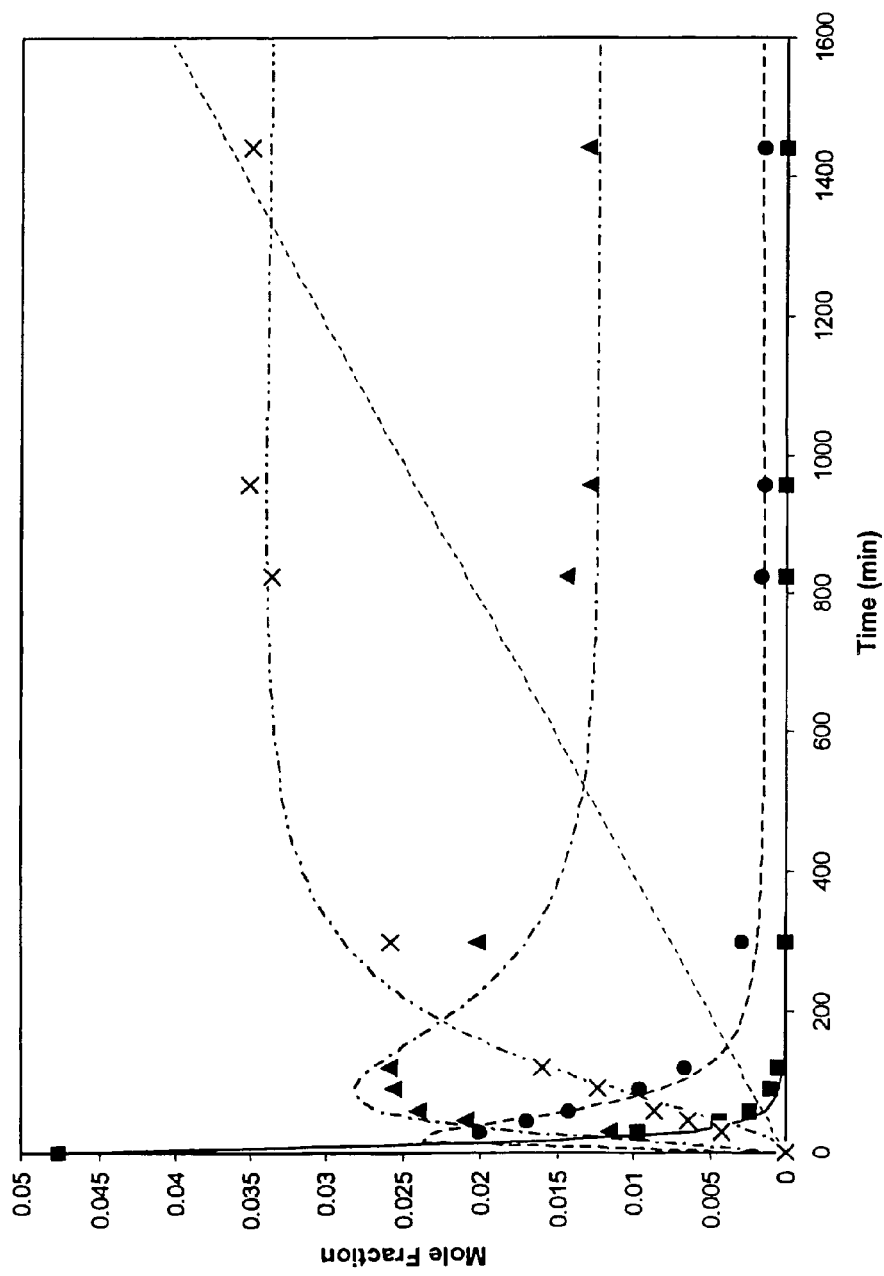
FIGS. 15A and 15B are graphs showing Reaction Conditions: Mole Ratio of Ethanol to Citric acid, 20:1, Catalyst Loading, 5 wt %, Reaction Temperature, 120° C.
Figure 15B:
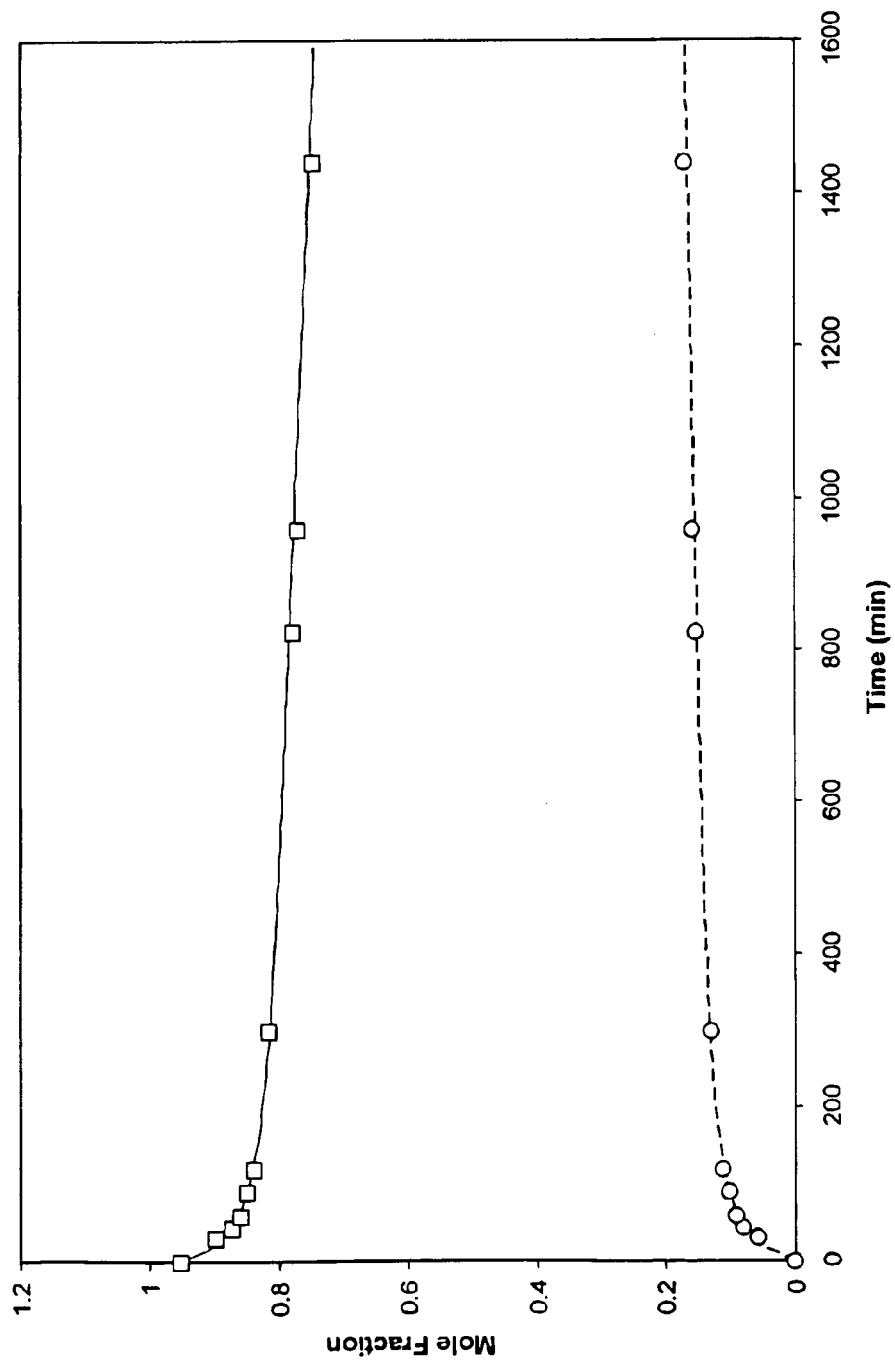
Figure 16A:
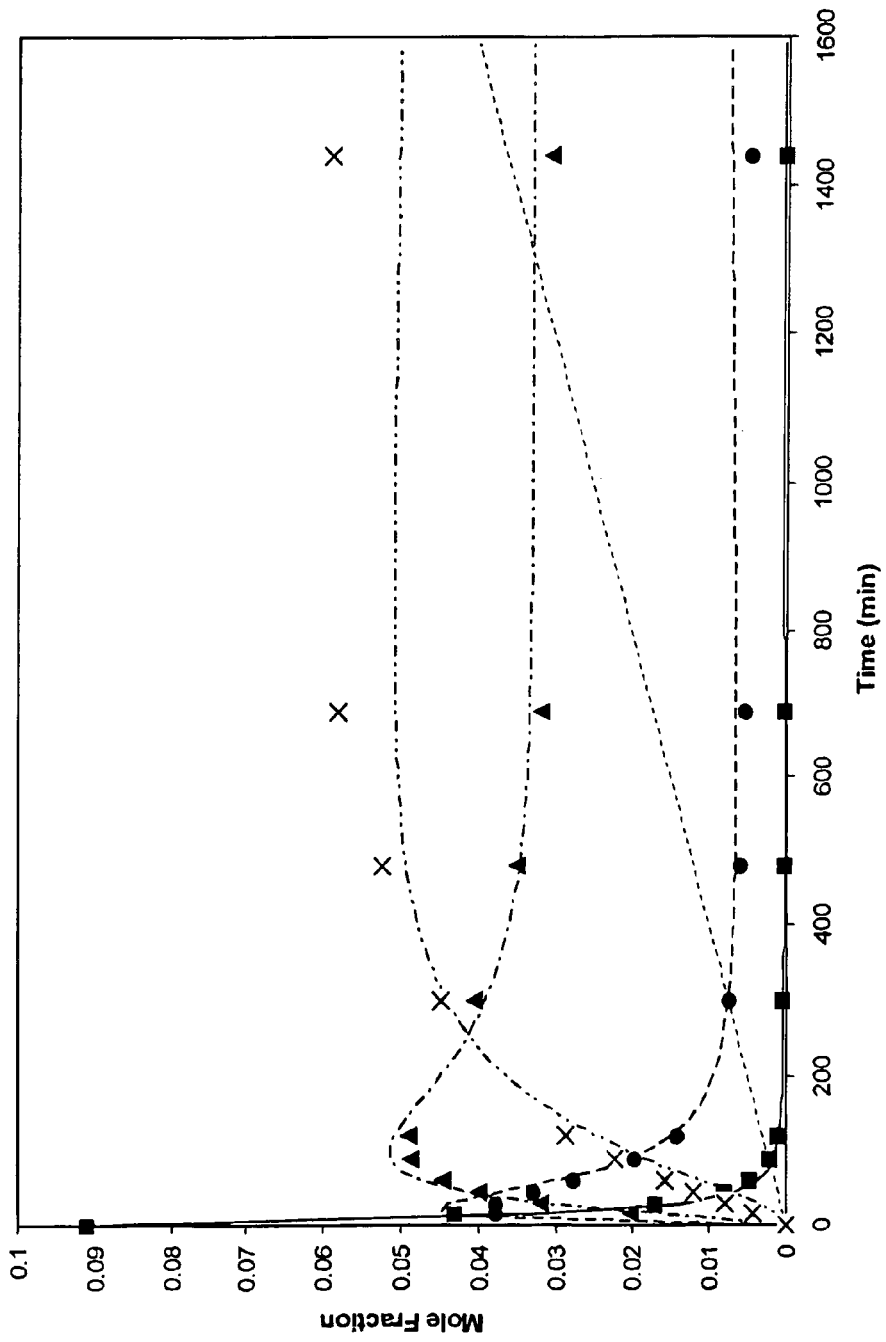
FIGS. 16A and 16B are graphs showing Reaction Conditions: Mole Ratio of Ethanol to Citric acid, 10:1, Catalyst Loading, 5 wt %, Reaction Temperature, 120° C.
Figure 16B:
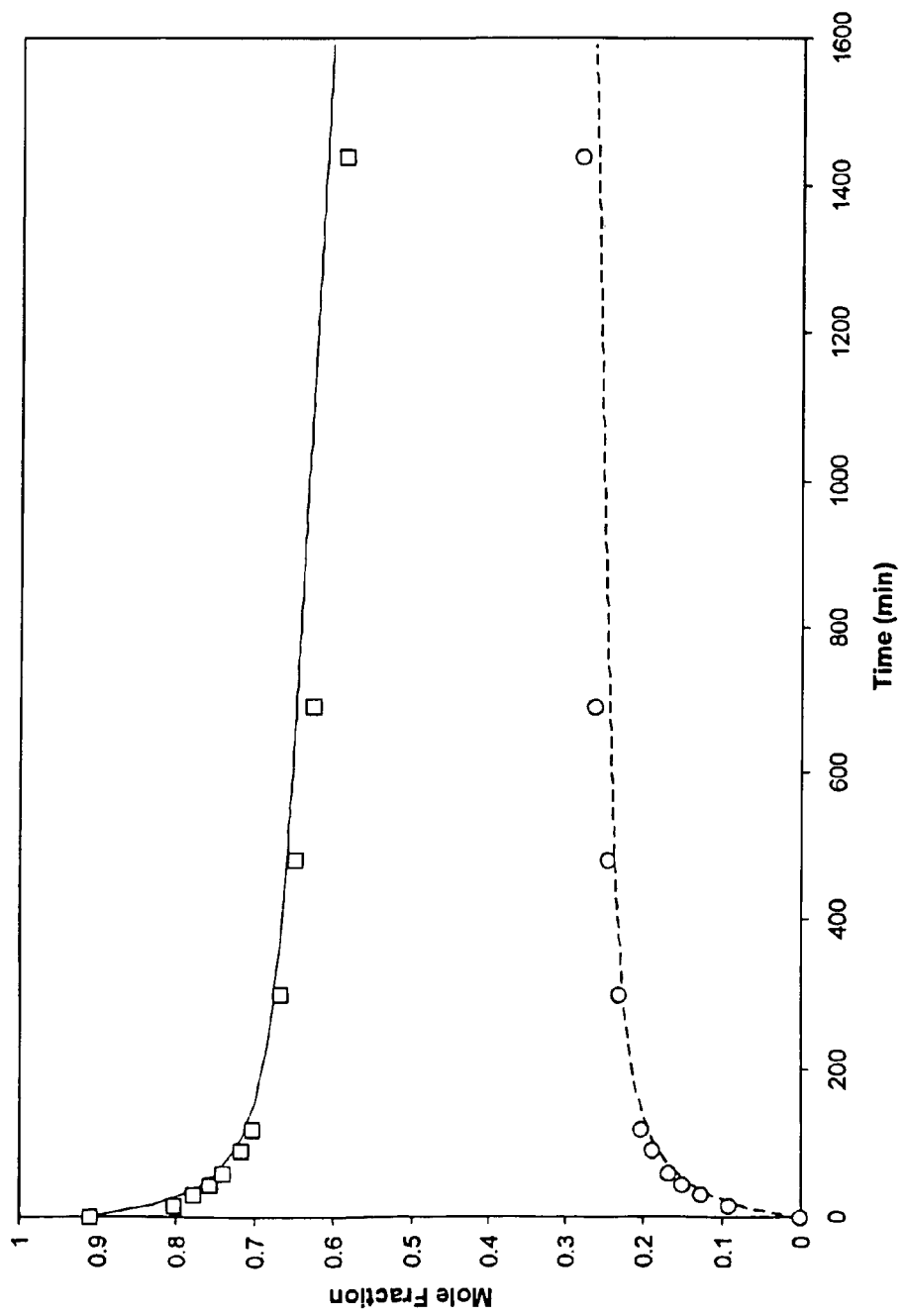
Figure 17A:
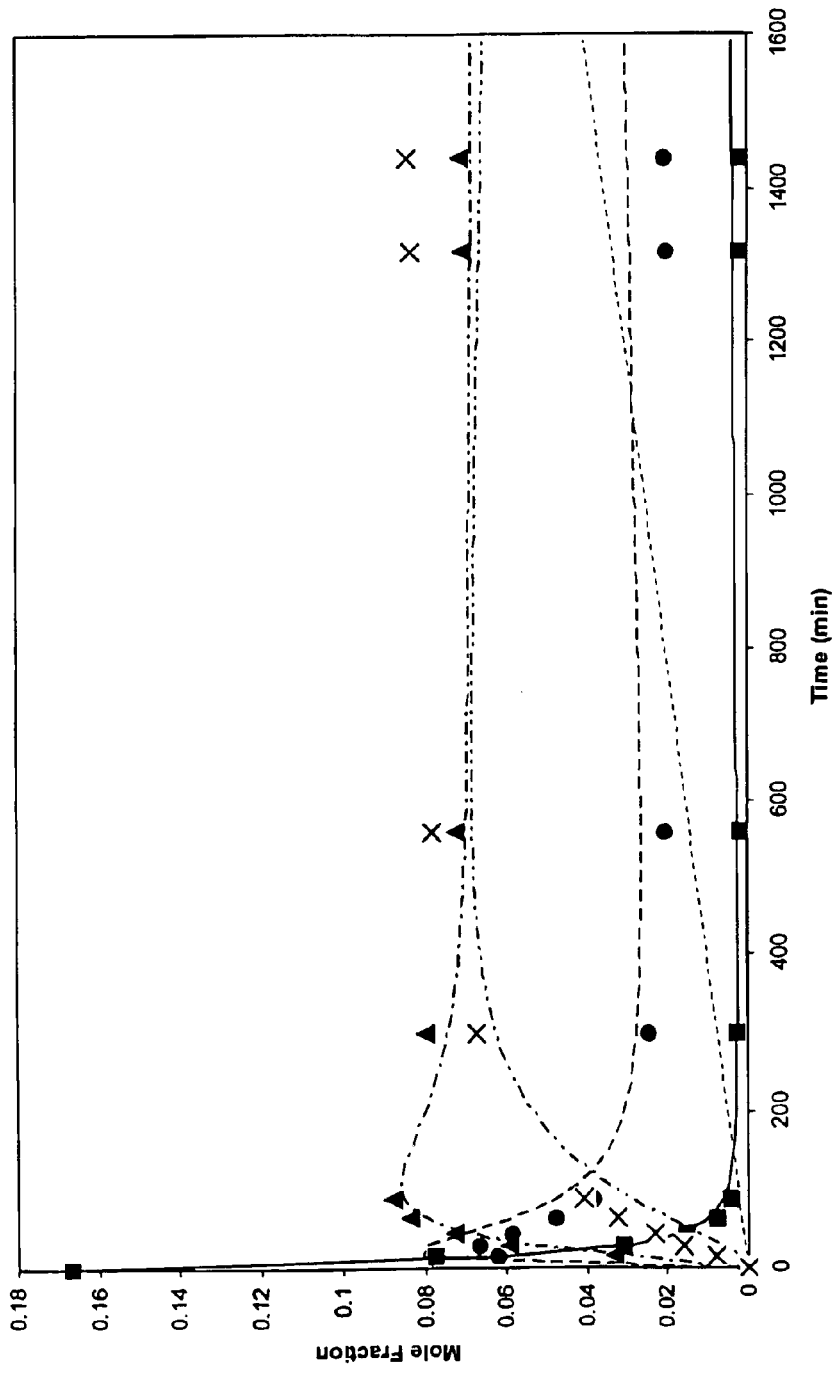
FIGS. 17A and 17B are graphs showing Reaction Conditions: Mole Ratio of Ethanol to Citric acid, 5:1, Catalyst Loading, 5 wt %, Reaction Temperature, 120° C.
Figure 17B:
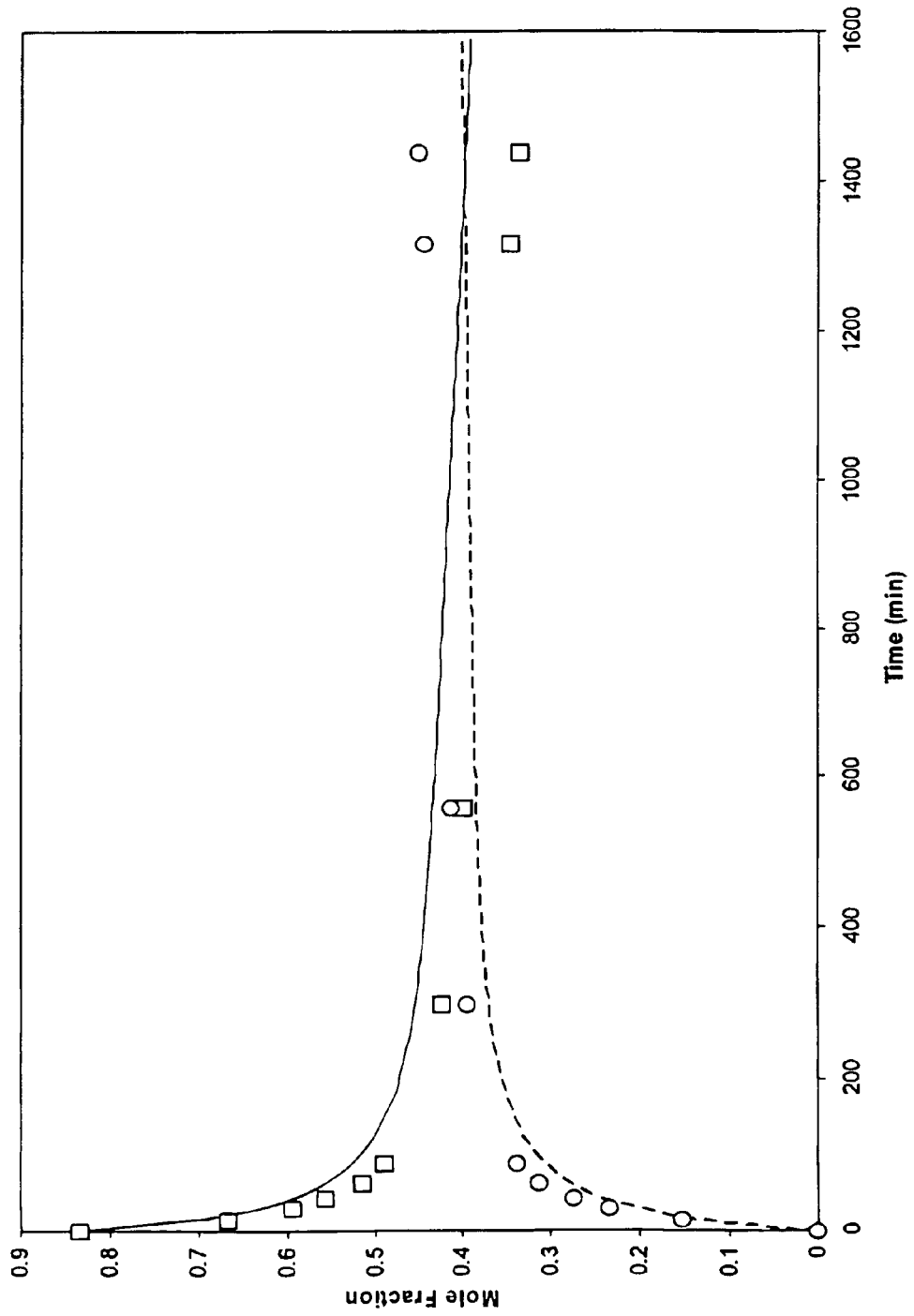
Figure 18A:
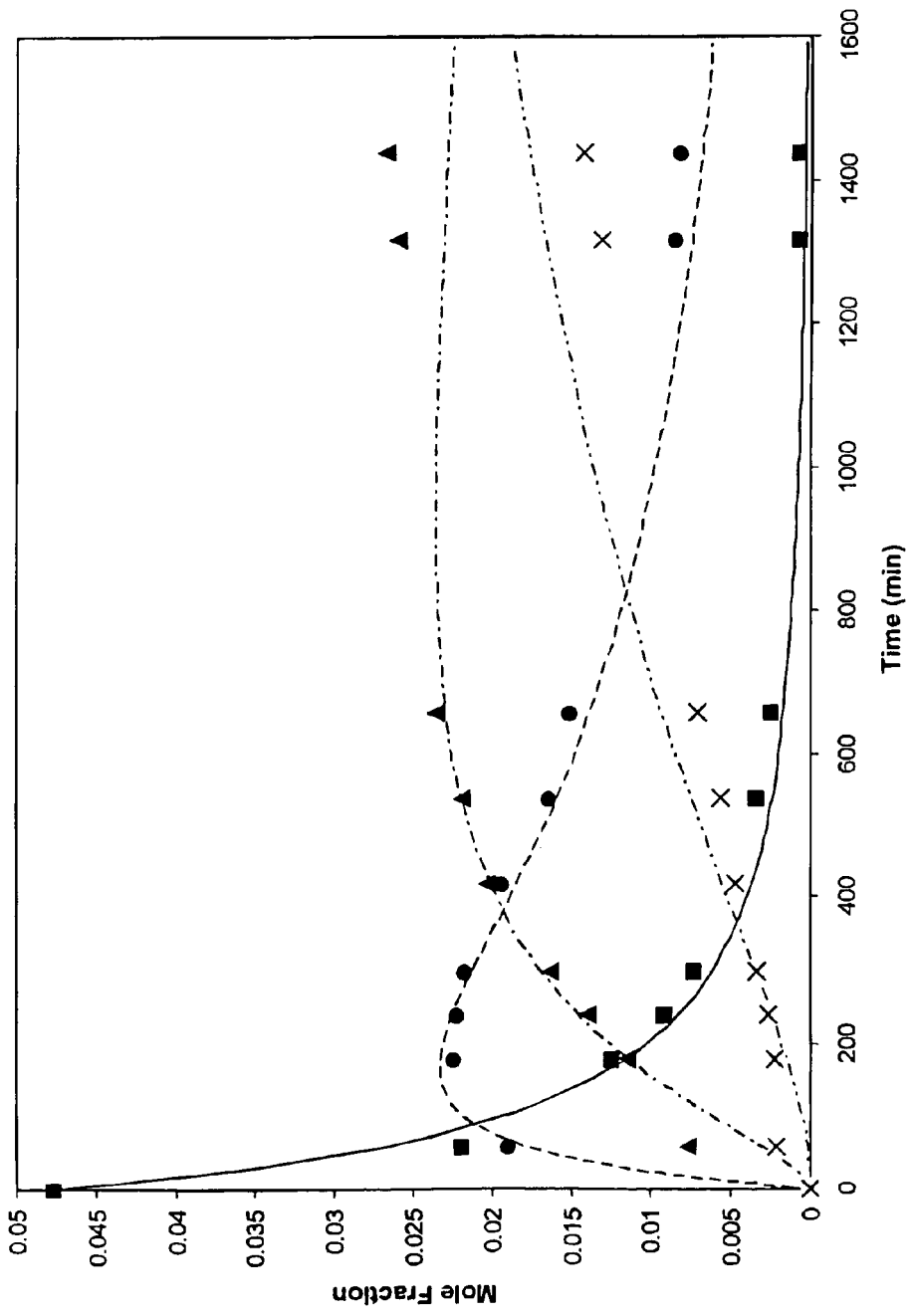
FIGS. 18A and 18B are graphs showing Reaction Conditions: Mole Ratio of Ethanol to Citric acid, 20:1, Reaction Temperature, 120° C.
Figure 18B:
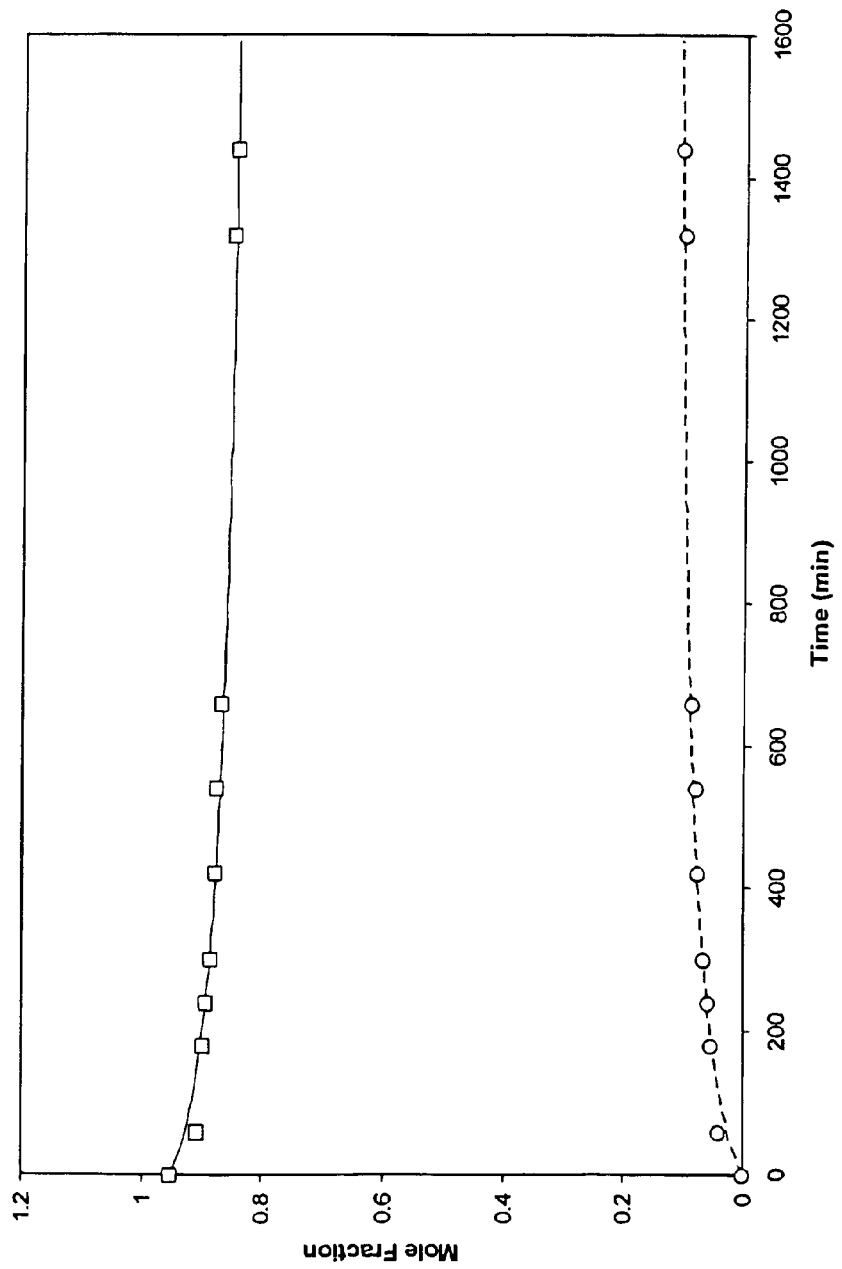
Figure 19B:
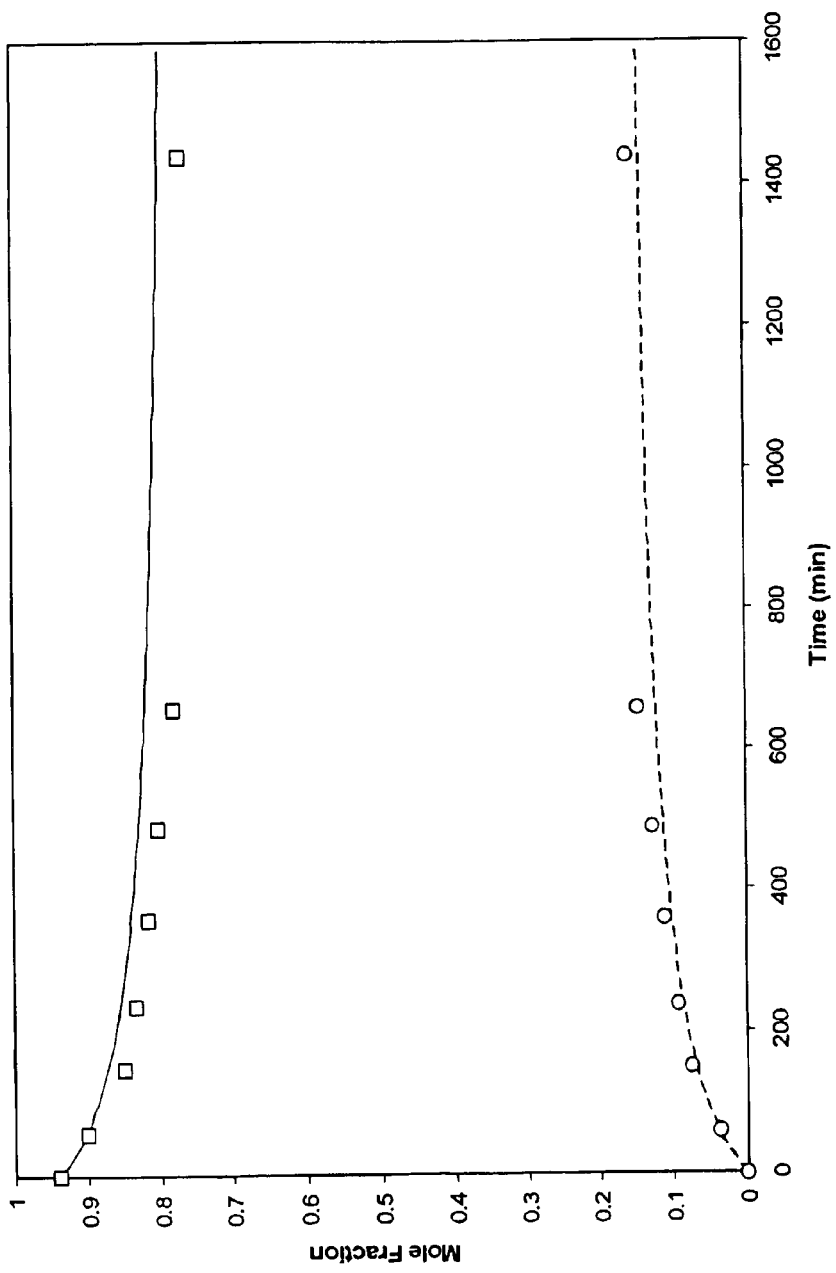
Figure 20B:
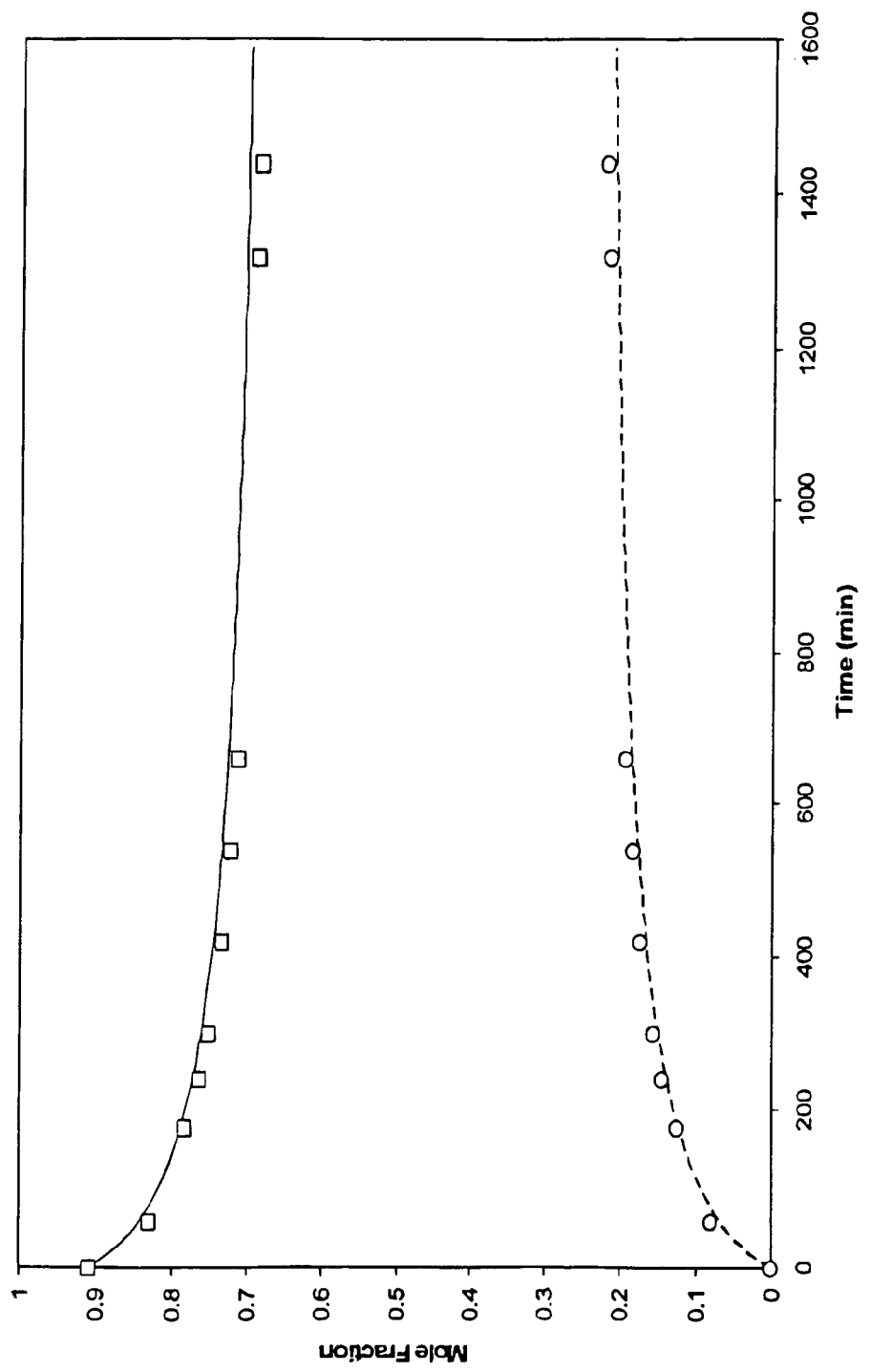
Figure 21B:
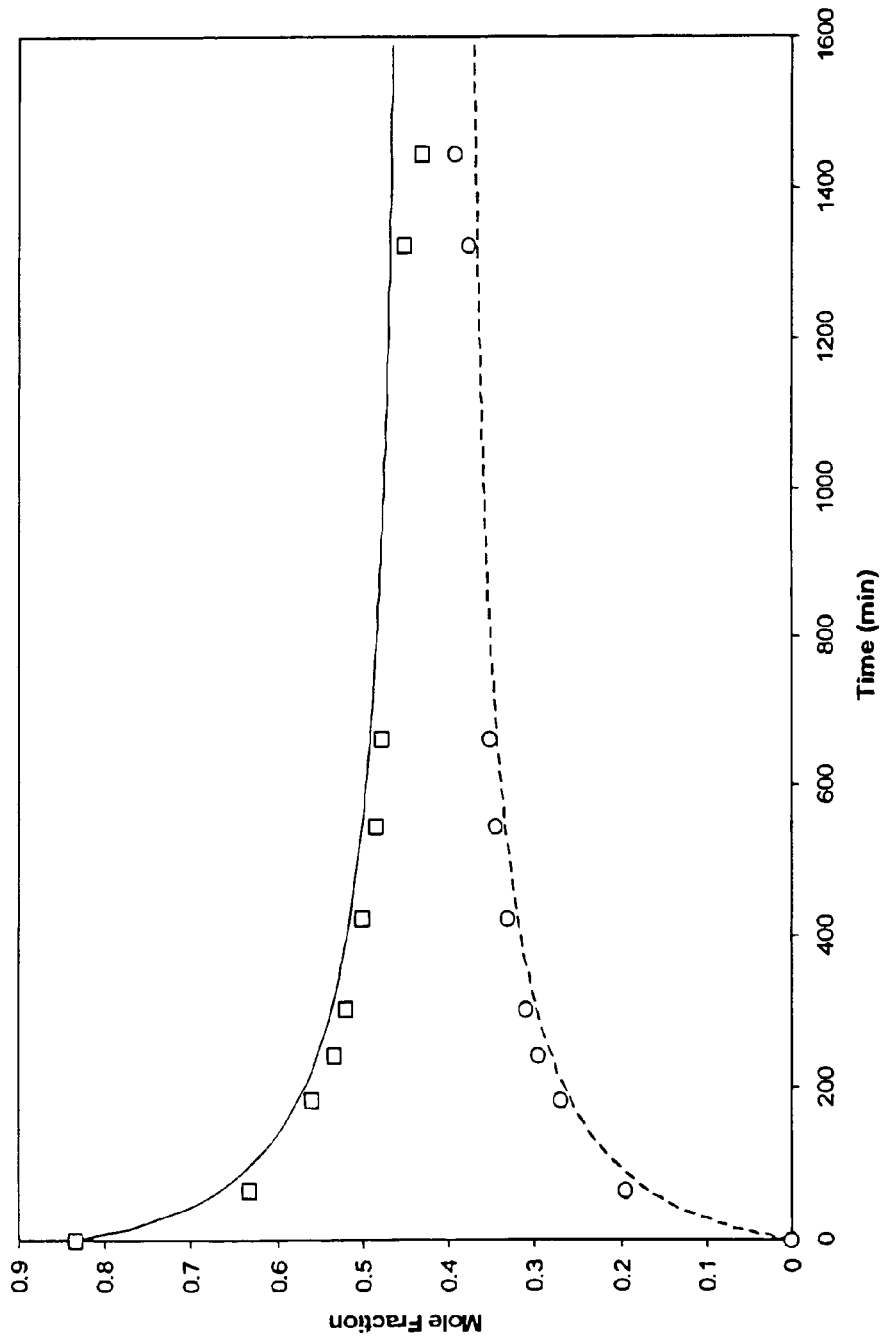

Experimental investigations of tri-ethyl citrate formation via continuous reactive distillation were performed in a pilot-scale glass column with an inner diameter of 50 mm and total height of 5.5 m constructed from Pyrex glass tubes (Asthana et al, *Org. Process Res. & Dev.*, 9, 599-607 (2005), Asthana et al., U.S. patent application Ser. No. 10/894,307 (2004)). A schematic representation of the experimental column used in the present study is shown in FIG. 2. The column consists of three sections: a 2.6 m long reactive section packed with Katapak-S structured packing elements (Sulzer Chemtech Ltd, Winterthur, Switzerland). The Katapak-S packing is filled with approximately 150 g per meter length of Amberlyst-15, a strong acid macroporous cation exchange resin of 0.7 mm average bead size. The reactive section is enclosed by a non-reactive enriching section above height of 0.8 m and a non-stripping section below height of 1.0 m. Empty Katamax structured packing (Koch-Glitsch, Ltd.) is used to fill non-reactive column sections. The pressures were between 1.0 and 4.0 atmospheres. The temperatures were 80° C. to 120° C.

The column is equipped with an electronic reflux splitter to control reflux ratio, a total condenser with chiller capable of achieving a condenser temperature of −20° C., and a reboiler with an outlet to maintain a constant level and allow product withdrawal. The reboiler volume is 1.0 liter. Two feed pumps were utilized to feed solutions to the column at a controlled rate. The columns have several ports along their length that allow internal temperature measurements at ten locations equally divided over the column length, introduction of feed, and sample withdrawal. The columns are wrapped with a set of electric heating tapes that are controlled by surface thermocouples and Omega controllers and further insulated using glass wool in order to obtain near adiabatic operating conditions.

Reactive Distillation Column Experimental Procedure

The reactive distillation column was configured such that a feed consisting of 24 wt % citric acid in anhydrous ethanol (F1 in FIG. 2) was fed near the top of rectification zone (0.2 m from top of column), while preheated ethanol (F2 in FIG. 2), either in liquid or vapor form, was fed 1 m above the reboiler at the bottom of the reactive zone. The ratio of molar feed ratios of ethanol to citric acid was typically 15:1 to 20:1. The reflux ratio (L/D) was set to zero, although a small amount of internal reflux was noted experimentally (L/D<0.05). The reboiler duty was held constant for all experiments.

The column was started by turning on the external heating tapes and reboiler heater, and starting the feed pumps at the specified feed rates. Steady state was generally achieved after about a volume of bottoms product equivalent to three reboiler volumes had been collected. Samples were then collected from the distillate and bottoms streams for product analysis. Steady state flow rates of feed, bottoms, and distillate streams were measured by timed filling of graduated cylinders.

The goal of column operation was to obtain tri-ethyl citrate along with some quantity of ethanol as the bottom product. The presence of ethanol in the reboiler was required to control reboiler temperature and thus prevent formation of oligomeric byproducts via secondary reactions of residual citric acid, mono-ethyl citrate and the di-ethyl citrate. We observed such byproducts in early experiments under conditions where no water or ethanol were present in the reboiler and high reboiler temperature was attained. The tri-ethyl citrate product can be purified by vacuum stripping out the ethanol in an additional separation column.

The glass column operating pressure was limited to 1 atm for reasons of safety. From batch kinetic experiments, we observed that ethyl citrate formation was relatively slow at 80° C. (the normal b.p. of EtOH). This kinetic limitation dictates that only relatively low conversion of citric acid to ethyl citrate can be obtained in the glass column—a major limitation in the experimental reactive distillation experiments.

Results and Discussion

Batch Kinetic Experiments

Several batch kinetic experiments were carried out to study the effects of reaction temperature, catalyst loading, and initial reactant molar ratio on the heterogeneously catalyzed esterification of citric acid with ethanol. It was observed from initial experimentation that the external mass-transfer resistances were negligible at a stirring speed of above 500 rpm. Hence all kinetic experiments were performed at 800 rpm. The influence of internal mass transfer resistances were neglected for reactions catalyzed by Amberlyst 15 (Gangadwala et al (*Ind. Eng. Chem. Res.* 42 2146-2155 (2003)), Liu et al (Catalytic synthesis of tri-butyl citrate with dealuminated USY zeolite. 11, 175-177 (2001)).

Effect of Reaction Temperature

FIGS. 3 to 7 show the effect of reaction temperature from 78° to 120° C. on the esterification of citric acid with ethanol at a catalyst loading of 5 wt % and an initial mole ratio of ethanol to citric acid of 15:1. The rate of conversion of citric acid, mono-ethyl citrate, and di-ethyl citrate clearly increases with increasing reaction temperature.

Effect of Catalyst Loading

FIGS. 8 to 11 show the effect of varying catalyst loading from 1 to 10% on the esterification of citric acid with ethanol at 120° C. and an initial mole ratio of ethanol to citric acid of 15:1. Additional data showing the effect of varying catalyst loading from 1 to 3% at reaction temperature of 78° C. and initial mole ratio of ethanol to citric acid of 15:1 are shown in FIG. 1 and FIGS. 12 to 14.

Effect of Initial Reactant Mole Ratio

The effect of varying the initial ethanol to citric acid mole ratio from 5:1 to 20:1 is shown in FIG. 5 and FIGS. 15 to 17. Reactions were conducted at 5 wt % catalyst loading and 120° C. The equilibrium extent of conversion to tri-ethyl citrate increases with increasing initial ethanol to citric acid molar ratio.

Self Catalyzed Reactions

Figure 22A:
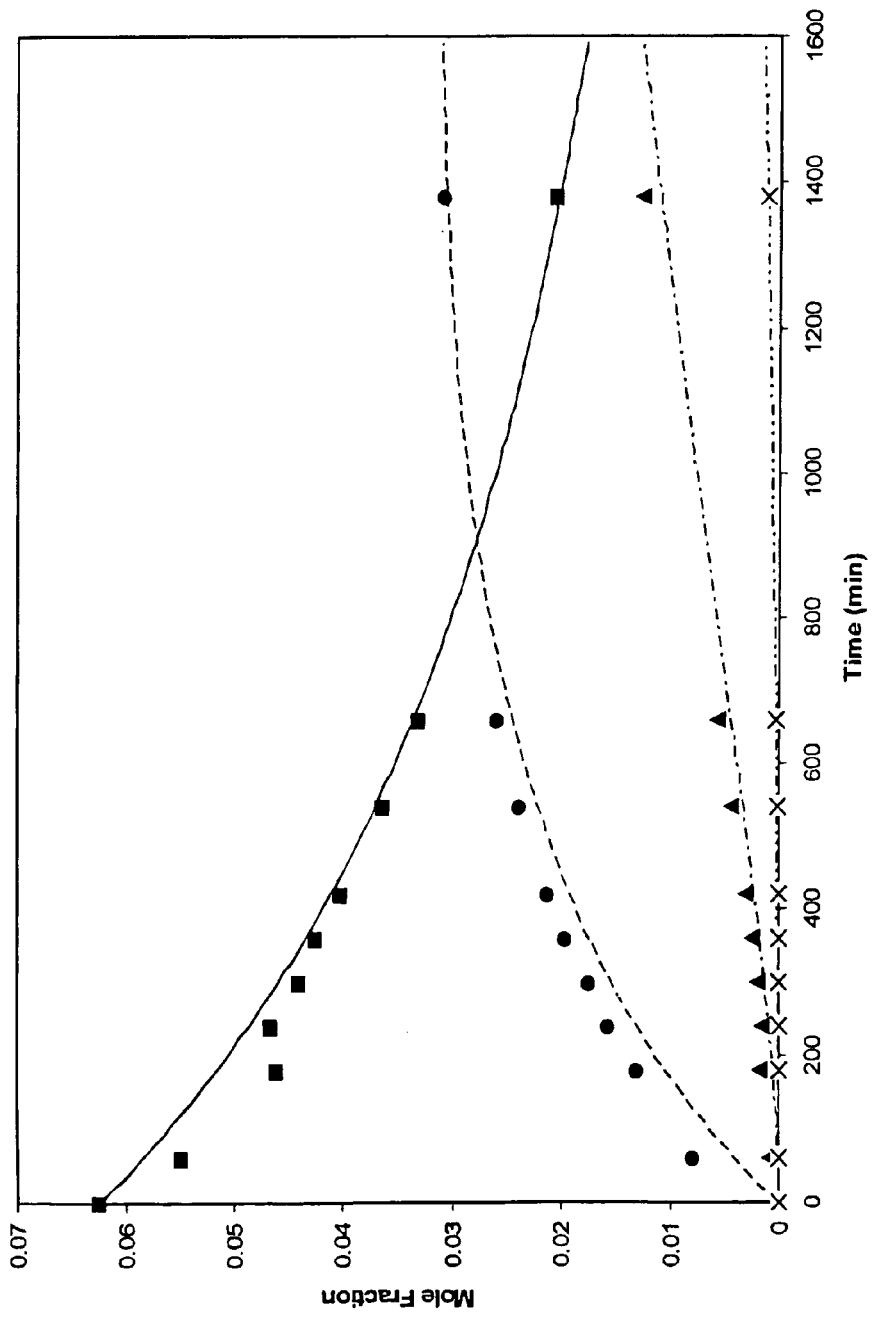
FIGS. 22A and 22B are graphs showing Reaction Conditions: Mole Ratio of Ethanol to Citric acid, 15:1, Reaction Temperature, 78° C.
Figure 22B:
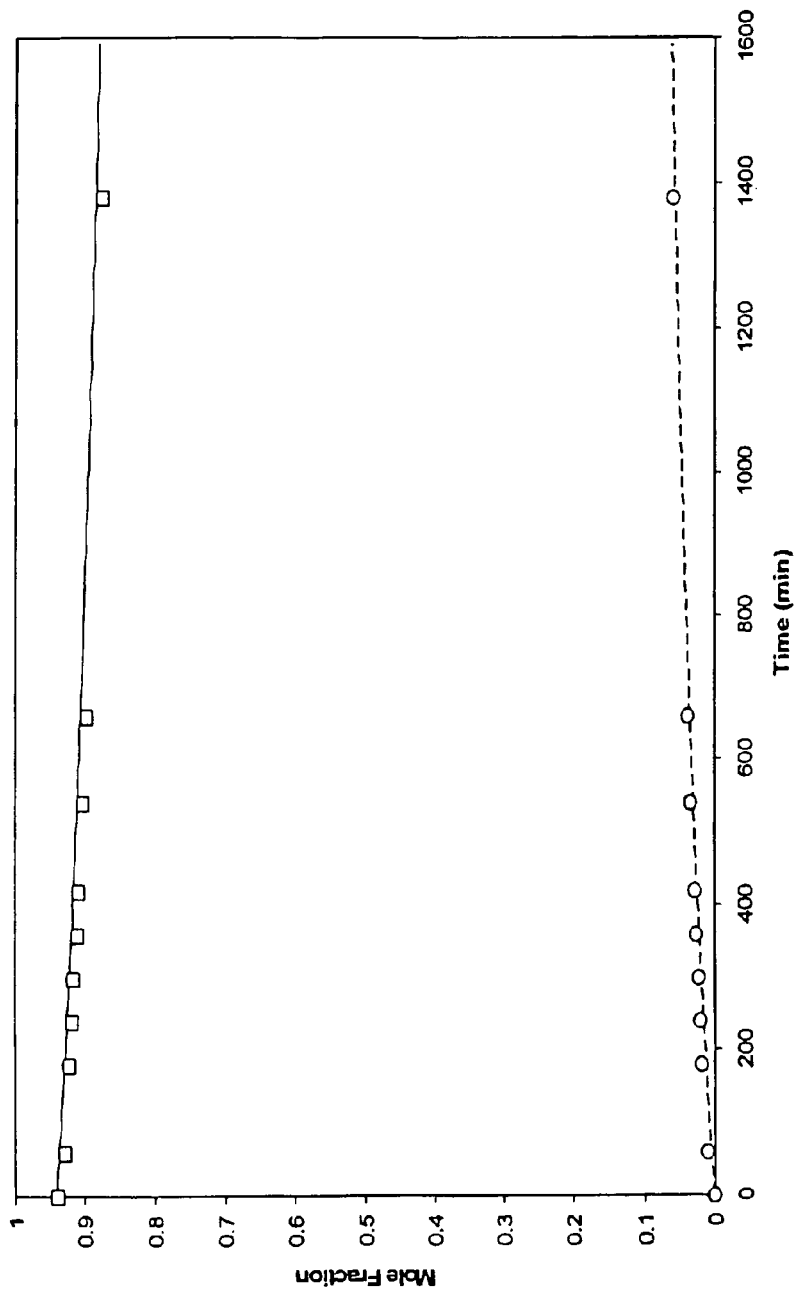
Figure 23B:
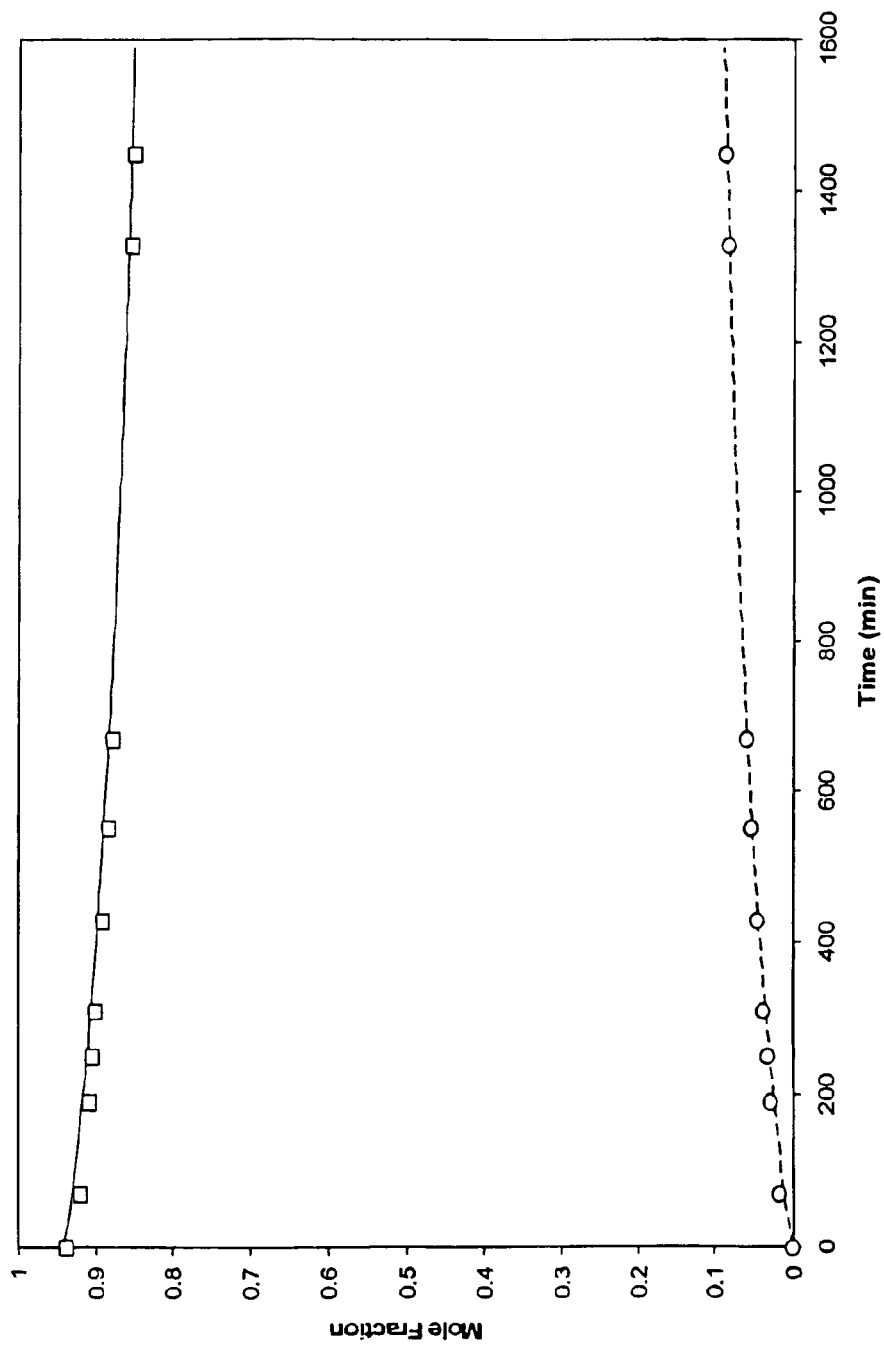
Figure 24A:
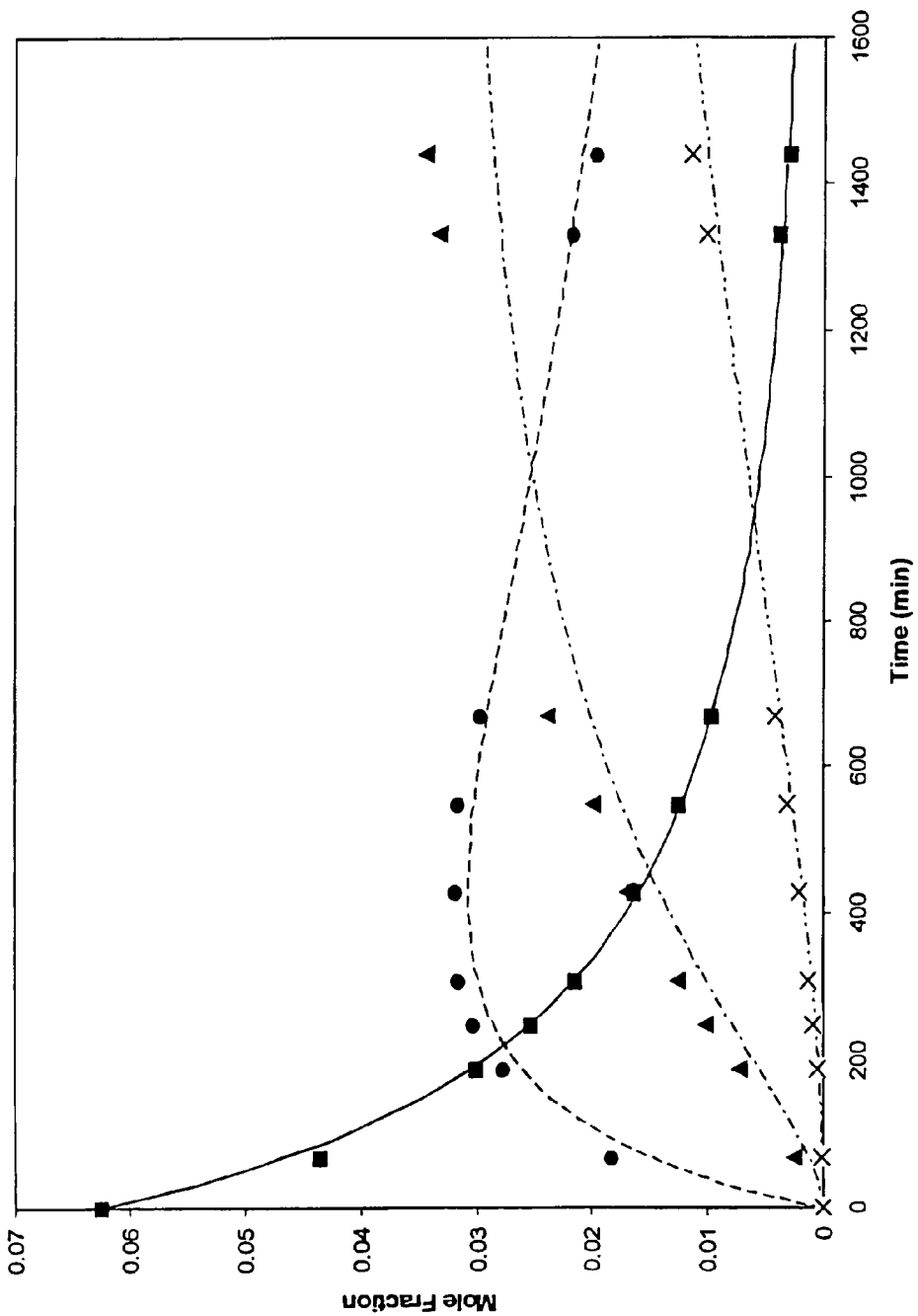
FIGS. 24A and 24B are graphs showing Reaction Conditions: Mole Ratio of Ethanol to Citric acid, 15:1, Reaction Temperature, 100° C.
Figure 24B:
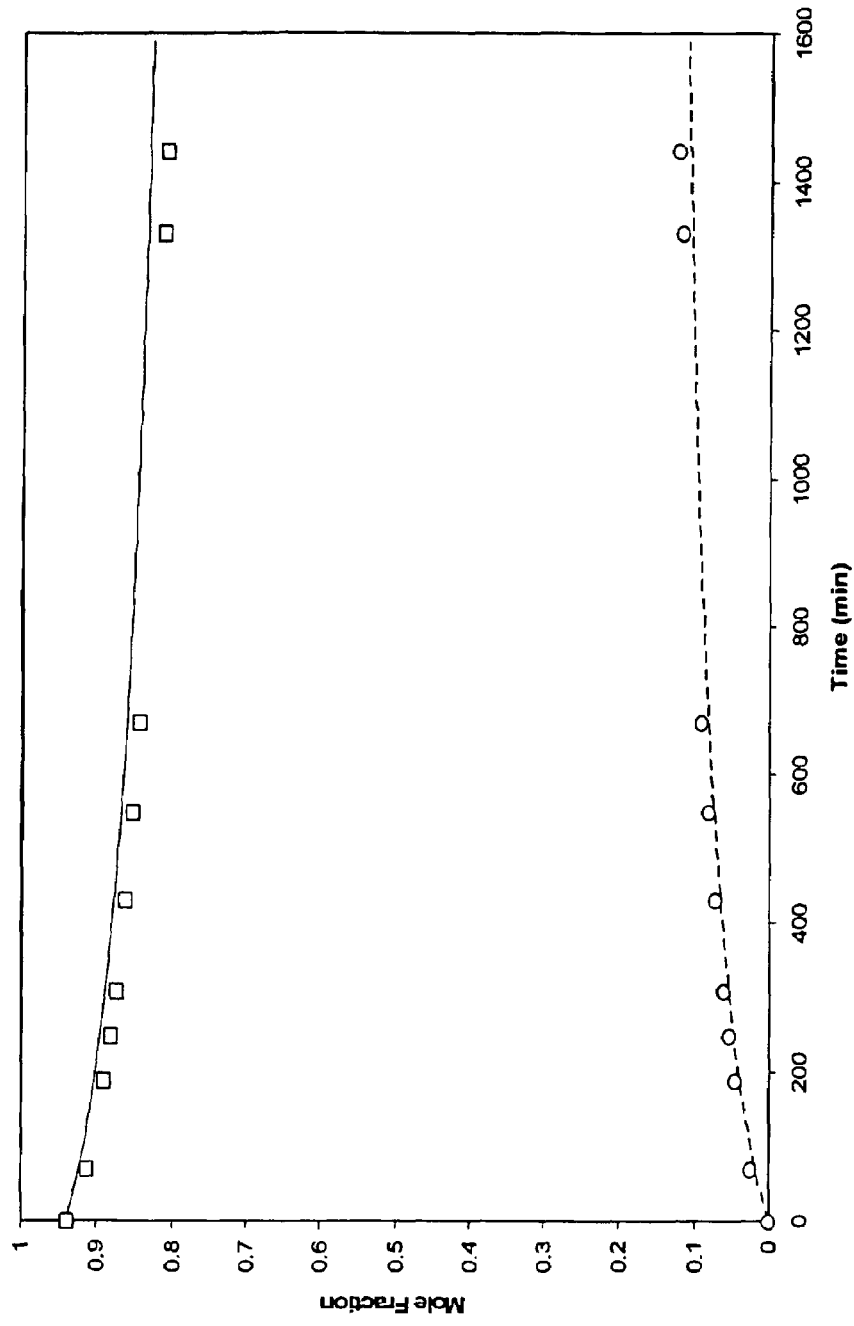
Figure 25A:
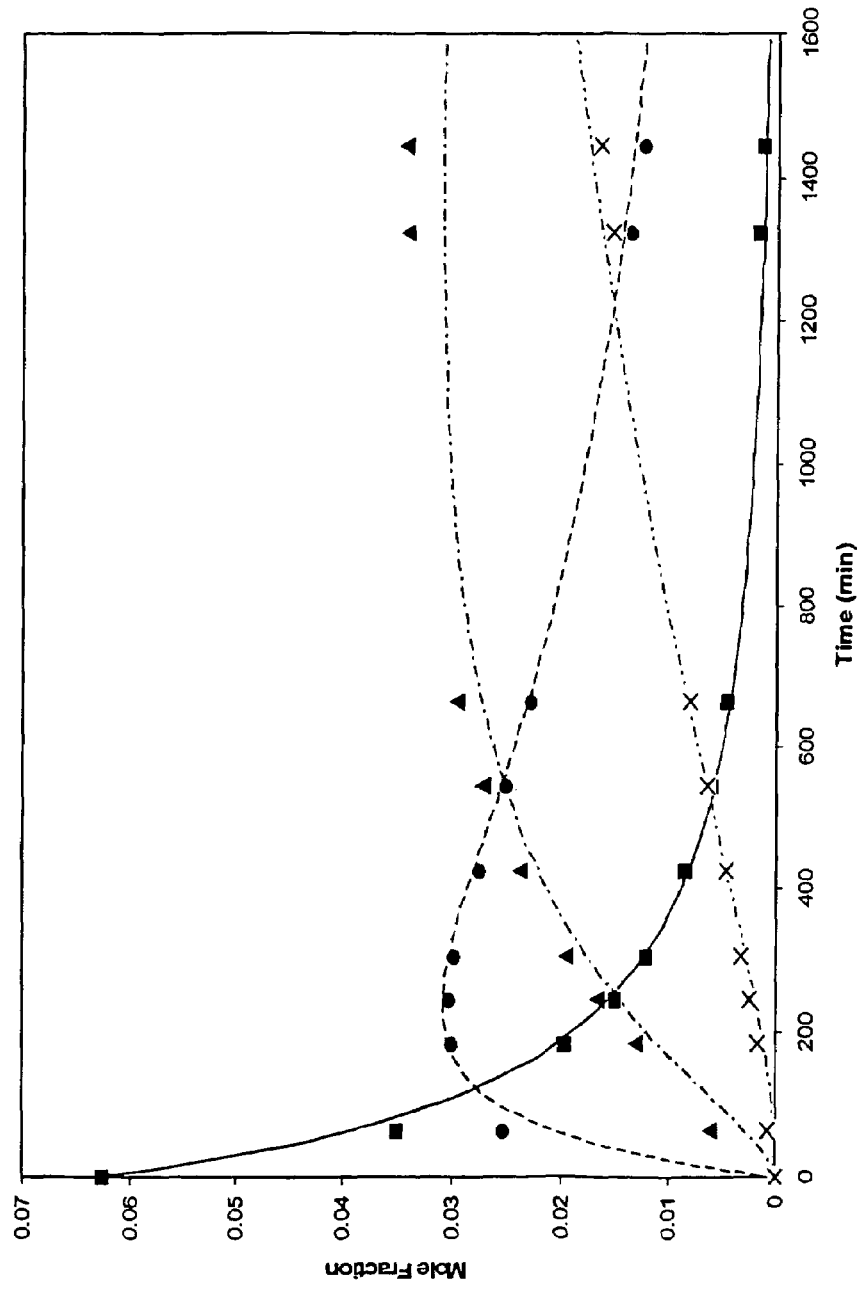
FIGS. 25A and 25B are graphs showing Reaction Conditions: Mole Ratio of Ethanol to Citric acid, 15:1, Reaction Temperature, 110° C.
Figure 25B:
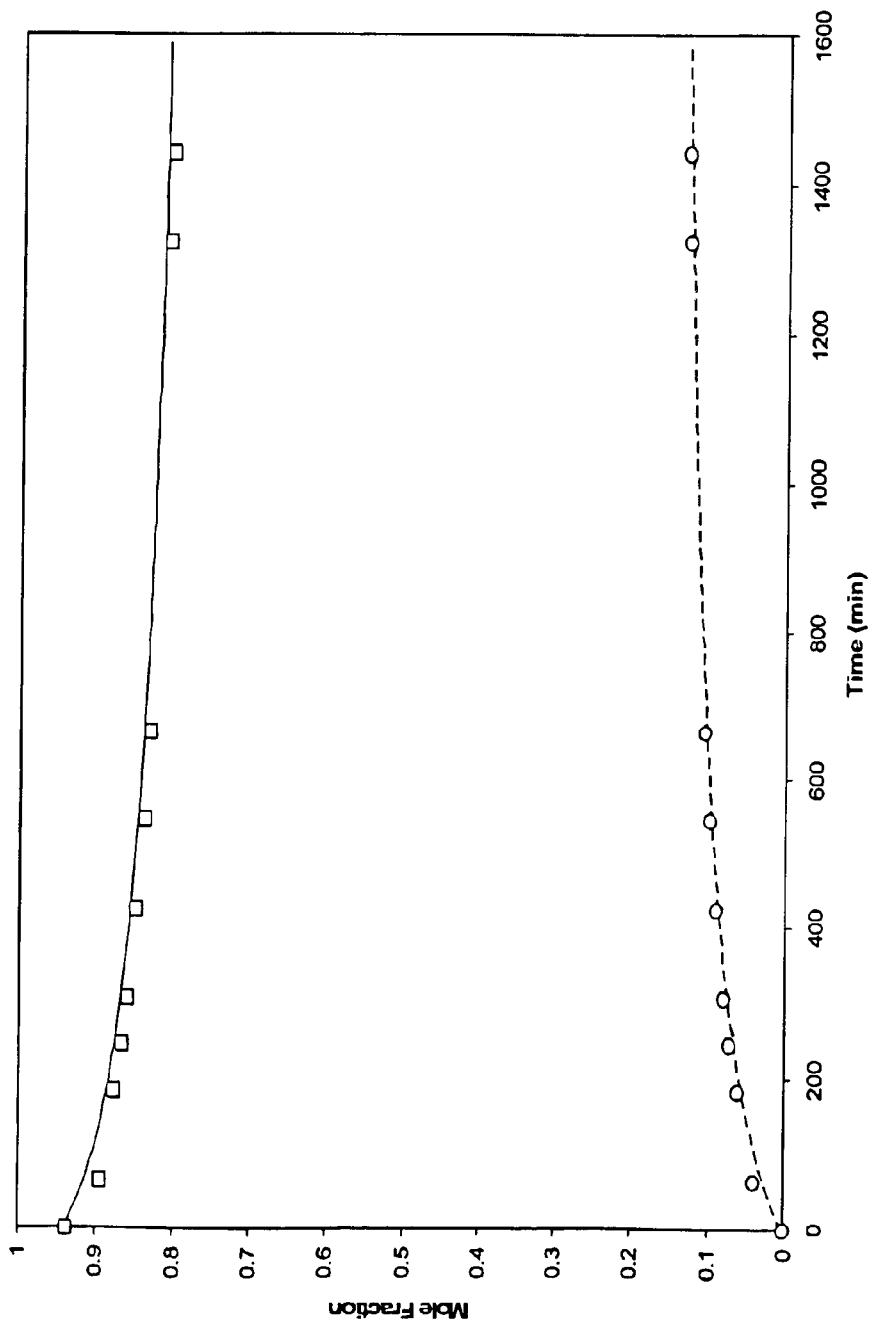

The self-catalyzed reactions of citric with ethanol at 120° C. and initial mole ratio of ethanol to citric acid from 5:1 to 20:1 are shown in FIGS. 18 to 21. FIG. 22 shows the self catalyzed reaction at 78° C. and 15:1 mole ratio of ethanol to citric acid, and FIGS. 23, 24 and 25 show the self catalyzed reaction at 90° C., 100° C. and 110° C., respectively with a 15:1 mole ratio of ethanol to citric acid. In comparing data in these figures to those from FIGS. 2 to 17, it is clear that the uncatalyzed rate contributes significantly to esterification at low catalyst loadings especially at higher reaction temperature of 120° C. at atmospheric pressure.

Kinetic Modeling

Preliminary Model I: Catalytic Esterification Only (Neglecting Self-Catalyzed Reactions)

A pseudo-homogeneous kinetic model has been considered for the series reactions associated with esterification of citric acid with ethanol. In this first case the rate of the uncatalyzed reactions has been neglected and it is assumed that the reactions are catalyzed only by presence of the ion exchange resin catalyst. The reactions given in FIG. 1 can be written as:

$$CA + EtOH \underset{K_{eq,CA}}{\overset{k_{CA}}{\rightleftarrows}} MEC + W \quad (1)$$

$$MEC + EtOH \underset{K_{eq,MEC}}{\overset{k_{MEC}}{\rightleftarrows}} DEC + W \quad (2)$$

$$DEC + EtOH \underset{K_{eq,DEC}}{\overset{k_{DEC}}{\rightleftarrows}} TEC + W \quad (3)$$

where mono-ethyl citrate is denoted as MEC, di-ethyl citrate as DEC, tri-ethyl citrate as TEC, ethanol as EtOH and water as W. No distinction is made in the model between the isomeric forms of mono-ethyl and di-ethyl citrate shown in FIG. 1; from HPLC we observe the presence of the individual isomers in their statistically expected concentrations.

From experiments at very long reaction times, the equilibrium constants for the three reactions were determined to be $K_{eq,CA}=4.2$, $K_{eq,MEC}=1.2$, and $K_{eq,DEC}=0.36$. The equilibrium constants were essentially independent of temperature over the 80° C. to 120° C. range which was studied in this work.

The kinetic model is built on the assumption that each of the above forward and reverse reactions is first order in each reactant. The model is based on the mole fraction of each species in solution. The general kinetic expressions for the second order reactions catalyzed by ion exchange resins are written as:

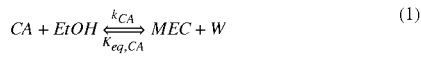

$$r_{CA,cat} = k_{CA,cat} \exp\left(\frac{-Ea_{CA,cat}}{RT}\right)\left(X_{CA}X_{EtOH} - \frac{X_{MEC}X_W}{K_{eq,CA}}\right) \quad (4)$$

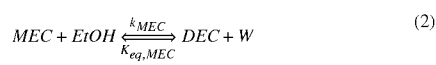

$$r_{MEC,cat} = k_{MEC,cat} \exp\left(\frac{-Ea_{MEC,cat}}{RT}\right)\left(X_{MEC}X_{EtOH} - \frac{X_{DEC}X_W}{K_{eq,MEC}}\right) \quad (5)$$

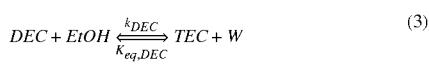

$$r_{DEC,cat} = k_{DEC,cat} \exp\left(\frac{-Ea_{DEC,cat}}{RT}\right)\left(X_{DEC}X_{EtOH} - \frac{X_{TEC}X_W}{K_{eq,DEC}}\right) \quad (6)$$

where the subscript cat denotes the catalysis in presence of ion exchange resin catalysts. Parameters for the model were estimated by minimizing the mean square difference between the experimental and calculated liquid phase mole fractions of the various species over the course of reaction. Mathematically this is represented as $$F_{min}^2 = \frac{\sum\limits_{samples}(x_{i,cal} - x_{i,expt})^2}{n_{samples}} \quad (7)$$

The calculated weight fractions of the components involved in the reaction are compared to the experimental ones, giving the mean relative deviation, represented as $$F_{rel} = \frac{\sum\limits_{samples}\left|\frac{x_{i,cal} - x_{i,expt}}{x_{i,expt}}\right|}{n_{samples}} \times 100\% \quad (8)$$

All data were included in the fitting of the kinetic parameters to experiments when the effect of self-catalyzed reaction were neglected. The values of the kinetic parameters in Equations 4 to 6 that best fit the model are shown in Table 1.

TABLE 1

Values of pre-exponential factor and energy of activation for Preliminary Model I (ion-exchanged catalytic rate only).

| Reaction | k Preexponential factor per gm catalyst basis (kmol i/kgmol n/min) | E Energy of Activation |
|---|---|---|
| CA + EtOH ↔ MEC + W | 296260 | 60013 |
| MEC + W ↔ CA + EtOH | 70038 | 60013 |
| MEC + EtOH ↔ DEC + W | 132526 | 60016 |
| DEC + W ↔ MEC + EtOH | 109525 | 60016 |
| DEC + EtOH ↔ TEC + W | 32127 | 60013 |
| TEC + W ↔ DEC + EtOH | 89244 | 60013 |

Preliminary Model II: Self-Catalyzed Esterification Only

The rates of the self-catalyzed reactions are substantially high and cannot be neglected. Moreover, the calculated reaction rate using Preliminary Model I are substantially lower than experimental rates at a reaction temperature of 120° C. This leads to the conclusion that self-catalyzed reactions cannot be neglected at higher temperatures especially for the reaction of citric acid.

In the second part of this work, the self-catalyzed reactions have been correlated using a pseudo-homogeneous model based on the law of mass action as first order with respect to the catalytic acid concentration, reacting acid concentration and alcohol concentration. In absence of any supporting information from literature, the strength of all the COOH groups have been taken to be the same. To elaborate, the acid strength of mono-ethyl citrate is taken as ⅔ of that of citric acid, and that for di-ethyl citrate as ⅓ of that of citric acid, since they contain 2 and 1 COOH groups, respectively.

The reaction rate for the self-catalyzed reaction can be written in a generalized form as $$r_{self} = k_{self} X_{catalytic\ acid} \left( X_{reacting\ acid} X_{alcohol} - \frac{X_{ester} X_{water}}{K_{eq}} \right) \quad (9)$$

The catalytic acid concentration in Eq (9) can be written as $$X_{catalytic\ acid} = \left( X_{CA} + \frac{2}{3} X_{MEC} + \frac{1}{3} X_{DEC} \right) \quad (10)$$

Equations 9 and 10 can be rewritten for the citric acid esterification reactions as $$r_{CA,self} = k_{CA,self} \exp\left(\frac{-Ea_{CA,self}}{RT}\right) \quad (11)$$
$$\left( X_{CA} + \frac{2}{3} X_{MEC} + \frac{1}{3} X_{DEC} \right)\left( X_{CA} X_{EtOH} - \frac{X_{MEC} X_W}{K_{eq,CA}} \right)$$

$$r_{MEC,self} = k_{MEC,self} \exp\left(\frac{-Ea_{MEC,self}}{RT}\right) \quad (12)$$
$$\left( X_{CA} + \frac{2}{3} X_{MEC} + \frac{1}{3} X_{DEC} \right)\left( X_{MEC} X_{EtOH} - \frac{X_{DEC} X_W}{K_{eq,MEC}} \right)$$

$$r_{DEC,self} = k_{DEC,self} \exp\left(\frac{-Ea_{DEC,self}}{RT}\right) \quad (13)$$
$$\left( X_{CA} + \frac{2}{3} X_{MEC} + \frac{1}{3} X_{DEC} \right)\left( X_{DEC} X_{EtOH} - \frac{X_{DEC} X_W}{K_{eq,DEC}} \right)$$

The rate for the self catalyzed esterification reactions were determined from the experimental data. The values of the kinetic parameters in Equations 11 to 13 which best describe the data are shown in Table 2.

TABLE 2

Values of pre-exponential factor and energy of activation for Preliminary Model II (self-catalyzed reactions).

| Reaction | k Preexponential factor per gm catalyst basis (kmol i/kgmol n/min) | E Energy of Activation |
|---|---|---|
| CA + EtOH ⇌ MEC + W | 102027711 | 65487 |
| MEC + W ⇌ CA + EtOH | 24292312 | 65487 |
| MEC + EtOH ⇌ DEC + W | 98872409 | 67353 |
| DEC + W ⇌ MEC + EtOH | 82393674 | 67353 |
| DEC + EtOH ⇌ TEC + W | 90076999 | 69647 |
| TEC + W ⇌ DEC + EtOH | 250213886 | 69647 |

It was observed that the correlation between the experimental data and the calculated trend lines is good.

Final Kinetic Model I: Mole Fraction/Concentration-Based Esterification Model Including Both Ion-Exchange Catalyzed and Self Catalyzed Reactions In the third part of this work the ion exchange resin catalyzed reactions have been correlated using a pseudo homogeneous model by considering the rate of the self-catalyzed reactions along with the catalytic reactions. The following expressions were formulated for the overall reaction rate over the entire range of concentration by combining Equations 4 to 6 with Equations 11 to 13:

$$r_{CA,cat} = \left\{ k_{CA,cat} \exp\left(\frac{-Ea_{CA,cat}}{RT}\right) + \right. \quad (14)$$
$$\left. k_{CA,self} \exp\left(\frac{-Ea_{CA,self}}{RT}\right) \left( X_{CA} + \frac{2}{3} X_{MEC} + \frac{1}{3} X_{DEC} \right) \right\}$$
$$\left( X_{CA} X_{EtOH} - \frac{X_{MEC} X_W}{K_{eq,CA}} \right)$$

$$r_{MEC,cat} = \left\{ k_{MEC,cat} \exp\left(\frac{-Ea_{MEC,cat}}{RT}\right) + \right. \quad (15)$$
$$\left. k_{MEC,self} \exp\left(\frac{-Ea_{MEC,self}}{RT}\right) \left( X_{CA} + \frac{2}{3} X_{MEC} + \frac{1}{3} X_{DEC} \right) \right\}$$
$$\left( X_{MEC} X_{EtOH} - \frac{X_{DEC} X_W}{K_{eq,MEC}} \right)$$

$$r_{DEC,cat} = \left\{ k_{DEC,cat} \exp\left(\frac{-Ea_{DEC,cat}}{RT}\right) + \right. \quad (16)$$
$$\left. k_{DEC,self} \exp\left(\frac{-Ea_{DEC,self}}{RT}\right) \left( X_{CA} + \frac{2}{3} X_{MEC} + \frac{1}{3} X_{DEC} \right) \right\}$$
$$\left( X_{DEC} X_{EtOH} - \frac{X_{TEC} X_W}{K_{eq,DEC}} \right)$$

The values of the kinetic parameters in Equations 14 to 16 that best fit the model are shown in Table 3. On comparison of predicted profiles from the earlier Preliminary Model I at 120° C. with the present Final Kinetic Model I that takes into consideration the self-catalyzed reactions, it was observed that the agreement between the predicted concentration profiles and the experimental data is much better for using Final Kinetic Model I where the self-catalyzed reactions have been taken into account, especially for the case where 1% and 2% catalyst has been used.

TABLE 3

Values of pre-exponential factor and energy of activation for Final Kinetic Model I (mole fraction based with both ion exchange catalyzed and self-catalyzed reaction)

| Reaction | k Preexponential factor per gm catalyst basis (kmol i/kgmol n/min) | E Energy of Activation |
|---|---|---|
| CA + EtOH ⇌ MEC + W | 20609598 | 69144 |
| MEC + W ⇌ CA + EtOH | 4907047 | 69144 |
| MEC + EtOH ⇌ DEC + W | 20174482 | 70803 |
| DEC + W ⇌ MEC + EtOH | 16812068 | 70803 |
| DEC + EtOH ⇌ TEC + W | 18060438 | 75294 |
| TEC + W ⇌ DEC + EtOH | 50167883 | 75294 |

However, it is observed that Final Kinetic Model I still does not agree very well in the case of reactions carried out at 78° C., 15:1 initial mole ratio of ethanol to citric acid carried out using 1%, 2% and 3% catalyst.

Final Kinetic Model II: Activity-Based Model for Esterification Including Both Ion-Exchange Catalyzed and Self-Catalyzed Reactions An activity-based kinetic model has been developed using activity coefficients generated in AspenPlus using UNIQUAC and UNIFAC. The self-catalyzed reactions fitted using the UNIQUAC model, which is similar to Eq. 4-6 in form but with activity instead of mole fraction. The kinetic data for the combined self-catalyzed and ion exchange catalyzed esterification reactions was fitted using the UNIQUAC model. The form of the equations is the same as Equations 14-16, except that activity has been substituted for mole fraction in each expression. The fit of the experimental data with the activity model is improved over the case when an activity based model is not used. The fit of the data with the final model is shown in FIGS. 3 to 25. The fit was good. The mole fraction model discussed previously was not as accurate.

Reactive Distillation Experiments

Four reactive distillation experiments were performed for the heterogeneously catalyzed esterification of citric acid with ethanol to produce mono-ethyl, di-ethyl and tri-ethyl citrates and water through the series reactions. In all the runs, 23 wt % citric acid in ethanol was fed 0.2 m from the top of the column (port F1 in FIG. 2) and absolute ethanol 1 m above the reboiler. The experimental details for Runs 1, 2 and 3 are given in Tables 4, 5 and 6 respectively.

TABLE 4

Experimental Conditions and Results for Reactive Distillation RUN 1

| Feed F1: | Citric acid (23 wt % in Ethanol) - 7.02 g/min |
| | Citric acid - 0.0084 mol/min |
| | Ethanol - 0.11 mol/min |
| Feed F2: | Ethanol (Absolute) - 16 g/min - 0.34 mol/min |
| Temp Feed F1: | 25 C. |
| Temp Feed F2: | 85 C. |
| Starting Reboiler Composition: | 1000 ml absolute ethanol |

| Sample No. | Distillate Temp | Bottoms Temp | Citric Acid Conv % | Distillate Composition Wt % Ethanol | Water | Bottoms Composition Wt % Citric Acid | MEC | DEC | TEC | Ethanol | Water |
|---|---|---|---|---|---|---|---|---|---|---|---|
| B1 (9 h) | 78 | 235 | NA | NA | NA | NA | NA | NA | NA | 0.0 | 0.0 |

Notes:
Steady state not achieved

TABLE 5

Experimental Conditions and Results for Reactive Distillation RUN 2

| Feed F1: | Citric acid (23 wt % in Ethanol) - 7.02 g/min |
| | Citric acid - 0.0084 mol/min |
| | Ethanol - 0.11 mol/min |
| Feed F2: | Ethanol (Absolute) - 16 g/min - 0.34 mol/min |
| Temp Feed F1: | 25 C. |
| Temp Feed F2: | 78 C. |
| Starting Reboiler Composition: | 1000 ml from Run 1 |

| Sample No. | Distillate Temp | Bottoms Temp | Citric Acid Conv % | Distillate Composition Wt % Ethanol | Water | Bottoms Composition Wt % Citric Acid | MEC | DEC | TEC | Ethanol | Water |
|---|---|---|---|---|---|---|---|---|---|---|---|
| B1 (9 h) | 78 | 87 | 87 | 98.05 | 1.15 | 8.24 | 18.23 | 13.34 | 2.91 | NA | 0.0 |
| B2 (16 h) | 78 | 87 | 85 | 98.10 | 1.2 | 9.64 | 30.24 | 30.82 | 7.97 | 29.0 | 0.0 |

Notes:
Steady state not achieved.

TABLE 6

Experimental Conditions and Results for Reactive Distillation RUN 3

| Feed F1: | Citric acid (23 wt % in Ethanol) - 20 g/min |
| | Citric acid - 0.023 mol/min |
| | Ethanol - 0.34 mol/min |
| Feed F2: | Ethanol (Absolute) - 15 g/min - 0.32 mol/min |
| Temp Feed F1: | 25 C. |
| Temp Feed F2: | 78 C. |
| Starting Reboiler Composition: | 1000 ml from Run 2 |

TABLE 6-continued

Experimental Conditions and Results for Reactive Distillation RUN 3

| Sample No. | Distillate Temp C. | Bottoms Temp C. | Citric Acid Conv % | Distillate Composition Wt % | | Bottoms Composition Wt % | | | | | |
|---|---|---|---|---|---|---|---|---|---|---|---|
| | | | | Ethanol | Water | Citric Acid | MEC | DEC | TEC | Ethanol | Water |
| B7 (7 h) | 78 | 82 | 40.78 | 98.4 | 0.8 | 13.791 | 9.982 | 2.813 | 0.285 | 73.130 | 0.000 |
| B8 (10 h) | 78 | 82 | 40.99 | 98.4 | 0.74 | 13.499 | 9.838 | 2.741 | 0.330 | 73.603 | 0.000 |

Notes:
Steady state achieved in 6 hours. Four samples were taken after steady state achieved.

Figure 26:
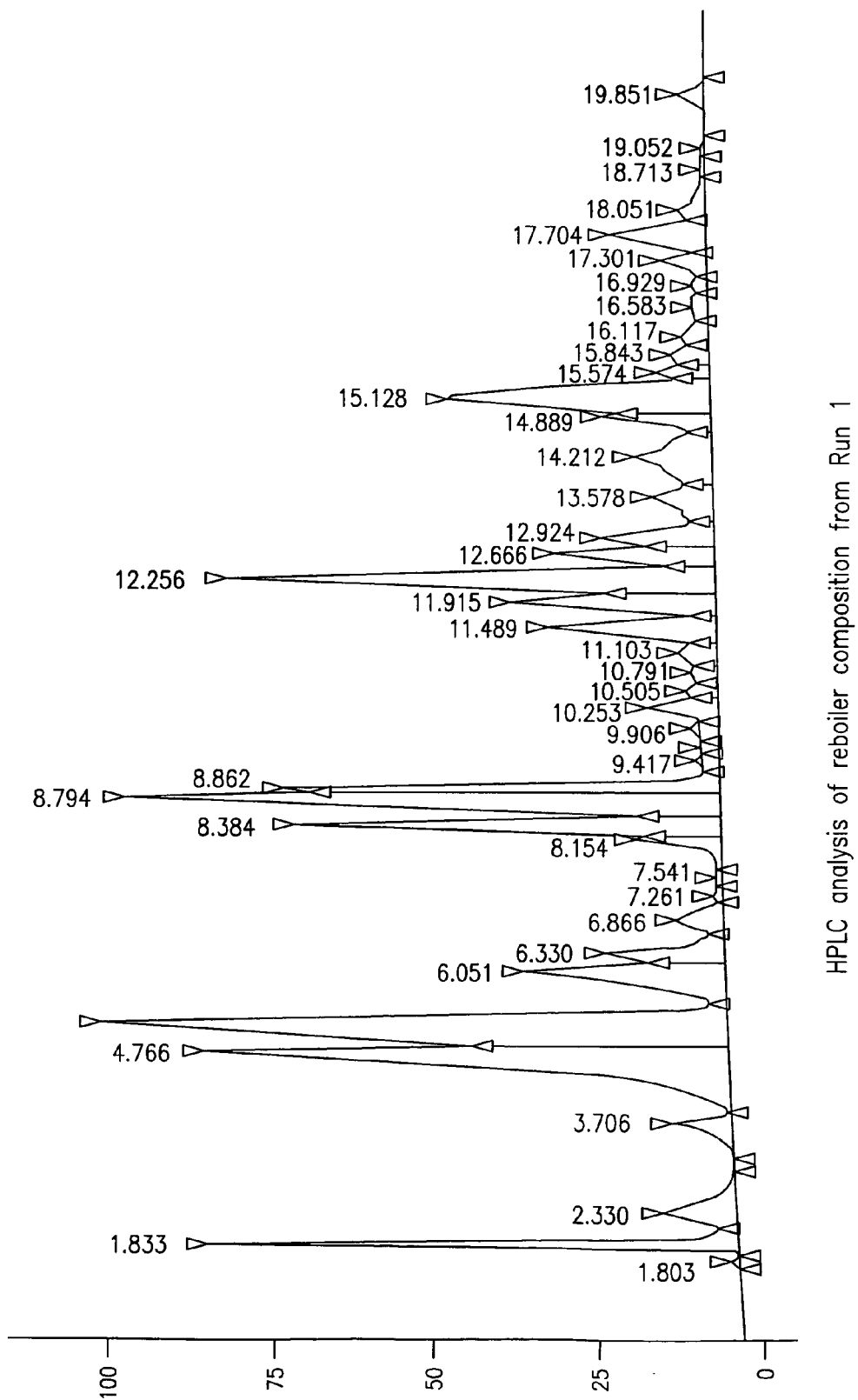
FIG. 26 is a graph showing HPLC analysis of reboiler composition from Run 1.

In Run 1 the column was operated such that the reboiler temperature reached 235° C., indicating that there was no ethanol or water in the reboiler. Under these conditions, significant by-products were formed that included citraconic acid as shown by the HPLC analysis in FIG. 26. It was concluded that a feasible reactive distillation process for triethyl citrate formation requires the presence of ethanol in the reboiler to maintain a relatively low reboiler temperature. The ethanol and esters can be easily separated in a second column, thus eliminating by-product formation in the main reactive column. Results from Run 1 are shown in Table 4.

Figure 27:
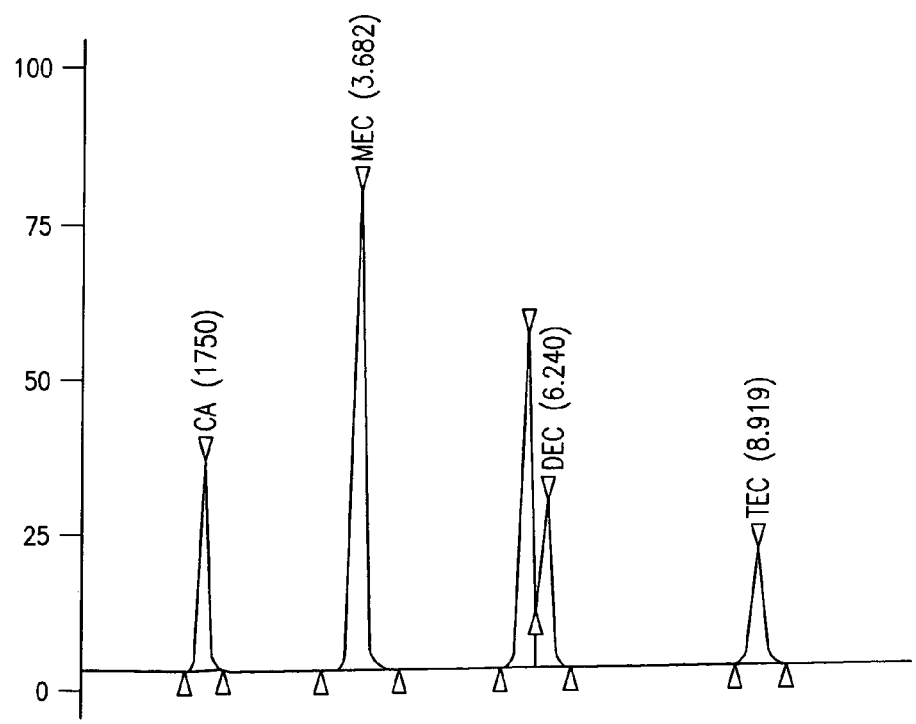
FIG. 27 is a graph showing HPLC analysis of reboiler composition from Run 2.

In Run 2, 29% ethanol was present in the reboiler at steady state. FIG. 27 shows the HPLC analysis of the reboiler composition—there are no detectable byproducts present. A desired reboiler composition of approximately 30% ethanol was chosen as a design and operating parameter for citric acid esterification in order to ensure that no by-products are formed in the reactive distillation column. (Typically this should be between 20 and 40% by volume ethanol). Run 2 did not achieve steady state even after 16 hr of operation because of the low reboiler flow rate, although it was very close to steady state based on samples collected over the course of experiment. Results from Run 2 are shown in Table 5.

Figure 28:
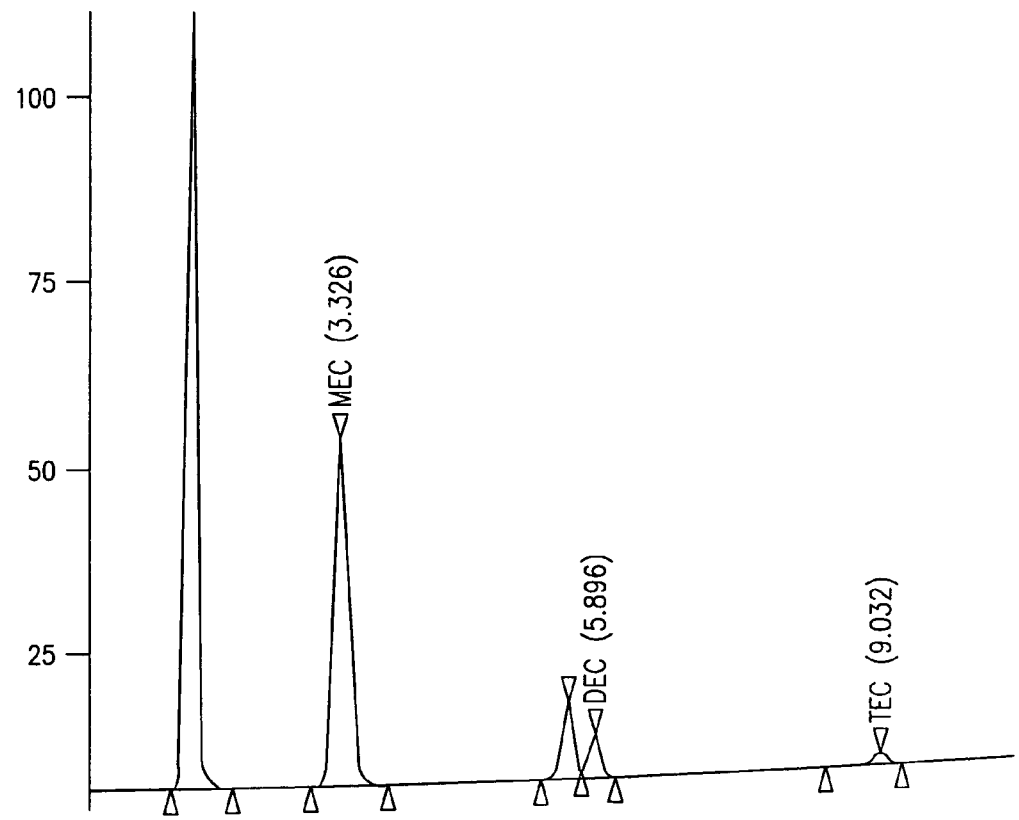
FIG. 28 is a graph showing analysis of reboiler composition from Run 3.

In Run 3, carried out at significantly higher feed rates than in Run 2, a steady state was achieved. FIG. 28 shows the HPLC analysis of the reboiler composition—there are no detectable byproducts present as in the earlier case of Run 2. Results from this run are shown in Table 6, from where it can be seen that a very high concentration of ethanol is present in the reboiler along with a lower conversion of citric acid than that observed in Run 2. Both of these results stem from the higher feed flow rates used in Run 3.

Run 4 was carried out at similar feed conditions to Run 3 except that the ethanol feed was superheated to 84° C. Results from this run are shown in Table 7.

TABLE 7

Experimental Conditions and Results for Reactive Distillation RUN 4

| Feed F1: | Citric acid (23 wt % in Ethanol) - 20 g/min |
| | Citric acid - 0.023 mol/min |
| | Ethanol - 0.34 mol/min |
| Feed F2: | Ethanol (Abolute) - 15 g/min - 0.32 mol/min |
| Temp Feed F1: | 25 C. |
| Temp Feed F2: | 84 C. |
| Starting Reboiler Composition: | 1000 ml from Run 3 |

| Sample No. | Distillate Temp C. | Bottoms Temp C. | Citric Acid Conv % | Distillate Composition Wt % | | Bottoms Composition Wt % | | | | | |
|---|---|---|---|---|---|---|---|---|---|---|---|
| | | | | Ethanol | Water | Citric Acid | MEC | DEC | TEC | Ethanol | Water |
| B (16 h) | 78 | 91 | 61 | 98.2 | 0.96 | 18.2 | 24.6 | 14 | 2.2 | 40.4 | 0.000 |

Notes:
Steady state achieved in 6 hours. Four samples were taken after steady state achieved.

Modeling and Simulation of Pilot Scale Reactive Distillation using Activity Based Model Run 4 of the reactive distillation experiments above are modeled using the RADFRAC module of the ASPEN Plus simulation software to test its accuracy and reliability. The reaction kinetic parameters from the pseudo-homogeneous rate based model described are included in the simulation. The ASPEN-Plus molecule library does not contain mono and di-ethyl citrates, so these compounds were defined using the group contribution method. All other necessary physico-chemical properties used are the default values from ASPEN.

Figure 29:
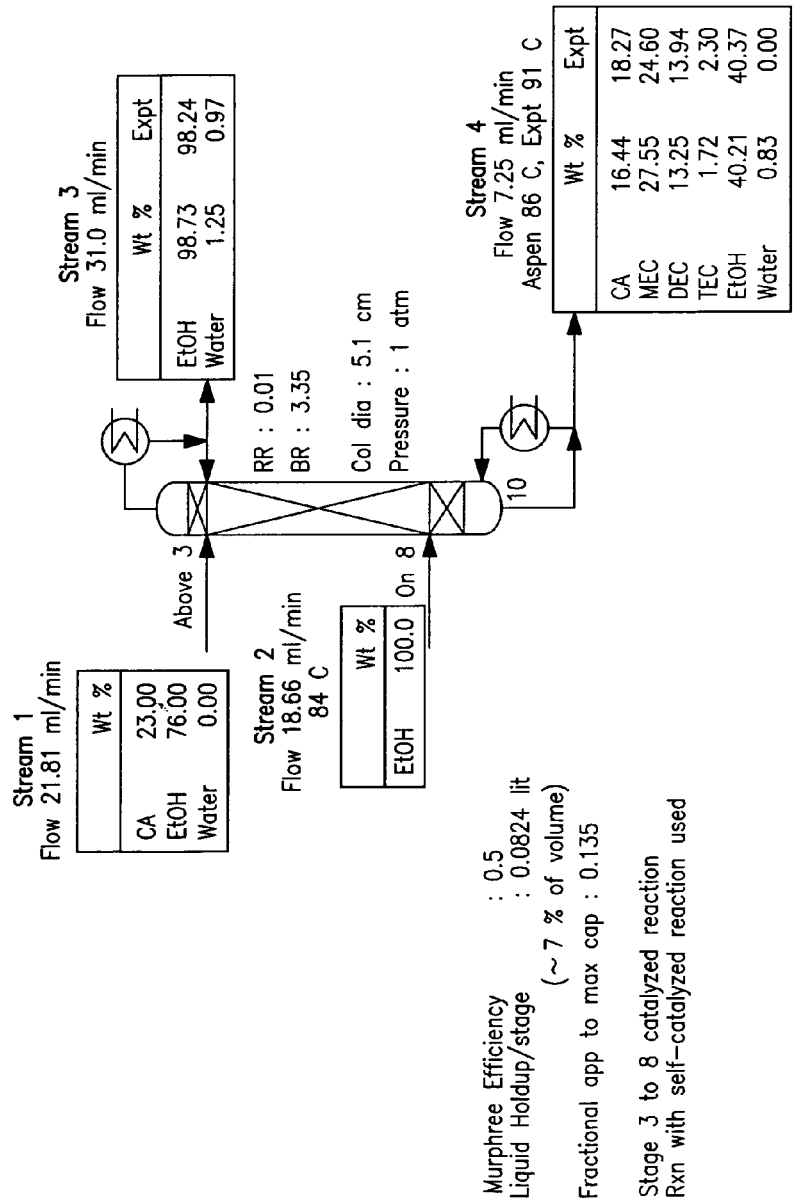
FIG. 29 shows simulation of CA esterification—Pilot scale Run 2.

In the simulation of the experimental pilot scale data, the following parameter values were used:
Reflux ratio—0.01
Total number of stages—10
Feed points—above stage 3 and on stage 8
Reactive stages—3 to 8
Height of stage—0.6
Murphree efficiency—0.5
Liquid holdup per stage—0.0824 lit (~7% of stage volume)
Fractional approach to maximum capacity—0.135
The results from the predictive ASPEN plus simulations are found to be in fair agreement with the experimental data as shown in FIG. 29 for experimental Run 4. The average deviation in species composition is 15%. A lumped wetting efficiency of about 35% was found to fairly represent the experimental data.

Figure 30:
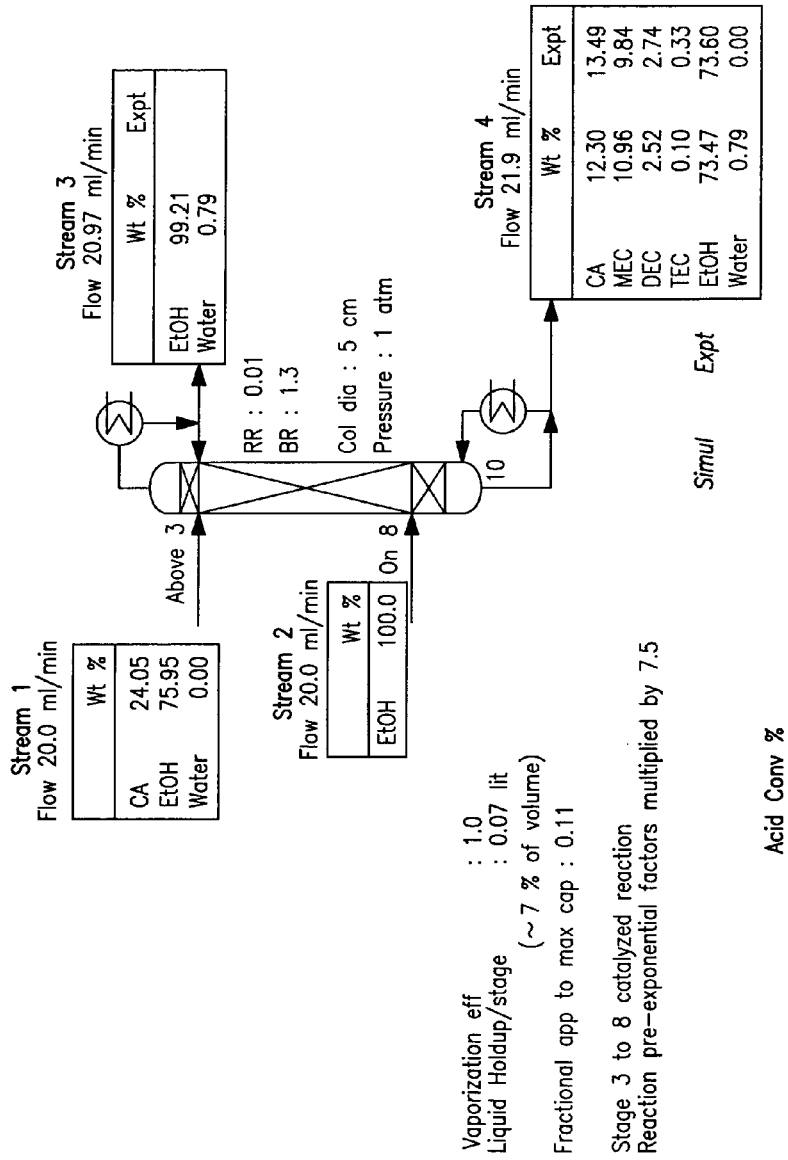
FIG. 30 shows simulation of CA esterification—Pilot scale Run 3.

The results from the predictive ASPEN plus simulations are found to be in fair agreement with the experimental data as shown in FIGS. 29 and 30 for experimental Runs 4 and 3, respectively. The average deviation in species composition is 15%. A lumped multiplication factor of 10.8 was used in case of Run 2 and 7.5 used in case of Run 3 in order to best fit the experimental results. The difference between the two multiplication factors can be possibly attributed to the differences in the catalyst wetting efficiencies. This multiplication factor takes into account the effect of the catalyst loading in the reactive distillation column and the wetting efficiency of the catalyst. The average deviation of about 15% is an acceptable result considering the complexities of the reactive distillation process and the analytical challenges with no internal standards available for the mono-ethyl and di-ethyl citrates.

Figure 31:
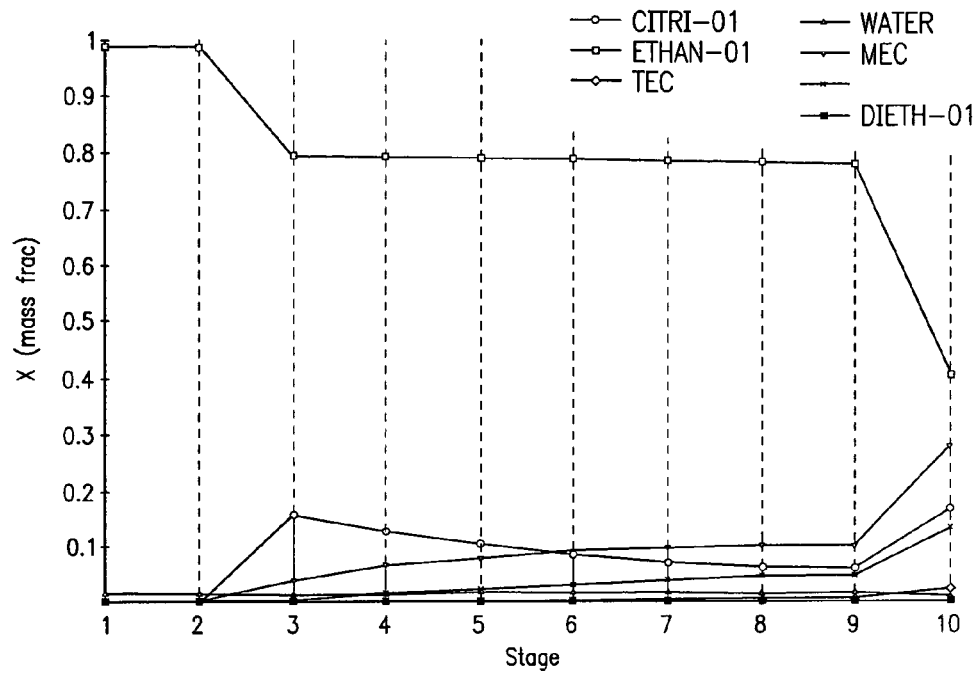
FIG. 31 is a graph showing liquid phase composition profiles for Run 2—ASPEN simulation.
Figure 32:
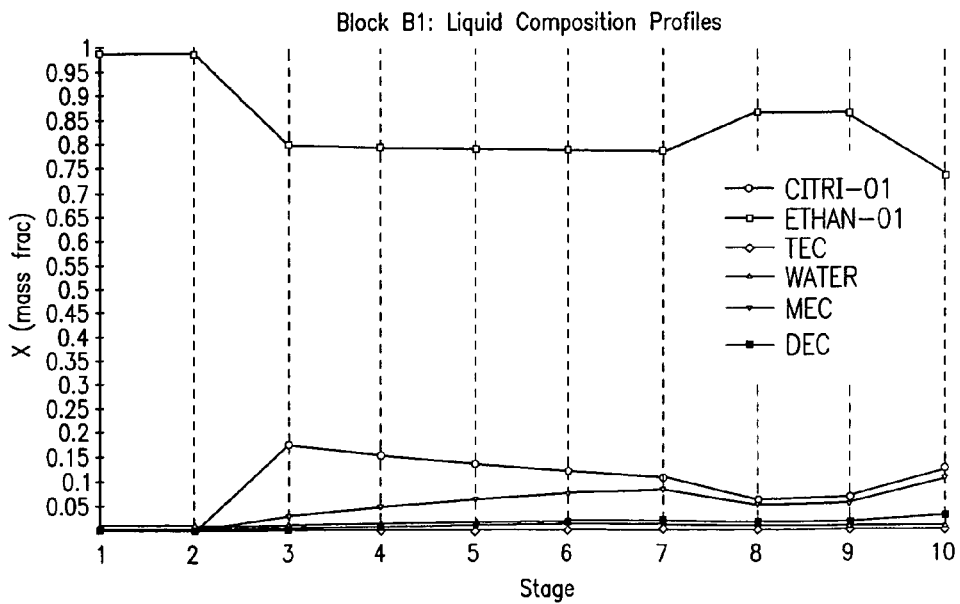
FIG. 32 is a graph showing liquid phase composition profiles for Run 3—ASPEN simulation.

FIGS. 31 and 32 show the liquid phase composition profile in weight % over the column for Runs 4 and 3 respectively. FIG. 33 shows the temperature profile over the column for Run 4. The experimental temperatures of the reboiler and condenser are plotted in the FIG. 33 and the comparison with the predicted temperatures is good.

Proposed Process Scheme for Tri-ethyl Citrate Production

As mentioned earlier in this specification, the experimental yield of tri-ethyl citrate obtained in the pilot-scale reactive distillation column is low because of experimental limitations on column pressure and column height. Therefore, simulation of a commercial-scale process for complete citric acid conversion to tri-ethyl citrate was undertaken to ascertain process feasibility. Citric acid is available commercially in aqueous solution or as anhydrous crystals—clearly use of the aqueous feed is preferable from a cost standpoint.

Three different reactive distillation configurations, shown in FIG. 34, were investigated.

Scheme 1: A stand-alone reactive distillation column which is fed either with an anhydrous saturated citric acid feed in ethanol containing 24 wt % citric acid or an 50 wt % aqueous citric acid feed.

Scheme 2: Feeding a 50 wt % aqueous citric acid feed first to a pre-reactor where a reaction is allowed to go to nearly equilibrium. The outlet from the pre-reactor is then fed to a distillation column where most of the water is distilled out along with ethanol as the overhead. The bottom stream from the distillation column is then fed to a reactive distillation column where the reaction is taken to near completion in order to obtain high yields of tri-ethyl citrate.

Scheme 3: Feeding a 50 wt % aqueous citric acid under similar conditions to Scheme 2 to a pre-reactor. The only difference is that the intermediate distillation column is removed in this configuration. The conversions obtained are compared to that obtained in Scheme 2.

Simulation Results of Extended Pilot-Scale Operation

Results of simulations of the above three Schemes has first been done as an extension of the pilot-scale simulations; e.g., these simulations determine the number of stages that are required to achieve nearly complete citric acid conversion to triethyl citrate at pilot-scale flow rates.

Figure 35:
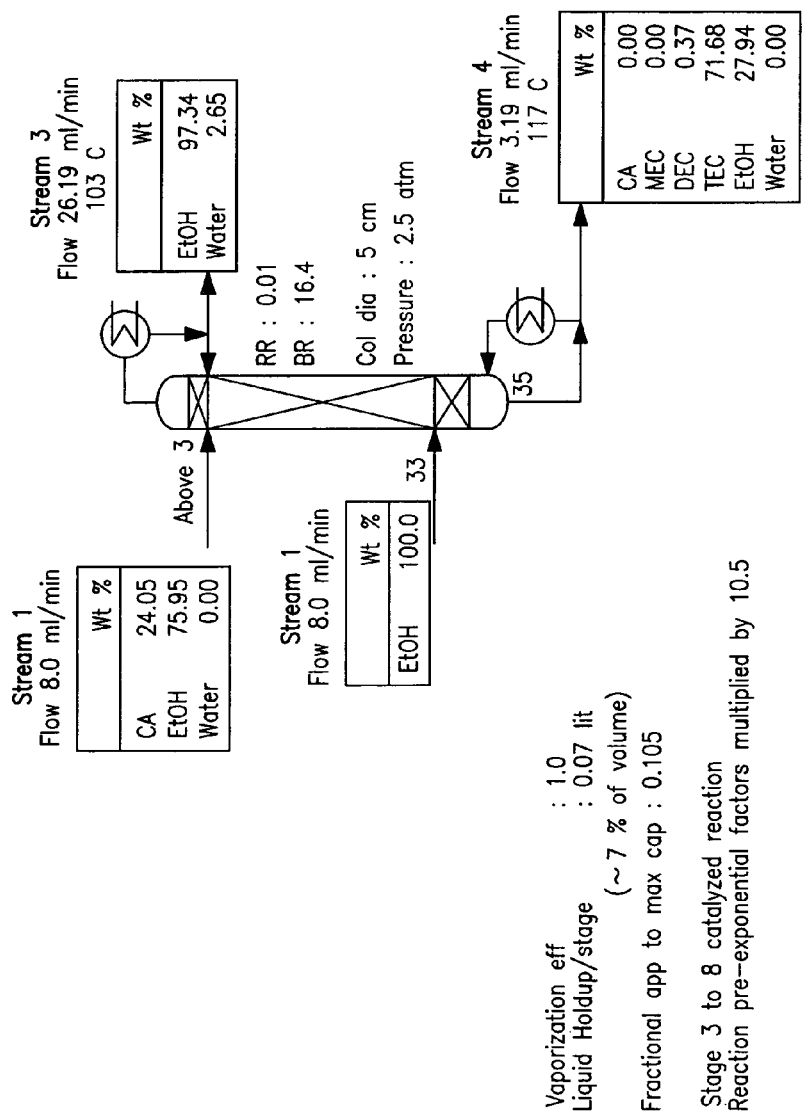
FIG. 35 shows a simulation of anhydrous CA esterification—Pilot scale for complete conversion.
Figure 36:
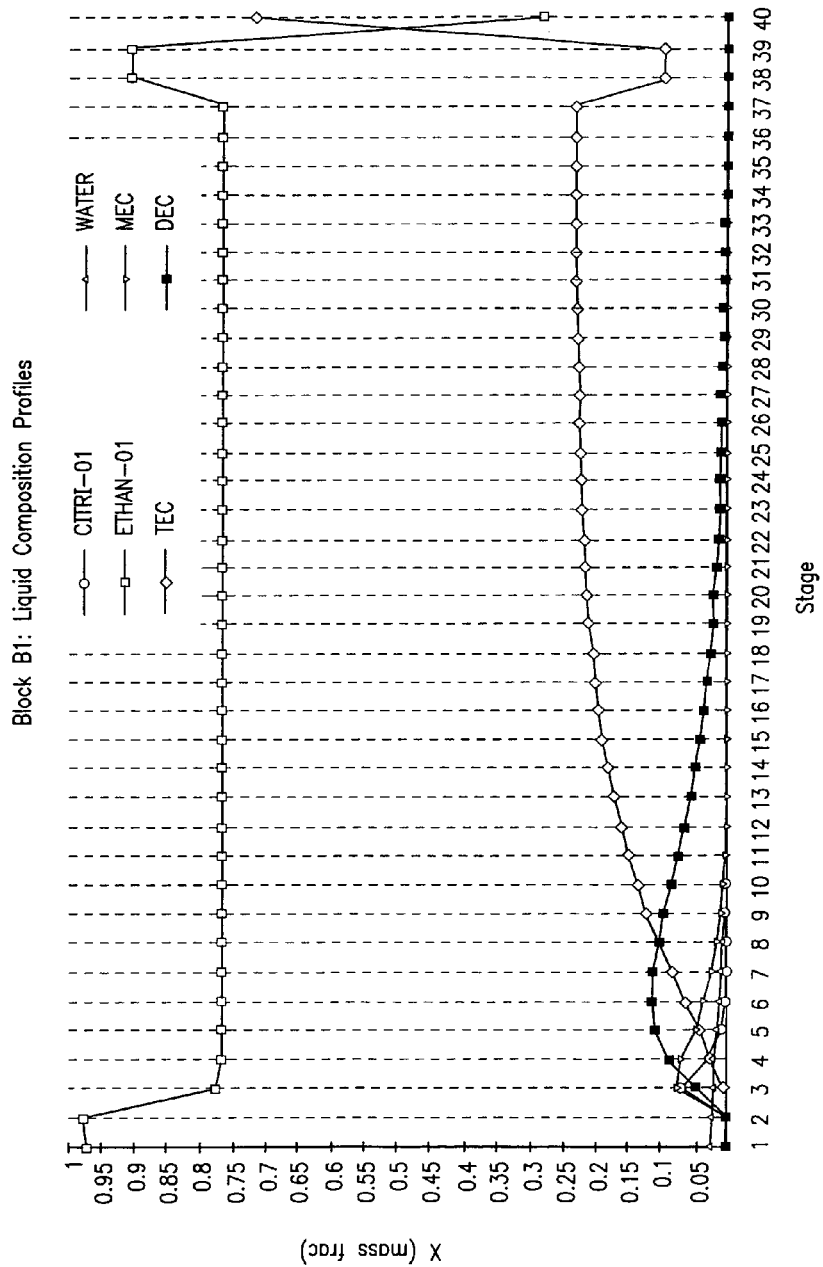
FIG. 36 is a graph showing liquid phase composition profile for anhydrous citric acid feed to obtain complete conversion.

Case 1: FIG. 35 shows the results for reactive distillation using Scheme 1 when anhydrous citric acid in ethanol was fed to a reactive distillation column containing 35 equilibrium stages and operating at 2.5 atm pressure. It can be observed that excellent conversion of citric acid to tri-ethyl citrate is observed at a citric acid flow rate of $5.45 \times 10^{-4}$ kmol/hr. The liquid phase composition profiles (wt %) are shown in FIG. 36. It can be seen from FIG. 24 that conversion of di-ethyl citrate to tri-ethyl citrate is the slowest step in the reactive distillation column, thus requiring a large number of stages to achieve nearly complete conversion.

Figure 37:
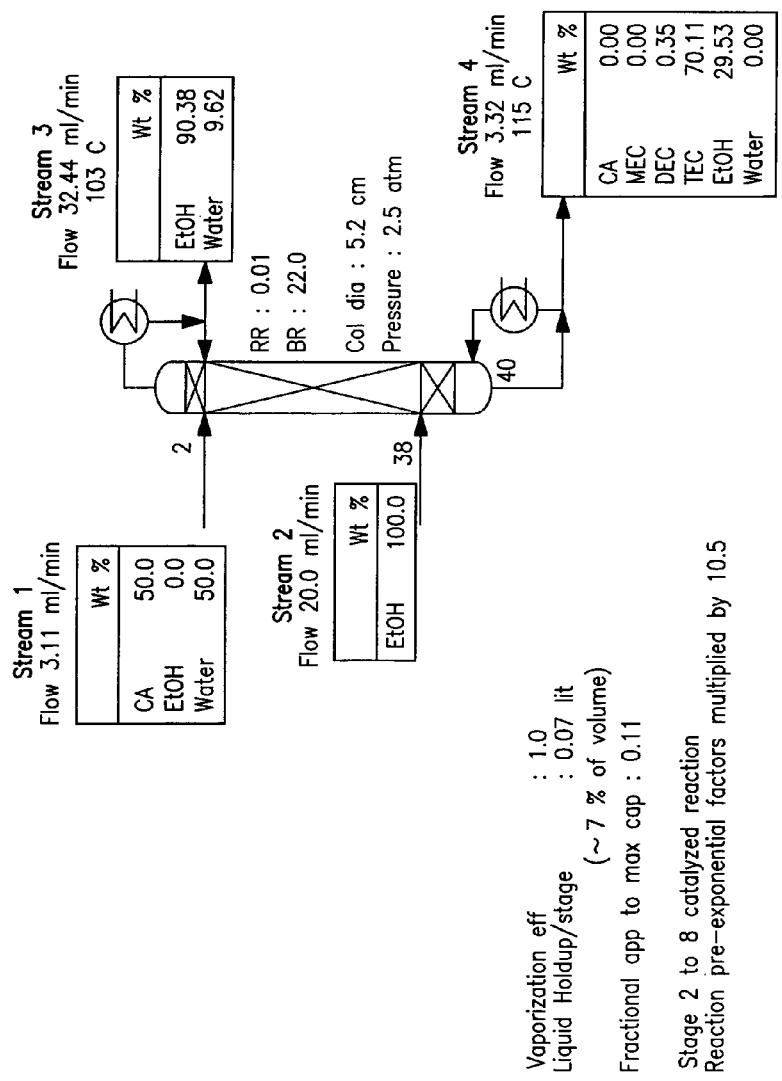
FIG. 37 shows a simulation of aqueous CA esterification—Pilot Scale for complete conversion.
Figure 38:
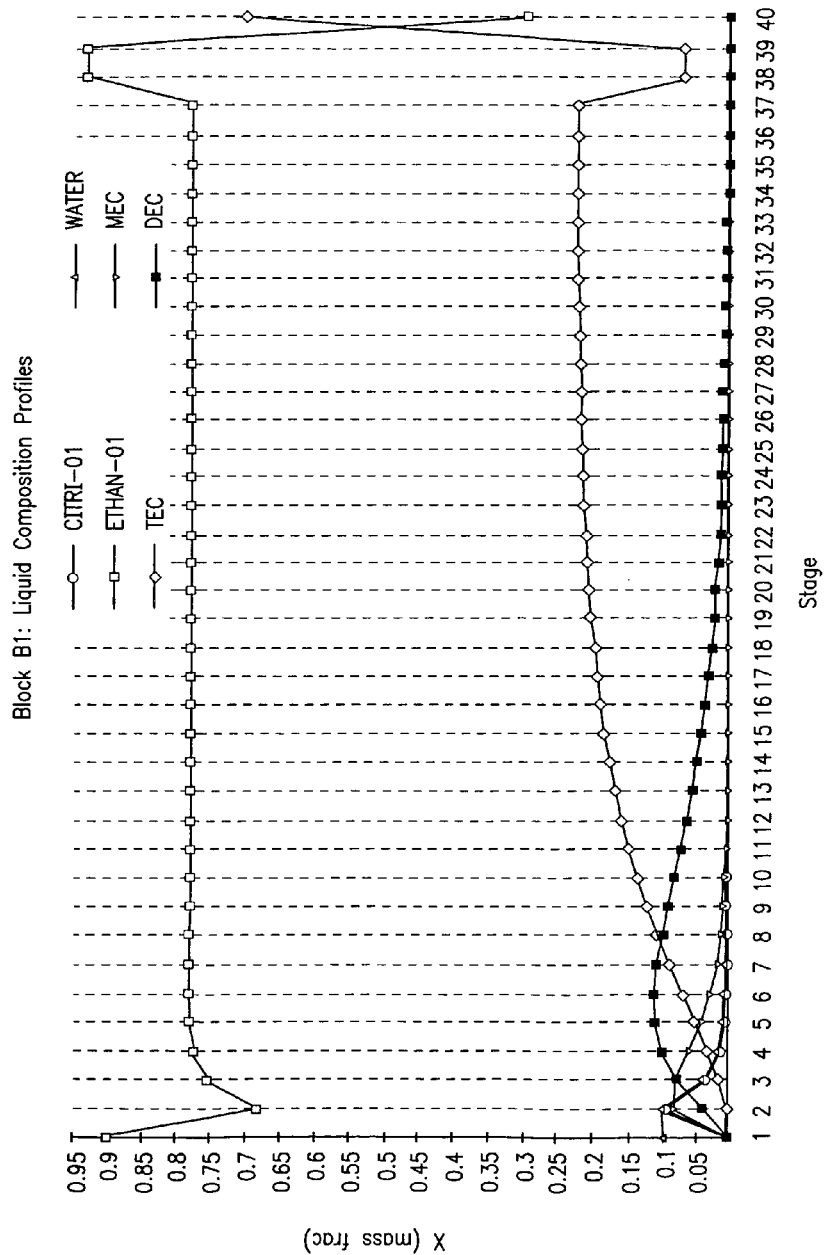
FIG. 38 is a graph showing liquid phase composition profile for aqueous citric acid feed to obtain complete conversion.

Case 2: FIG. 37 shows the results for reactive distillation using Scheme 1 when an aqueous 50 wt % citric acid feed was used as the feed. The column is identical to Case 1 and the citric acid feed rate is $5.45 \times 10^{-4}$ kmol/hr. The liquid phase composition profiles (wt %) are shown in FIG. 38. It was observed that the presence of water in citric acid feed (e.g., the use of aqueous feed versus crystalline citric acid dissolved in ethanol) does not adversely affect the operation of the reactive distillation column, since the water is mostly removed in the initial top stages. Again in this case, it is the conversion of di-ethyl citrate to tri-ethyl citrate that dictates the number of stages required in the reactive distillation column.

Figure 39:
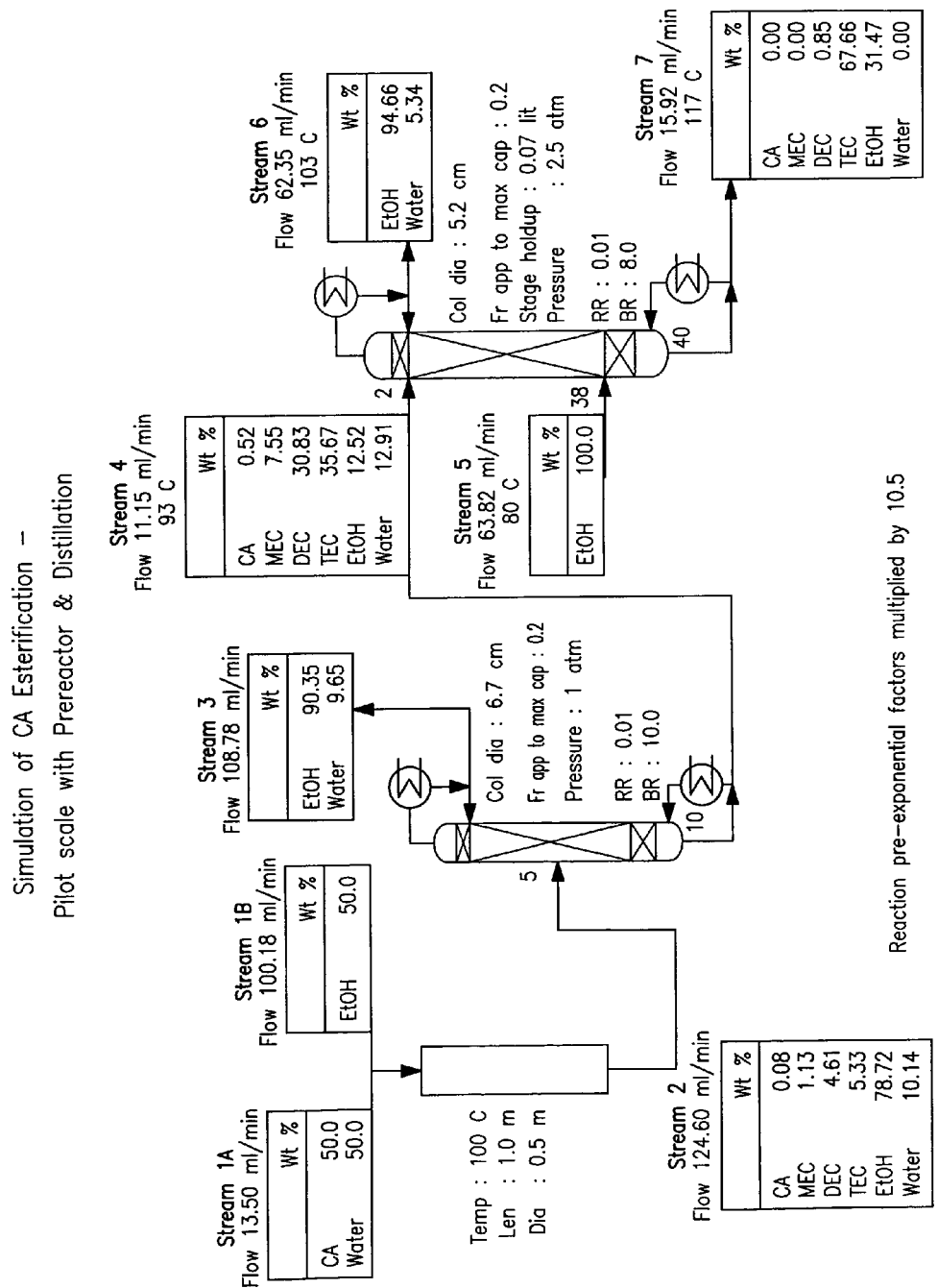
FIG. 39 shows a simulation of CA esterification—Pilot Scale with Prereactor & distillation.

Case 3: Using Scheme 2, $2.49 \times 10^{-3}$ kmol/hr of aqueous citric acid were fed to a plug flow reactor operating as an esterification pre-reactor at 100° C. and 2.0 atm absolute pressure. At these conditions, a conversion close to the equilibrium value is obtained for a reactor space time of approximately 27 hours. The outlet from the plug flow reactor is fed to a simple distillation column of 10 stages operating at 1 atm pressure. About 90% of the water is removed along with ethanol from the distillate. The bottom stream is then fed to a reactive distillation column having 40 stages and operating at 2.5 atm pressure. Nearly complete conversion of citric acid to tri-ethyl citrate is observed under these conditions as shown in FIG. 39.

Figure 40:
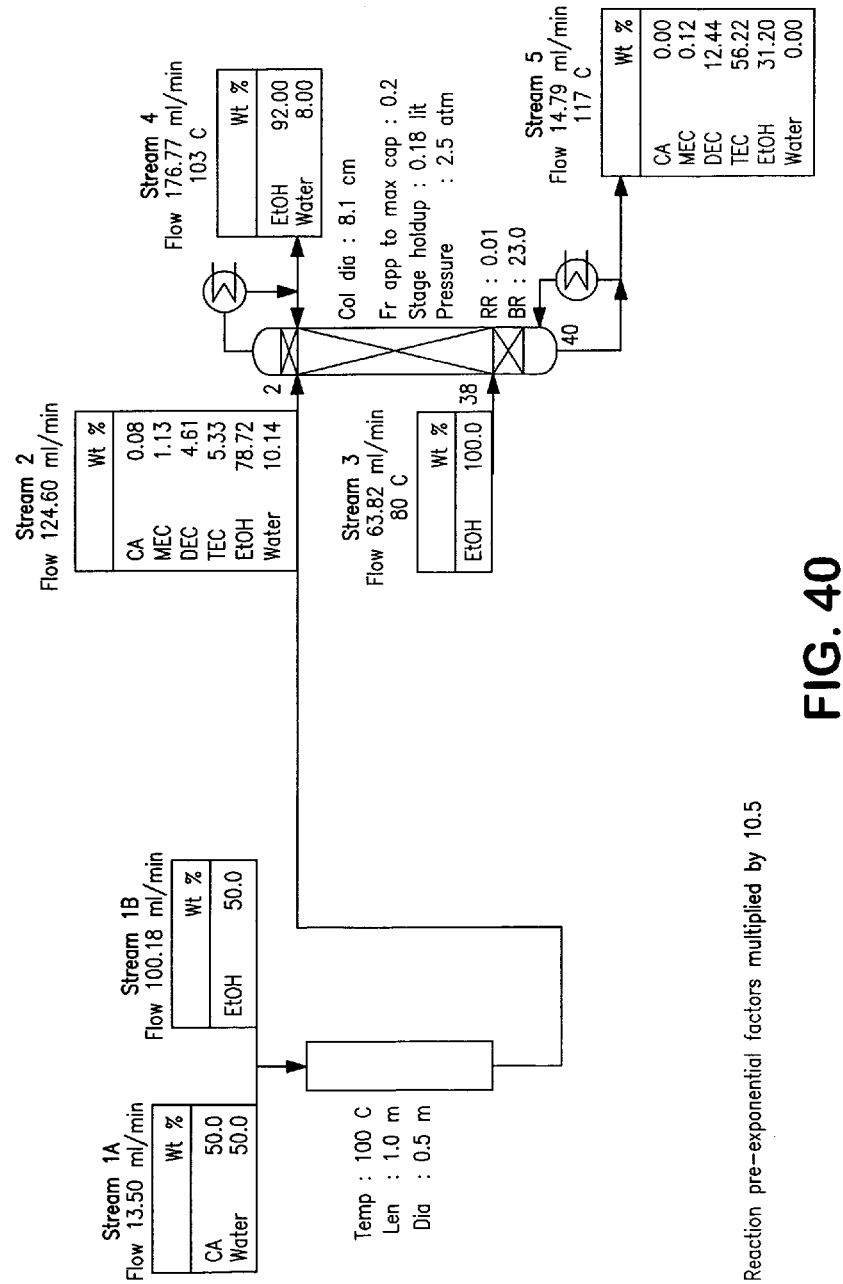
FIG. 40 shows a simulation of CA esterification—Pilot scale with prereactor.

Case 4: The process in this case is similar to that used in Case 3 above, except that the intermediate simple distillation column to remove water and ethanol has been omitted. It can be seen from FIG. 40 that the yield of tri-ethyl citrate in this case is lower than that in Case 3, where the removed water allows higher conversions.

Simulation Results of Commercial-Scale (25 MMlb/yr) Tri-ethyl Citrate Formation

Figure 41:
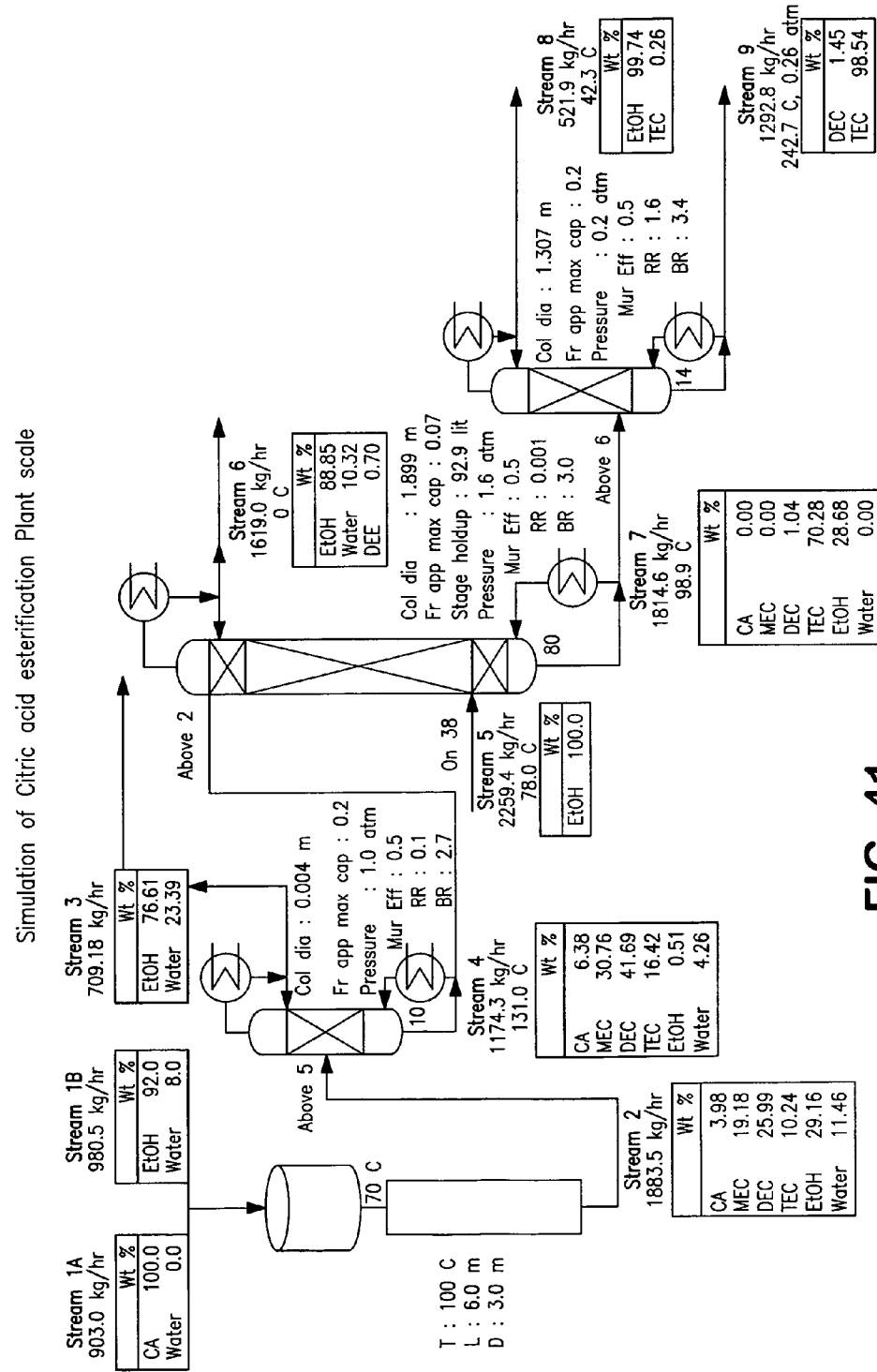
FIG. 41 shows a simulation of CA esterification—plant scale with prereactor & distillation.
Figure 42:
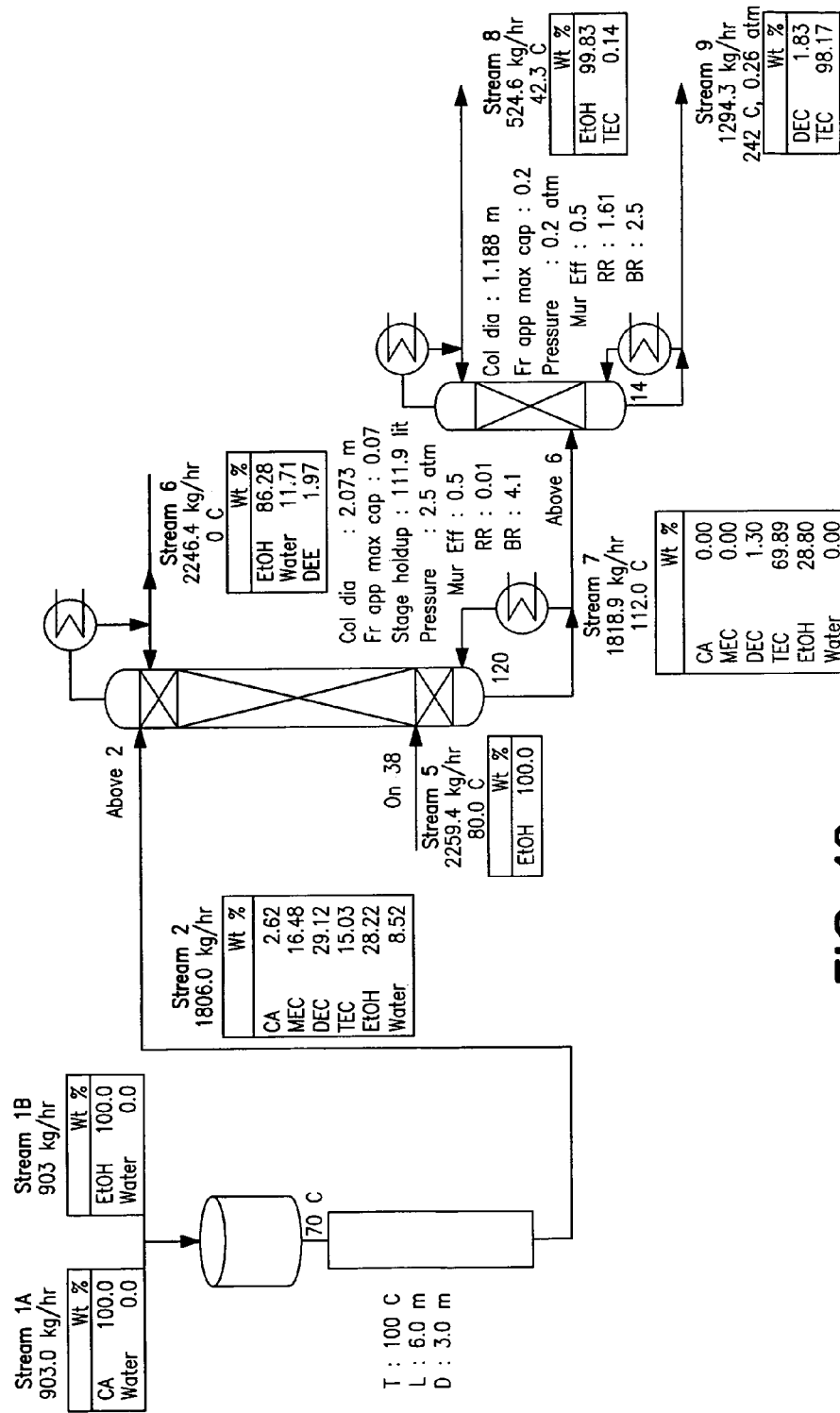
FIG. 42 shows a simulation of CA esterification—plant scale with prereactor & distillation.
Figure 43:
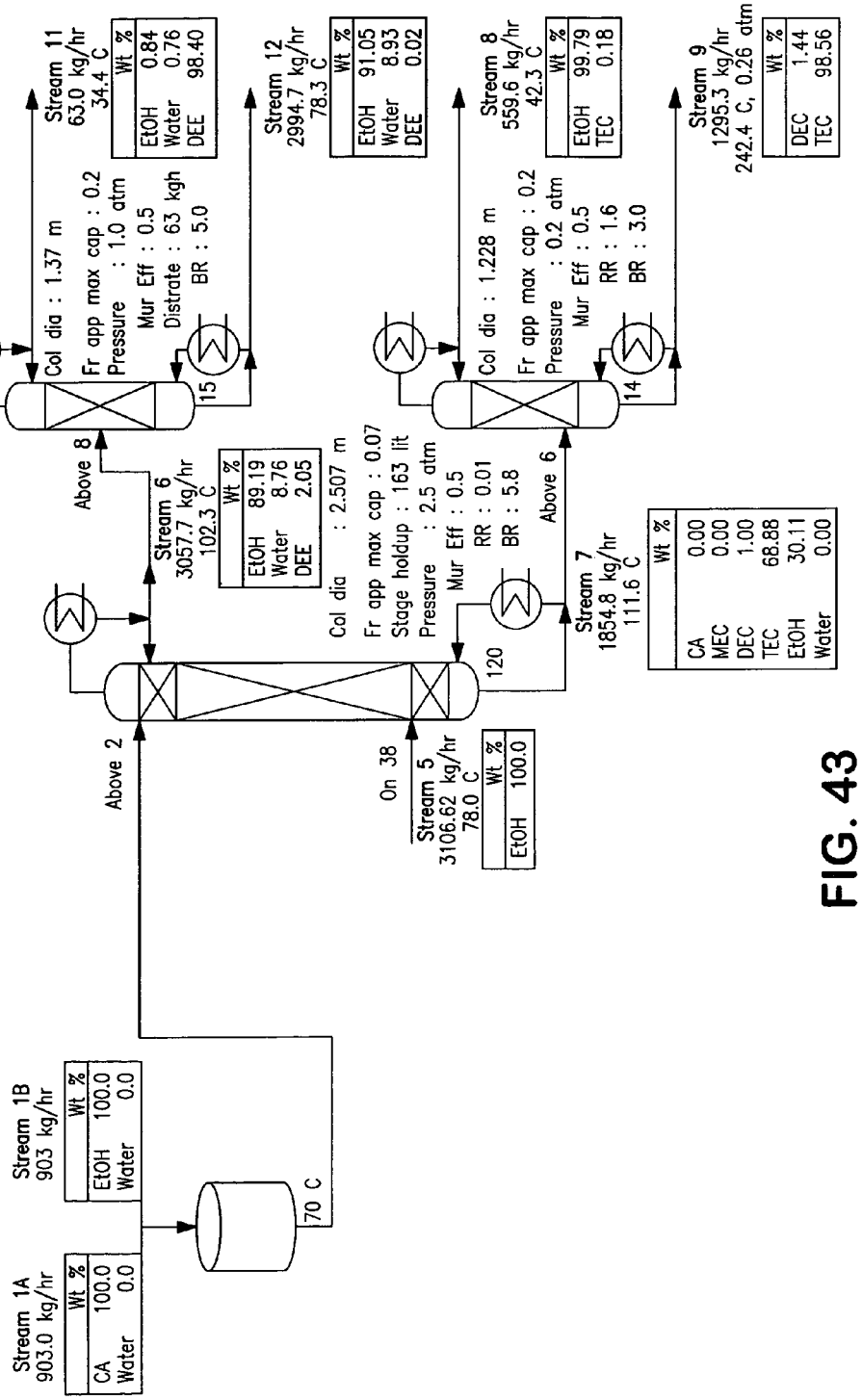
FIG. 43 shows a simulation of CA esterification—plant scale with prereactor & distillation.
Figure 44:
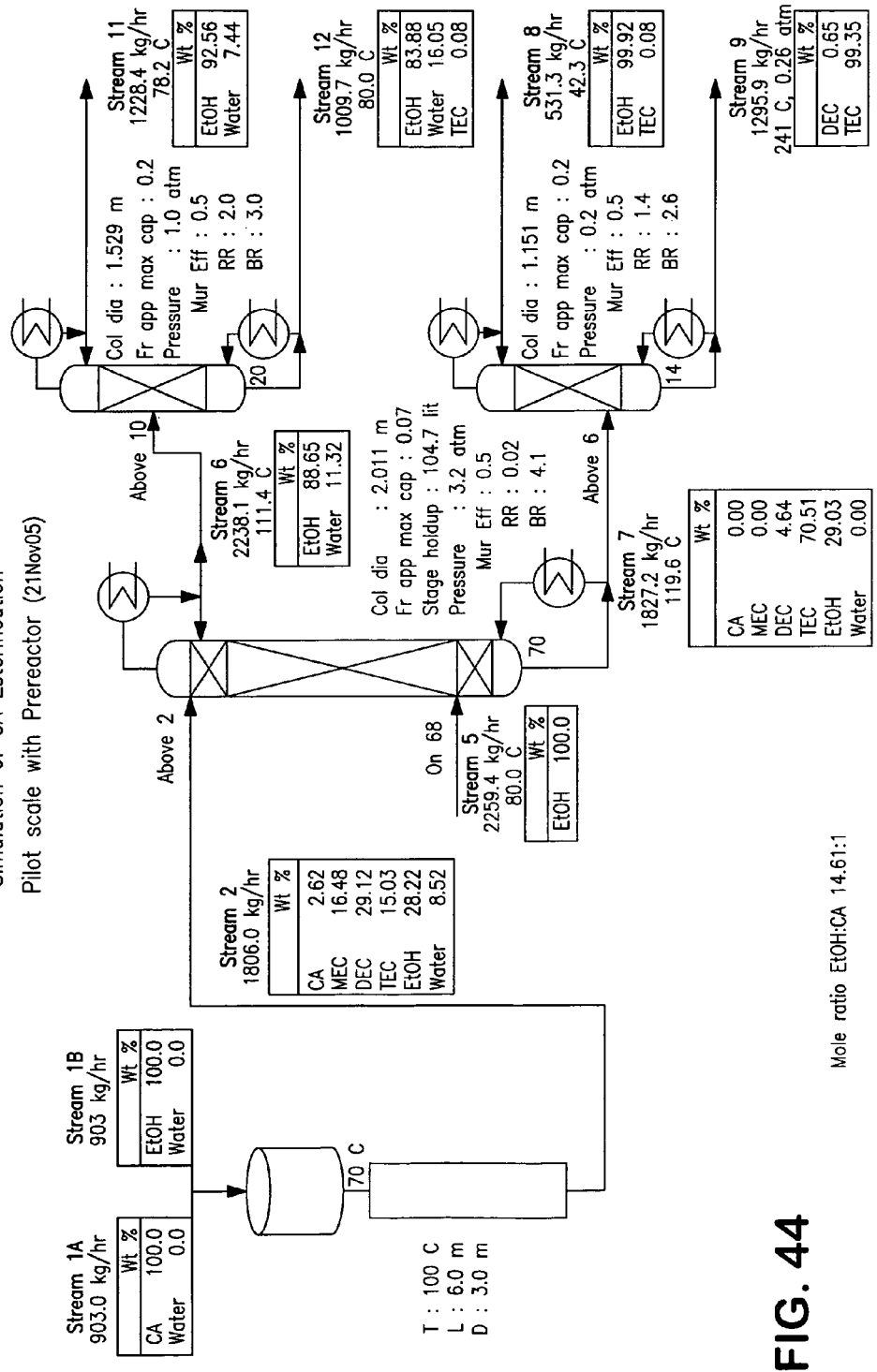
FIG. 44 shows a simulation of CA esterification—plant scale with prereactor.
Figure 45:
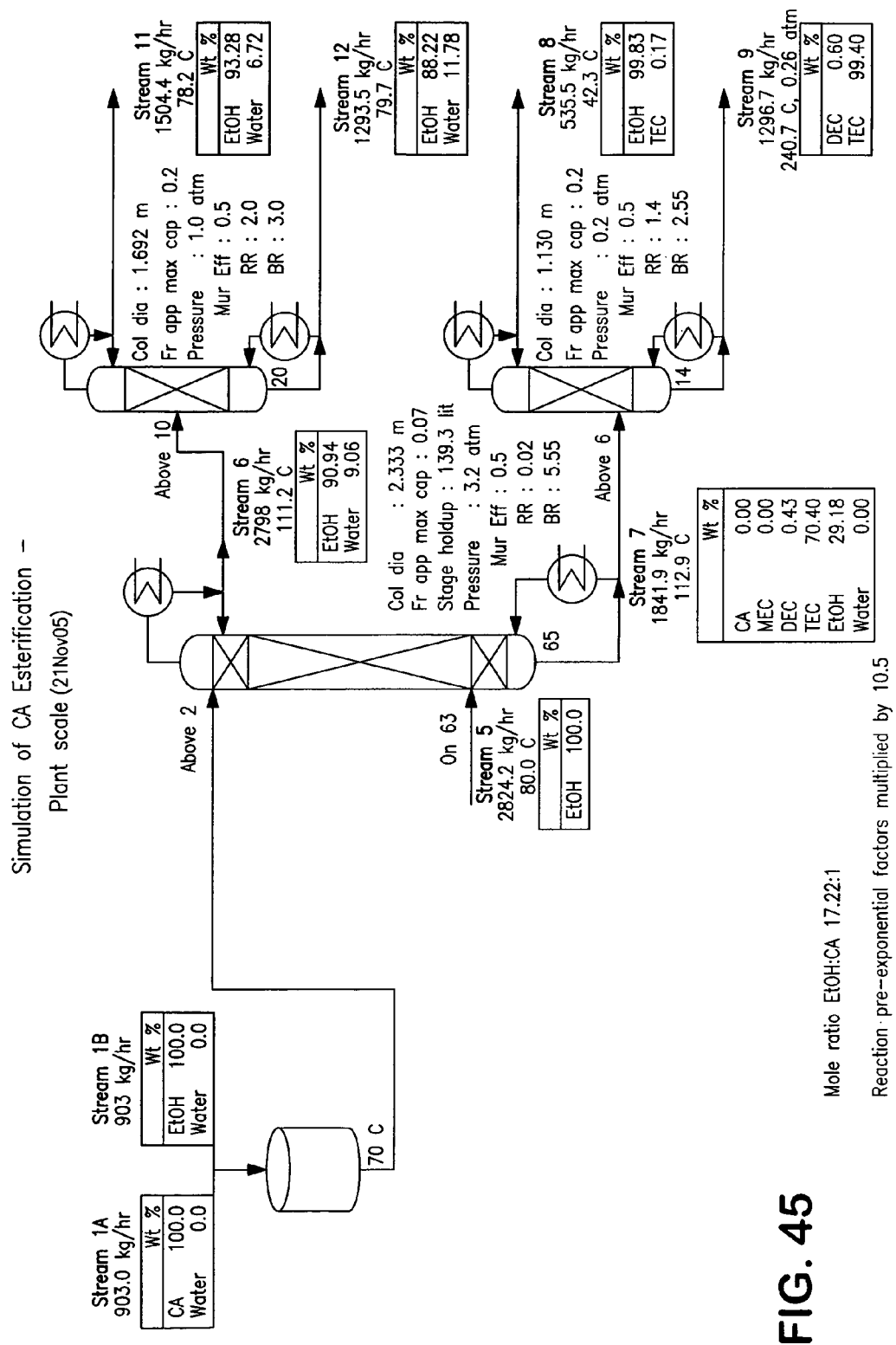
FIG. 45 shows a simulation of CA esterification—plant scale
Figure 46:
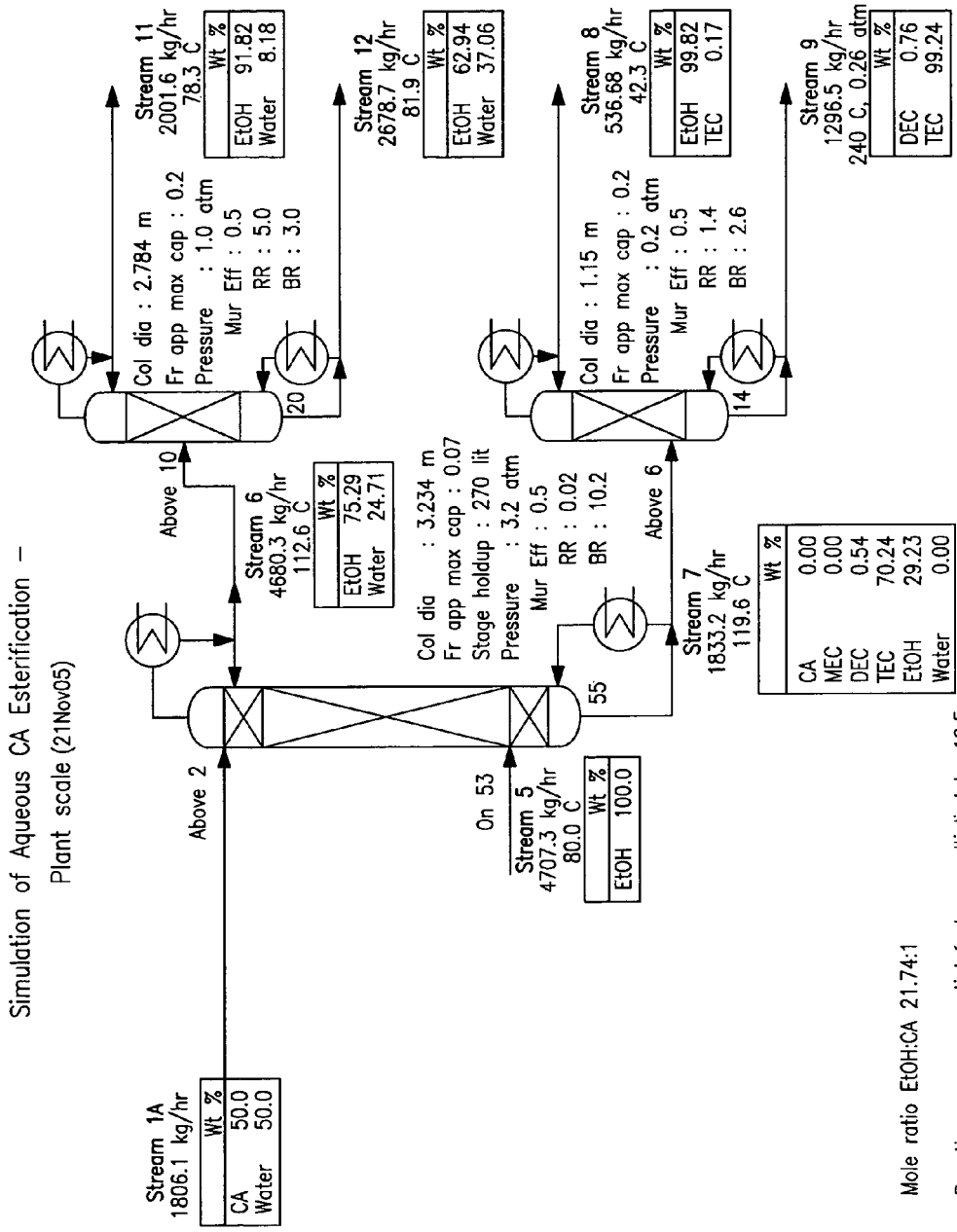
FIG. 46 shows simulation of aqueous CA esterification—plant scale.

Three different cases, based on Schemes 1-3 in FIG. 34, were studied for the synthesis of 25 million lb/annum of tri-ethyl citrate. To achieve this, a citric acid feed of 903 kg/hr has been used in all the calculations. These simulations differ from those in the above section in that commercial-scale flow rates were used in all simulations. The assumptions made in all the process flow schemes are detailed below. FIGS. 41 to 43 show the various configurations and results for commercial-scale synthesis of ethyl citrate using final kinetic Model I in the simulation. FIGS. 44 to 46 show the various configurations and results for commercial scale synthesis of ethyl citrate using final kinetic Model II involving activity instead of mole fraction. Reactive Distillation Column Total condenser was considered with Condenser pressure set between 1.6 to 2.5 atm Stage 2 pressure was set between 1.6 to 2.5 atm Column pressure drop of 0.05 atm was considered Murphree Efficiency was set to 0.5

Liquid holdup per stage was set to approximately 5.5 to 6% of the stage volume

All the reactive and non-reactive stages in the column were considered to be of type KERAPAK, Vendor Sulzer, Material—Standard, Size—Standard HETP was set to 0.6

Fractional approach to maximum capacity—0.07

If the reactive distillation is performed at atmospheric pressure (1 atmosphere) then the temperature of the reboiler needs to be less than 120° C. to prevent formation of by-products. If the pressure is elevated then higher temperatures can be used up to about 150° C. can be used. Thus pressures up to 20 atmospheres can be used.

The possible permutations of process layouts and operating parameters in potential citric acid esterification reactive distillation process can be overwhelming. In order to achieve an optimized layout and operating conditions for an industrial scale reactive distillation column, laboratory and pilot scale experimental results were combined with process simulation modeling to minimize the volume of experimental data yet maintain highly credible design.

ASPEN Plus is the most widely used simulation software in the chemical process industry. The software has desirable features which include the built-in module RADFRAC for simulation of reactive distillation processes. RADFRAC has the ability to simulate phase equilibria simultaneously with chemical equilibria or with incorporation of reaction kinetic data, the latter requiring estimation of liquid residence time or liquid holdup on each stage of the distillation column. The details of the RADFRAC algorithm used for simulation of reactive distillation systems are described in detail by Venkataraman et al., Reactive Distillation using ASPEN Plus., Chem. Eng. Prog., (1990), 69, 45-54. ASPEN Plus is further supported by a strong physical and chemical properties database, including hydrodynamics of column packings such as those used in our laboratory, and the ability to predict properties of components not present in the database. Both equilibrium-based and kinetic-based chemical reaction models have been incorporated in the current study.

There has been no prior study on the application of reactive distillation for citrate esters formation, and no information is available in the open literature on the kinetics of citric acid esterification with ethanol in presence of ion exchange resins as catalysts. Therefore, the present work has been carried out with the goal of developing a favorable reactive distillation configuration to obtain high citric acid conversion and high selectivity to tri-ethyl citrate. Results are presented here on three related efforts: (1) batch esterification of citric acid in glass or autoclave reactors, from which a pseudo-homogenous kinetic model of the citric acid esterification system has been developed; (2) continuous citric acid esterification experiments in a pilot-scale packed reactive distillation column operating at 1 atm; and (3) simulation of the pilot-scale reactive distillation column and of a commercial-scale reactive distillation process for citric acid esterification using ASPEN Plus process simulation software with the experimentally developed kinetic model. Commercial-scale simulations have been conducted with and without use of an esterification pre-reactor and an intermediate simple distillation column in order to obtain high yield of tri-ethyl citrate.

TRIBUTYL CITRATE EXAMPLES

Tri-Butyl Citrate Formation in RD Column

Esterification of citric acid was carried out with n-butanol in an autoclave (used as a pre-reactor) at 120° C. to achieve an equilibrium composition of mono-, di-, and tri-butyl citrate esters. The operating temperature was limited to 120° C. by the thermal instability of the catalyst (Amberlyst-15). In a typical reaction, 0.15 mol of citric acid was reacted with 2.25 mol of n-butanol (15:1 ratio) in the presence of Amberlyst-15 resin as catalyst. The catalyst quantity was maintained at a loading of 5 wt % of total mass of reactants. Equilibrium was achieved after 16 h of reaction with almost 99% conversion of citric acid; the distribution of various esters was 4% mono-, 30% di-, and 65% tri-butyl citrate.

The final reaction mass obtained at equilibrium was used as a feed for reactive distillation. The equilibrium composition of butyl citrate esters was fed to the upper port in the column while an excess of n-butanol was fed through lower port of column. The objective of this Example was to achieve complete removal of water (reaction product) through the distillate and 100% formation of tri-butyl citrate in the bottoms product stream. No water was observed in the bottoms product stream, while the distillate showed the presence of water and n-butanol. Water and n-butanol form an azeotrope, which helps in removing the water from the reaction zone. The composition of butyl citrate esters in the bottoms product stream at steady state was 24 di- and 76% tri-butyl citrates. No monobutyl citrate was observed. Formation of di-butyl ether via condensation reaction of n-butanol was also observed but in very small quantity. This experiment illustrates the formation of tributyl citrate ester via reactive distillation. The results are shown in Table 8.

Reaction Conditions:

Feed F1: Citric acid+n-Butanol (Equilibrium reaction mixture)=7.2 g/min Feed in wt % (CA: 0; MBC: 0.82; DBC: 7.02; TBC: 17.36; BuOH: 77.35; Butyl Ether: 0.5; Water: 1.66)

Note: 100% Citric acid conversion

Feed F2: n-Butanol=16 g/min=0.21 mol/min

Reboiler content: 1000 ml of n-Butanol

F1 Feed temperature=25° C.

F2 Feed Temperature=25° C.

At Steady-state after 16 h

Reboiler composition (B=Flow rate=15.33 g/min)

Distillate Composition (T=Flow rate=7.80 g/min)

TABLE 8

| | Product distribution in wt % (mol %) | | | | | | |
|---|---|---|---|---|---|---|---|
| Sample | MBC | DBC | TBC | $Bu_2O$ | Water | BuOH | Temp. |
| B4 | 0 | 3.3 (0.86) | 11.7 (2.59) | 0 | 0.86 (3.84) | 86 (92.6) | 102 |
| T4 | 0 | 0 | 0 | 1.5 (6.8) | 1.74 (6.4) | 96.7 (86.7) | |

Diethyl Succinate Example

Figure 47:
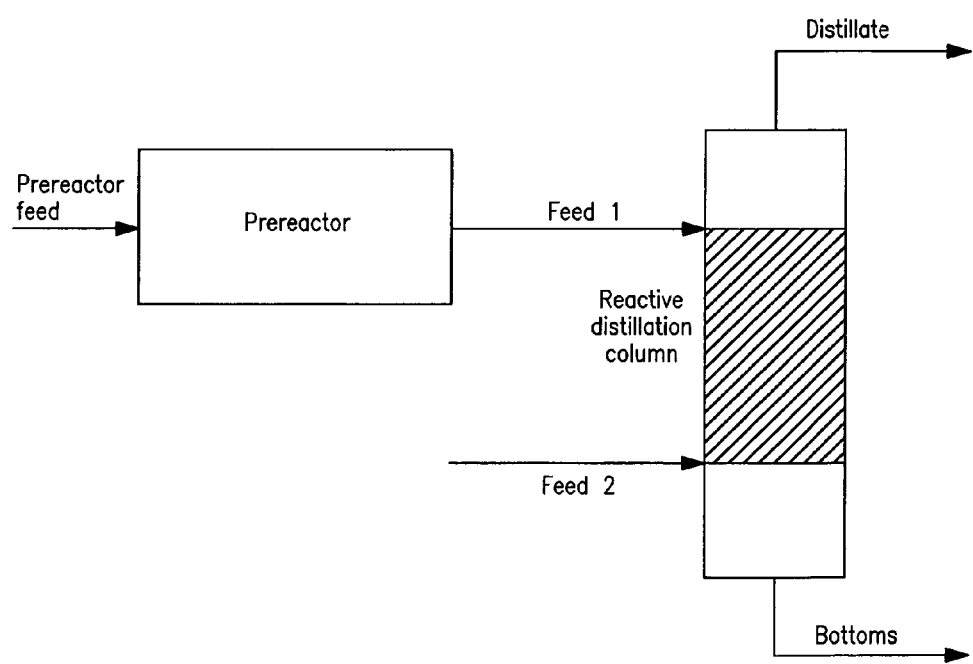
FIG. 47 is a schematic of experiment for Succinic Acid Esterification via Reactive Distillation.

The reactive distillation experiment for esterification of succinic acid used a prereactor at 120° C. to produce Feed 1 stream from the prereactor stream as shown in FIG. 47. The prereactor feed constitutes a 10:1 molar ratio of ethanol to succinic acid. The stream Feed 1 represents an equilibrium mixture. In the reactive distillation column, the conversion of residual succinic acid (SA) from Feed 1 is about 45%. Monoethyl succinate (MES) is also about 50% converted in the RD column to produce additional diethyl succinate, the desired final product. The results of this Example shown in Table 9 illustrate the capability of reactive distillation to produce diethyl succinate from succinic acid.

TABLE 9

Results of Succinic Acid Esterification via Reactive Distillation
(All values are species flow rates in g/min)

| Species | Prereactor | Feed 1 | Feed 2 | Distillate | Bottoms |
|---|---|---|---|---|---|
| Succinic acid | 4.1 | 0.2 | 0 | 0 | 0.119 |
| Monoethyl succinate | | 1.03 | 0 | 0 | 0.514 |
| Diethyl succinate | | 4.73 | 0 | 0 | 5.39 |
| EtOH | 15.9 | 12.66 | 15 | 19.42 | 8.05 |
| Water | | 1.29 | 0 | 1.36 | 0 |
| Diethyl ether | | 0.096 | 0 | 0.10 | 0 |
| TOTAL | 20.0 | 20.0 | 15.0 | 20.9 | 14.1 |

The person of skill in the art would recognize that the present invention can be applied to esterify organic acids besides citric acid, including other biomass-derived acids such as succinic acid, propionic acid, malic, glutaric, adipic, glyceric, 3-hydroxy propanoic, lactic, levulinic, and amino acids such as alanine, serine, glycine and lysine.

It is intended that the foregoing description be only illustrative of the present invention and that the present invention be limited only by the hereinafter appended claims.

We claim:

1. A process for the continuous esterification of citric acid to produce a citric acid tri-ester in a vertical column by reactive distillation and to reduce by-products comprising:
    (a) feeding a mixture comprising the citric acid as an aqueous or alcoholic solution into an upper port of the column and an alcohol containing 1 to 8 carbon atoms into a lower port of the column;
    (b) contacting in a reactive distillation the citric acid and the alcohol in countercurrent flow in a reaction zone between the ports at a temperature between 80 and 120° C. which reacts the citric acid and the alcohol over an insoluble acid catalyst, wherein the catalyst is: (i) mounted in structured packing elements and (ii) supported in the column as a single unit of the structured packing elements within the reaction zone to form the citric acid tri-ester;
    (c) removing vaporized unreacted alcohol and water from the top of the column;
    (d) collecting a product comprising the citric acid ester from the bottom of the column, wherein the citric acid ester is mixed with about 20 to 40% by volume of the alcohol and is reboiled in a reboiler in part into the bottom of the column and in part collected as the alcohol and the citric acid ester, and wherein the reboiler is maintained at a temperature such that the presence of alcohol exists in the composition in the reboiler and the reboiled composition maintains the temperature at the bottom of the column below a temperature that causes the citric acid or the citric acid esters to form byproducts;
    wherein the feeding of the alcohol relative to the feeding of the citric acid is such that the percentage of citric acid conversion to a tri-ester is greater than 50 percent.

2. The process of claim 1 wherein the vaporized unreacted alcohol removed from the top of the column is recovered and recycled into the lower port of the column.

3. The process of claim 1 wherein the insoluble acid catalyst is an acidic ion exchange resin.

4. The process of claim 1 wherein the feeding of the alcohol relative to the citric acid is such that a molar ratio of alcohol to citric acid is provided between about 5:1 and 20:1.

5. A process for the continuous esterification of citric acid to produce a citric acid tri-ester in a single vertical column by reactive distillation comprising:
    (a) feeding a mixture of citric acid containing about 50 to 90% by weight of an alcohol containing 1 to 8 carbon atoms into an upper port of the column and the alcohol into a lower port of the column;
    (b) contacting in a reactive distillation the citric acid and the alcohol in countercurrent flow in a reaction zone between the ports at a temperature which reacts the citric acid and the alcohol over an insoluble acid catalyst, wherein the catalyst is: (i) mounted in structured packing elements and (ii) supported in the column as a single unit of the structured packing elements within the reaction zone to form the citric acid tri-ester;
    (c) removing vaporized unreacted alcohol and water from the top of the column;
    (d) collecting a product comprising the citric acid ester from the bottom of the column, wherein the citric acid ester formed is partially reboiled in a reboiler in part into the bottom of the column and in part collected as a mixture of the alcohol and the organic acid ester from the reboiler and wherein the reboiler is maintained at a temperature such that the presence of alcohol exists in the composition in the reboiler and the reboiled composition maintains the temperature at the bottom of the column below a temperature that causes the citric acid or the citric acid esters to form byproducts; and
    (e) separating the collected alcohol from the organic acid ester removed from the reboiler;
    wherein the feeding of the alcohol relative to the feeding of the citric acid is such that the percentage of citric acid conversion to a tri-ester is greater than 50 percent.

6. The process of claim 5 wherein the vaporized unreacted alcohol removed from the top of the column is recovered and recycled into the lower port of the column.

7. The process of claims 5 or 6 wherein the insoluble acid catalyst is an acidic ion exchange resin.

8. The process of claim 5 wherein the feeding of the alcohol relative to the citric acid is such that a molar ratio of alcohol to citric acid is provided between about 5:1 and 20:1.

9. The process of claim 5 wherein the feeding of the alcohol relative to the feeding of the citric acid is such that the percentage of citric acid conversion to the citric acid tri-ester is greater than 50 percent.

10. The process of any one of claims 1, 2 or 4 wherein the alcohol is ethanol and the catalyst is an acidic ion exchange resin.

11. The process of any one of claims 5, 6, 8 or 9 wherein the alcohol is ethanol and wherein the catalyst is an acidic ion exchange resin.

12. The process of claim 5 wherein the pressure in the column is between 1.0 and 4.0 atmospheres.

13. The process of claim 1 for producing a tri-ester, wherein the feeding of the mixture into the upper port of the column further comprises a mixture of mono-, di- and tri-esters of the citric acid and the alcohol generated from an esterification pre-reactor.

14. The process of claim 5 for producing a tri-ester, wherein the feeding of the mixture into the upper port of the column further comprises a mixture of mono-, di- and tri-esters of the citric acid and the alcohol generated from an esterification pre-reactor.

15. The process of claim 1 wherein the pressure in the column is between 1.0 and 4.0 atmospheres.

16. The process of claim 1, wherein the reboiler maintains the temperature at the bottom of the column below 120° C.

17. The process of claim 5, wherein the reboiler maintains the temperature at the bottom of the column below 120° C.

18. The process of claim 1 wherein the feeding of the alcohol relative to the citric acid is such that a molar ratio of alcohol to citric acid is provided between about 15:1 and 20:1.

19. The process of claim 1 wherein the alcohol is ethanol and the tri-ester produced is tri-ethyl citrate.

20. The process of claim 5 wherein the feeding of the alcohol relative to the citric acid is such that a molar ratio of alcohol to citric acid is provided between about 15:1 and 20:1.

21. The process of claim 5 wherein the alcohol is ethanol and the tri-ester produced is tri-ethyl citrate.

* * * * *